US011177020B2

(12) United States Patent
Jabara et al.

(10) Patent No.: US 11,177,020 B2
(45) Date of Patent: Nov. 16, 2021

(54) METHODS AND USES FOR MOLECULAR TAGS

(71) Applicant: The University of North Carolina at Chapel Hill, Chapel Hill, NC (US)

(72) Inventors: Cassandra B. Jabara, Ridgefield, CT (US); Jeffrey A. Anderson, Pennington, NJ (US); Ronald I. Swanstrom, Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 407 days.

(21) Appl. No.: 14/381,526

(22) PCT Filed: Feb. 27, 2013

(86) PCT No.: PCT/US2013/027891
§ 371 (c)(1),
(2) Date: Oct. 14, 2014

(87) PCT Pub. No.: WO2013/130512
PCT Pub. Date: Sep. 6, 2013

(65) Prior Publication Data
US 2016/0026758 A1    Jan. 28, 2016

Related U.S. Application Data

(60) Provisional application No. 61/603,909, filed on Feb. 27, 2012.

(51) Int. Cl.
*C12Q 1/6853* (2018.01)
*C12Q 1/689* (2018.01)
*C12Q 1/70* (2006.01)
*G16B 30/10* (2019.01)
*G16B 30/00* (2019.01)
*C12Q 1/6874* (2018.01)

(52) U.S. Cl.
CPC ............. *G16B 30/10* (2019.02); *C12Q 1/689* (2013.01); *C12Q 1/6853* (2013.01); *C12Q 1/6874* (2013.01); *C12Q 1/703* (2013.01); *G16B 30/00* (2019.02); *C12Q 2600/156* (2013.01); *C12Q 2600/16* (2013.01); *C12Q 2600/172* (2013.01)

(58) Field of Classification Search
None
See application file for complete search history.

(56) References Cited

U.S. PATENT DOCUMENTS

| | | | |
|---|---|---|---|
| 4,725,536 A | 2/1988 | Fritsch et al. |
| 5,124,246 A | 6/1992 | Urdea et al. |
| 5,149,625 A | 9/1992 | Church et al. |
| 5,200,314 A | 4/1993 | Urdea |
| 5,424,186 A | 6/1995 | Fodor et al. |
| 5,424,413 A | 6/1995 | Hogan et al. |
| 5,445,934 A | 8/1995 | Fodor et al. |
| 5,604,097 A | 2/1997 | Brenner |
| 5,635,352 A | 6/1997 | Urdea et al. |
| 5,635,400 A | 6/1997 | Brenner |
| 5,648,245 A | 7/1997 | Fire et al. |
| 5,654,413 A | 8/1997 | Brenner |
| 5,656,731 A | 8/1997 | Urdea |
| 5,658,737 A | 8/1997 | Nelson et al. |
| 5,714,330 A | 2/1998 | Brenner et al. |
| 5,744,305 A | 4/1998 | Fodor et al. |
| 5,759,778 A | 6/1998 | Li et al. |
| 5,763,175 A | 6/1998 | Brenner |
| 5,800,992 A | 9/1998 | Fodor et al. |
| 5,846,719 A | 12/1998 | Brenner et al. |
| 5,854,033 A | 12/1998 | Lizardi |
| 5,871,928 A | 2/1999 | Fodor et al. |
| 5,925,525 A | 7/1999 | Fodor et al. |
| 5,935,793 A | 8/1999 | Wong |
| 5,968,740 A | 10/1999 | Fodor et al. |
| 5,981,176 A | 11/1999 | Wallace |
| 5,981,179 A | 11/1999 | Lorinez et al. |
| 6,013,445 A | 1/2000 | Albrecht et al. |
| 6,040,138 A | 3/2000 | Lockhart et al. |
| 6,046,005 A | 4/2000 | Ju et al. |
| 6,060,596 A | 5/2000 | Lerner et al. |
| 6,114,149 A | 9/2000 | Fry et al. |
| 6,117,631 A | 9/2000 | Nilsen |

(Continued)

FOREIGN PATENT DOCUMENTS

| | | |
|---|---|---|
| DE | 102008025656 A1 | 12/2009 |
| EP | 0799897 A1 | 10/1997 |

(Continued)

OTHER PUBLICATIONS

Machine translation of WO2009152928, generated May 29, 2017 (57 pages).*
ABI 3100 User Reference Guide (142 pages) (Year: 2002).*
Sogin et al. Microbial diversity in the deep sea and the underexplored "rare biosphere". PNAS 103:12115-12120. (Year: 2006).*
Zagordi et al. Error correction of next-generation sequencing data and reliable estimation of HIV quasispecies. Nucleic Acids Research 38:7400-7409. (Year: 2010).*
Brodin Johanna et al.; "Challenges with using primer IDs to improve accuracy of next generation sequencing" PLOS One; 10(3): E0119123: 1-12 (2015).
Extended European Search Report and written opinion dated Dec. 14, 2015 for EP 13754428.4.

(Continued)

*Primary Examiner* — Samuel C Woolwine
(74) *Attorney, Agent, or Firm* — Olive Law Group, PLLC; Nathan P. Letts

(57) ABSTRACT

Methods and uses for molecular tags are disclosed. Molecular tags may be attached to nucleic acid molecules. The attachment of the nucleic acid molecules prior to PCR amplification and sequencing improves the accuracy of genetic analysis and detection of genetic variations and diversity. Molecular tags may also be used for detection of drug-resistant variants. Methods for using molecular tags for determining and correcting PCR errors and/or sequencing error are also disclosed.

24 Claims, 25 Drawing Sheets
Specification includes a Sequence Listing.

(56) References Cited

U.S. PATENT DOCUMENTS

| | | |
|---|---|---|
| 6,124,092 A | 9/2000 | O'Neill et al. |
| 6,138,077 A | 10/2000 | Brenner |
| 6,140,489 A | 10/2000 | Brenner |
| 6,172,214 B1 | 1/2001 | Brenner |
| 6,197,506 B1 | 3/2001 | Fodor et al. |
| 6,235,475 B1 | 5/2001 | Brenner et al. |
| 6,268,152 B1 | 7/2001 | Fodor et al. |
| 6,284,460 B1 | 9/2001 | Fodor et al. |
| 6,309,822 B1 | 10/2001 | Fodor et al. |
| 6,309,823 B1 | 10/2001 | Cronin et al. |
| 6,326,148 B1 | 12/2001 | Pauletti et al. |
| 6,355,431 B1 | 3/2002 | Chee et al. |
| 6,355,432 B1 | 3/2002 | Fodor et al. |
| 6,395,491 B1 | 5/2002 | Fodor et al. |
| 6,406,848 B1 | 6/2002 | Bridgham et al. |
| 6,440,667 B1 | 8/2002 | Fodor et al. |
| 6,440,706 B1 | 8/2002 | Vogelstein et al. |
| 6,451,536 B1 | 9/2002 | Fodor et al. |
| 6,458,530 B1 | 10/2002 | Morris et al. |
| 6,468,744 B1 | 10/2002 | Cronin et al. |
| 6,489,114 B2 | 12/2002 | Laayoun et al. |
| 6,492,121 B2 | 12/2002 | Kurane et al. |
| 6,512,105 B1 | 1/2003 | Hogan et al. |
| 6,514,699 B1 | 2/2003 | O'Neill et al. |
| 6,544,739 B1 | 4/2003 | Fodor et al. |
| 6,551,784 B2 | 4/2003 | Fodor et al. |
| 6,576,424 B2 | 6/2003 | Fodor et al. |
| 6,600,996 B2 | 7/2003 | Webster et al. |
| 6,629,040 B1 | 9/2003 | Goodlett et al. |
| 6,653,077 B1 | 11/2003 | Brenner |
| 6,753,147 B2 | 6/2004 | Vogelstein et al. |
| 6,849,404 B2 | 2/2005 | Park et al. |
| 6,852,488 B2 | 2/2005 | Fodor et al. |
| 6,858,412 B2 | 2/2005 | Willis et al. |
| 7,424,368 B2 | 9/2008 | Huang et al. |
| 7,537,897 B2 | 5/2009 | Brenner et al. |
| 7,544,473 B2 | 6/2009 | Brenner |
| 7,635,566 B2 | 12/2009 | Brenner |
| 7,822,555 B2 | 10/2010 | Huang et al. |
| 7,824,889 B2 | 11/2010 | Vogelstein et al. |
| 7,915,015 B2 | 3/2011 | Vogelstein et al. |
| 7,985,546 B2 | 7/2011 | Church et al. |
| 8,148,068 B2 | 4/2012 | Brenner |
| 8,168,385 B2 | 5/2012 | Brenner |
| 8,241,850 B2 | 8/2012 | Brenner |
| 8,298,767 B2 | 10/2012 | Brenner et al. |
| 8,318,433 B2 | 11/2012 | Brenner |
| 8,445,205 B2 | 5/2013 | Brenner |
| 8,470,996 B2 | 6/2013 | Brenner |
| 8,476,018 B2 | 7/2013 | Brenner |
| 8,481,292 B2 | 7/2013 | Casbon et al. |
| 8,535,889 B2 | 9/2013 | Larson et al. |
| 8,563,274 B2 | 10/2013 | Brenner et al. |
| 8,603,749 B2 | 12/2013 | Gillevet |
| 8,679,756 B1 | 3/2014 | Brenner et al. |
| 8,685,678 B2 | 4/2014 | Casbon et al. |
| 8,835,358 B2 | 9/2014 | Fodor et al. |
| 9,476,095 B2 * | 10/2016 | Vogelstein ............ C12Q 1/6874 |
| 2002/0072058 A1 | 6/2002 | Voelker et al. |
| 2003/0003490 A1 | 1/2003 | Fan et al. |
| 2003/0049616 A1 | 3/2003 | Brenner et al. |
| 2003/0104436 A1 | 6/2003 | Morris et al. |
| 2003/0175771 A1* | 9/2003 | Velculescu ............ C12Q 1/6886<br>435/6.12 |
| 2003/0186251 A1 | 10/2003 | Dunn et al. |
| 2003/0207300 A1 | 11/2003 | Matray et al. |
| 2004/0096892 A1 | 5/2004 | Wang et al. |
| 2004/0146901 A1 | 7/2004 | Morris et al. |
| 2004/0157243 A1 | 8/2004 | Huang et al. |
| 2004/0259118 A1 | 12/2004 | Macevicz |
| 2005/0019776 A1 | 1/2005 | Callow et al. |
| 2005/0250147 A1 | 11/2005 | Macevicz |
| 2006/0035258 A1 | 2/2006 | Tadakamalla et al. |
| 2006/0073506 A1 | 4/2006 | Christians et al. |
| 2006/0211030 A1 | 9/2006 | Brenner |
| 2006/0263709 A1 | 11/2006 | Matsumura et al. |
| 2006/0263789 A1 | 11/2006 | Kincaid |
| 2007/0020640 A1 | 1/2007 | McCloskey et al. |
| 2007/0065823 A1 | 3/2007 | Dressman et al. |
| 2007/0178478 A1 | 8/2007 | Dhallan et al. |
| 2008/0194414 A1 | 8/2008 | Albert et al. |
| 2008/0274458 A1 | 11/2008 | Latham et al. |
| 2008/0299609 A1 | 12/2008 | Kwon et al. |
| 2008/0318802 A1 | 12/2008 | Brenner |
| 2009/0105959 A1 | 4/2009 | Braverman et al. |
| 2009/0137407 A1 | 5/2009 | Church et al. |
| 2009/0226891 A2 | 9/2009 | Nova et al. |
| 2009/0253586 A1 | 10/2009 | Nelson et al. |
| 2009/0298709 A1 | 12/2009 | Ma |
| 2010/0069250 A1 | 3/2010 | White et al. |
| 2010/0105049 A1 | 4/2010 | Ehrich et al. |
| 2010/0105886 A1 | 4/2010 | Woudenberg et al. |
| 2010/0291666 A1 | 11/2010 | Collier et al. |
| 2010/0323348 A1 | 12/2010 | Hamady et al. |
| 2011/0059436 A1 | 3/2011 | Hardin et al. |
| 2011/0070584 A1 | 3/2011 | Wohlgemuth et al. |
| 2011/0072889 A1 | 3/2011 | Albitar et al. |
| 2011/0160078 A1 | 6/2011 | Fodor et al. |
| 2011/0201507 A1 | 8/2011 | Rava et al. |
| 2011/0230358 A1 | 9/2011 | Rava |
| 2011/0244455 A1 | 10/2011 | Larson et al. |
| 2011/0294689 A1 | 12/2011 | Namsaraev |
| 2012/0010091 A1 | 1/2012 | Linnarson |
| 2012/0156675 A1 | 6/2012 | Lueerssen et al. |
| 2012/0220022 A1 | 8/2012 | Ehrlich et al. |
| 2012/0316074 A1 | 12/2012 | Saxonov |
| 2013/0005585 A1 | 1/2013 | Anderson et al. |
| 2013/0022977 A1 | 1/2013 | Lapidus et al. |
| 2013/0116130 A1 | 5/2013 | Fu et al. |
| 2013/0210643 A1 | 8/2013 | Casbon et al. |
| 2013/0224743 A1 | 8/2013 | Casbon et al. |
| 2013/0237458 A1 | 9/2013 | Casbon et al. |
| 2013/0267424 A1 | 10/2013 | Casbon et al. |
| 2014/0155295 A1 | 6/2014 | Hindson et al. |
| 2014/0227684 A1 | 8/2014 | Hindson et al. |
| 2014/0228255 A1 | 8/2014 | Hindson et al. |
| 2014/0235506 A1 | 8/2014 | Hindson et al. |
| 2014/0274811 A1 | 9/2014 | Arnold |
| 2014/0287963 A1 | 9/2014 | Hindson et al. |
| 2014/0315211 A1 | 10/2014 | Sugino et al. |
| 2014/0378322 A1 | 12/2014 | Hindson et al. |
| 2014/0378345 A1 | 12/2014 | Hindson et al. |
| 2014/0378349 A1 | 12/2014 | Hindson et al. |
| 2014/0378350 A1 | 12/2014 | Hindson et al. |
| 2015/0005185 A1 | 1/2015 | Fodor et al. |
| 2015/0005199 A1 | 1/2015 | Hindson et al. |
| 2015/0005200 A1 | 1/2015 | Hindson et al. |
| 2015/0066385 A1 | 3/2015 | Schnall-Levin et al. |
| 2015/0099661 A1 | 4/2015 | Fodor et al. |
| 2015/0099673 A1 | 4/2015 | Fodor et al. |
| 2015/0118680 A1 | 4/2015 | Fodor et al. |
| 2015/0119255 A1 | 4/2015 | Fodor et al. |
| 2015/0119256 A1 | 4/2015 | Fodor et al. |
| 2015/0119257 A1 | 4/2015 | Fodor et al. |
| 2015/0119258 A1 | 4/2015 | Fodor et al. |
| 2015/0119290 A1 | 4/2015 | Fodor et al. |
| 2015/0133319 A1 | 5/2015 | Fu et al. |
| 2015/0141292 A1 | 5/2015 | Fodor et al. |
| 2015/0299784 A1 | 10/2015 | Fan et al. |
| 2016/0010151 A1 | 1/2016 | Fan et al. |
| 2016/0055632 A1 | 2/2016 | Fu et al. |

FOREIGN PATENT DOCUMENTS

| | | |
|---|---|---|
| EP | 1473080 A2 | 11/2004 |
| EP | 1647600 A2 | 4/2006 |
| EP | 2623613 A1 | 8/2013 |
| WO | 198901050 A1 | 2/1989 |
| WO | 199710365 A1 | 3/1997 |
| WO | 199928505 A1 | 6/1999 |
| WO | 200058516 A2 | 10/2000 |
| WO | 2002056014 A2 | 7/2002 |
| WO | 2004017374 A2 | 2/2004 |
| WO | 2005071110 A2 | 8/2005 |

(56) References Cited

FOREIGN PATENT DOCUMENTS

| WO | 2005080604 A2 | 9/2005 |
|---|---|---|
| WO | 2005111242 A2 | 11/2005 |
| WO | 2006071776 A2 | 7/2006 |
| WO | 2006102264 A1 | 9/2006 |
| WO | 2007087310 A2 | 8/2007 |
| WO | 2007087312 A2 | 8/2007 |
| WO | 2008096318 A2 | 8/2008 |
| WO | 2009152928 A2 | 12/2009 |
| WO | 2009152928 A3 | 2/2010 |
| WO | 2010117620 A2 | 10/2010 |
| WO | 2011123246 A2 | 10/2011 |
| WO | 2011143659 A2 | 11/2011 |
| WO | 2012038839 A2 | 3/2012 |
| WO | 2012042374 A2 | 4/2012 |
| WO | 2012048341 A1 | 4/2012 |
| WO | 2012083225 A2 | 6/2012 |
| WO | 2012129363 A2 | 9/2012 |
| WO | 2012140224 A1 | 10/2012 |
| WO | 2012142213 A2 | 10/2012 |
| WO | 2012148477 A1 | 11/2012 |
| WO | 2013019075 A2 | 2/2013 |
| WO | 2013130674 A1 | 9/2013 |
| WO | 2013188872 A1 | 12/2013 |
| WO | 2014018460 A1 | 1/2014 |
| WO | 2014028537 A1 | 2/2014 |
| WO | 2014093676 A1 | 6/2014 |
| WO | 2014108850 A2 | 7/2014 |
| WO | 2014124336 A2 | 8/2014 |
| WO | 2014124338 A1 | 8/2014 |
| WO | 2014210353 A2 | 12/2014 |
| WO | 2015031691 A1 | 3/2015 |

OTHER PUBLICATIONS

Keys Jessica R et al.; "Primer ID Informs Next-Generation Sequencing Platforms and Reveal s Preexisting Drug Resistance Mutations i n the HIV-1 Reverse Transcriptase Coding Domain"; Aids Research and Human Retroviruses; 31(6): 658-668 (2015).
Teemu Kivioja et al.; "Counting absolute numbers of molecules using unique molecular identifiers"; Nature Methods; 9(1): 72-74 (2012).
Hiatt, et al. Single molecule molecular inversion probes for targeted, high-accuracy detection of low-frequency variation. Genome Res. May 2013;23(5):843-54. doi: 10.1101/gr.147686.112. Epub Feb. 4, 2013.
Hollas, et al. A stochastic approach to count RNA molecules using DNA sequencing methods. Lecture Notes in Computer Science, 2812: 55-62 (2003).
Hug, et al. Measurement of the number of molecules of a single mRNA species in a complex mRNA preparation. J Theor Biol. Apr. 21, 2003;221(4):615-24.
Ingolia, et al. Genome-wide analysis in vivo of translation with nucleotide resolution using ribosome profiling. Science. Apr. 10, 2009;324(5924);218-23. Epub Feb. 12, 2009.
International search report and written opinion dated Feb. 3, 2015 for PCT/US2014/053301.
International search report and written opinion dated May 7, 2012 for PCT/IB2011/003160.
International search report and written opinion dated Jun. 6, 2012 for PCT/US2011/065291.
International search report and written opinion dated Aug. 16, 2013 for PCT/US2013/027891.
International search report and written opinion dated Dec. 19, 2014 for PCT Application No. US2014/059542.
International search report dated Aug. 6, 2014 for PCT Application No. GB1408829.8.
Islam, et al.,Characterization of the single-cell transcriptional landscape by highly multiplex RNA-seq. Genome Research, 2011,21: 1160-1167.
Jabara, C. Capturing the cloud: High throughput sequencing of multiple individual genomes from a retroviral ooopulation. Biology Lunch Bunch Series, Training Initiatives in Biomedical & Biological Sciences of the University of Morth Carolina at Chapel Hill, Apr. 23, 2010.
Jabara, et al. Accurate sampling and deep sequencing of the HIV-1 protease gene using a Primer ID, Dec. 3, 2011, PNAS, vol. 108, No. 50, p. 20166-20171.
Kanagawa. Bias and artifacts in multitemplate polymerase chain reactions (PCR), 2003, Journal of Bioscience and Bioengineering, vol. 96, No. 4, p. 317-323.
Kinde, et al. Detection and quantification of rare mutations with massively parallel sequencing. Proc Natl Acad Sci U S A. Jun. 7, 2011;108(23):9530-5. doi: 10.1073/pnas.1105422108. Epub May 17, 2011.
Kivioja, et al. Counting absolute numbers of molecules using unique molecular identifiers. Nat Methods. Nov. 20, 2011;9(1):72-4. doi: 10.1038/nmeth.1778.
Koboldt, et al. VarScan: variant detection in massively parallel sequencing of individual and pooled samples. Bioinformatics. Sep. 1, 2009;25(17):2283-5. doi: 10.1093/bioinformatics/btp373. Epub Jun. 19, 2009.
Konig, et al. iCLIP reveals the function of hnRNAP particles in splicing at individual nucleotide resolution, Jul. 2010, Nature Structural & Molecular Biology, 17(7):909-916.
Larson, et al. A single molecule view of of gene expression. Trends Cell Biol. Nov. 2009;19(11):630-7. Epub Oct. 8, 2009.
Lee, et al.,Highly multiplexed subcellular RNA sequencing in situ. Science. Mar. 21, 2014;343(6177):1360-3. doi 10.1126/science. 1250212. Epub Feb. 27, 2014.
Letter regarding the opposition procedure dated Jul. 22, 2015 for EP Application No. 11810645.9.
Lizardi, et al. Mutation detection and single-molecule counting using isothermal rolling-circle amplification. Nat Genet. Jul. 1998;19(3):225-32.
Lockhart, et al. Expression monitoring by hybridization to high-density oligonucleotide arrays. Nature Biotechnology, 14: 1675-1680 (1996).
Lovatt, et al.,Transcriptome in vivo analysis (TIVA) of spatially defined single cells in live tissue. Nat Methods. Feb. 2014;11(2):190-6. doi: 10.1038/nmeth.2804. Epub Jan. 12, 2014.
Lucito, et al. Representational Oligonucleotide Microarray Analysis: A High-Resolution Method to Detect Genome Copy Number Variation. Genome Research, 13: 2291-2305.
Maamar, et al. Noise in Gene Expression Determines Cell Fate in Bacillus subtilis. Science, 317: 526-529 (2007).
Macaulay, et al.,G&T-seq: parallel sequencing of single-cell genomes and transcriptomes. Nature Methods, 2015, p. 1-7.
Makrigiorgos, et al., A PCR-Based amplification method retaining quantative difference between two complex genomes. Nature Biotech, vol. 20, No. 9, pp. 936-939 (Sep. 2002).
Mccloskey, et al. Encoding PCR products with batch-stamps and barcodes. Biochem Genet. Dec. 2007;45 (11-12)761-7. Epub Oct. 23, 2007.
Medvedev, et al. Detecting copy number variation with mated short reads. Genome Res. Nov. 2010,20(11):1613-22. doi: 10.1101/gr. 106344.110. Epub Aug. 30, 2010.
Mei, et al. Identification of recurrent regions of Copy-Number Variants across multiple individuals. BMC Bioinformatics. Mar. 22, 2010;11:147. doi: 10.1186/1471-2105-11-147.
Mortazavi, et al. Mapping and quantifying mammalian transcriptomes by RNA-Seq. Nat. Methods. 2008; 5, 621-628.
Newell, et al. Cytometry by time-of-flight shows combinatorial cytokine expression and virus-specific cell niches within a continuum of CD8+ T cell phenotypes. Immunity. Jan. 27, 2012;36(1):142-52. doi: 10.1016/j.immuni.2012.01.002.
Notice of allowance dated Mar. 21, 2014 for U.S. Appl. No. 12/969,581.
Notice of allowance dated Jun. 19, 2014 for U.S. Appl. No. 12/969,581.
Notice of allowance dated Aug. 22, 2014 for U.S. Appl. No. 12/969,581.
Notice of opposition dated Jul. 22, 2015 for EP Application No. 11810645.9.

(56) References Cited

OTHER PUBLICATIONS

Notice of opposition dated Sep. 7, 2015 for EP Application No. 11810645.9.
Office action dated Feb. 18, 2015 for U.S. Appl. No. 14/540,007.
Office action dated Feb. 26, 2015 for U.S. Appl. No. 14/540,029.
Office action dated Mar. 19, 2015 for U.S. Appl. No. 14/540,018.
Office action dated May 7, 2015 for U.S. Appl. No. 13/327,526.
Office action dated Sep. 1, 2015 for U.S. Appl. No. 14/540,029.
Office action dated Sep. 24, 2015 for U.S. Appl. No. 14/540,007.
Office action dated Oct. 3, 2013 for U.S. Appl. No. 12/969,581.
Office action dated Oct. 6, 2015 for U.S. Appl. No. 14/540,018.
Ogino, et al. Quantification of PGR bias caused by a single nucleotide polymorphism in SMN gene dosage analysis. J Mol Diagn. Nov. 2002;4(4); 185-90.
Parameswaran, et al. A pyrosequencing-tailored nucleotide barcode design unveils opportunities for large-scale sample multiplexing. Nucleic Acids Res. 2007;35(19)e130.
Park, et al. Discovery of common Asian copy number variants using integrated high-resolution array CGH and massively parallel DNA sequencing. Nat Genet. May 2010;42(5):400-5. doi: 10.1038/ng.555. Epub Apr. 4, 2010.
Pihlak, et al. Rapid genome sequencing with short universal tiling probes. Nature Biotechnology, 26: 676-684 (2008).
Pinkel, et al. Comparative Genomic Hybridization. Annual Review of Genomics and Human Genetics, 6: 331-354 (2005).
Pleasance, et al. A small-cell lung cancer genome with complex signatures of tobacco exposure. Nature. Jan. 14, 2010;463(7278):184-90. doi: 10.1038/nature08629. Epub Dec. 16, 2009.
Qiu, et al. DNA sequence-based "bar codes" for tracking the origins of expressed sequence tags from a maize cDNA library constructed using multiple mRNA sources. Plant Physiol. Oct. 2003;133(2):475-81.
Response with alllowed claims dated Mar. 4, 2014 for U.S. Appl. No. 12/969,581.
Sasagawa, et al.,Quartz-Seq: a highly reproducible and sensitive single-cell RNA sequencing method, reveals non-genetic gene-expression heterogeneity. Genome Biology, 2013, 14:R31.
Satija, et al.,Spatial reconstruction of single-cell gene expression data. Nature Biotechnology, vol. 33, No. 5, May 2015, p. 495-508.
Schmitt, et al. Detection of ultra-rare mutations by next-generation sequencing. Proc Natl Acad Sci U S A. Sep. 4, 2012;109(36):14508-13. doi: 10.1073/pnas.1208715109. Epub Aug. 1, 2012.
Sebat, et al. Large-Scale Copy Number Polymorphism in the Human Genome. Science, 305: 525-528 (2004).
Shalek, et al. Single-cell transcriptomics reveals bimodality in expression and splicing in immune cells. Nature. Jun. 13, 2013;498(7453):236-40. doi: 10.1038/nature12172. Epub May 19, 2013.
Shiroguchi, et al. Digital RNA sequencing minimizes sequence-dependent bias and amplification noise with optimized single-molecule barcodes. Proc Natl Acad Sci U S A. Jan. 24, 2012;109(4):1347-52. doi: 10.1073/pnas.1118018109. Epub Jan. 9, 2012.
Shoemaker, et al. Quantitative phenotypic analysis of yeast deletion mutants using a highly parallel molecular bar-coding strategy. Nature Genetics, 14: 450-456 (1996).
Simpson, et al. Copy number variant detection in inbred strains from short read sequence data. Bioinformatics. Feb. 15, 2010;26(4):565-7. doi: 10.1093/bioinformatics/btp693. Epub Dec. 18, 2009.
Smith, et al. Highly-multiplexed barcode sequencing: an efficient method for parallel analysis of pooled samples. Nucleic Acids Research, 38(13): e142 (2010).
Tan, et al. Genome-wide comparison of DNA hydroxymethylation in mouse embryonic stem cells and neural progenitor cells by a new comparative hMeDIP-seq method. Nucleic Acids Res. Apr. 2013;41(7):e84. doi: 10.1093/nar/gkt091. Epub Feb. 13, 2013.
Taudien, et al. Haplotyping and copy number estimation of the highly polymorphic human beta-defensin locus on 8p23 by 454 amplicon sequencing. BMC Genomics. Apr. 19, 2010;11:252. doi: 10.1186/1471-2164-11-252.

The Tibbs Times newsletter.,UNC,Apr. 2010, pp. 1-17.
Tomaz, et al. Differential methylation as a cause of allele dropout at the imprinted GNAS locus. Genet Test Mol Biomarkers. Aug. 2010;14(4):455-60. doi: 10.1089/gtmb.2010.0029.
Treutlein, et al. Reconstructing lineage hierarchies of the distal lung epithelium using single-cell RNA-seq. Nature. May 15, 2014,509(7500):371-5. doi: 10.1038/nature13173. Epub Apr. 13, 2014.
U.S. Appl. No. 61/385,001, filed Sep. 21, 2010.
U.S. Appl. No. 61/432,119, filed Jan. 12, 2011.
Velculescu, et al. Characterization of the Yeast Transcriptome. Cell, 88: 243-251 (1997).
Velculescu, et al. Serial Analysis of Gene Expression. Science, 270: 484-487 (1995).
Vogelstein, et al. Digital PCR. Proc. Natl. Acad. Sci., 96(16): 9236-9241(1999).
Walker, et al. Isothermal in vitro amplification of DNA by a restriction enzyme/DNA polymerase system. Proc Natl Acad Sci U S A. Jan. 1, 1992;89(1):392-6.
Walsh, et al. Detection of inherited mutations for breast and ovarian cancer using genomic capture and massively parallel sequencing. Proc Natl Acad Sci U S A. Jul. 13, 2010;107(28):12629-33. doi: 10.1073/pnas.1007983107. Epub Jun. 28, 2010.
Wang, et al. iCLIP predicts the dual splicing effects of TIA-RNA interactions, Oct. 2010, PLoS Biol, 8(10):e 1000530.
Wang, et al. RNA-Seq: a revolutionary tool for transcriptomics. Nature Reviews Genetics, 10: 57-63 (2009).
Weber, et al. A real-time polymerase chain reaction assay for quantification of allele ratios and correction of amplification bias. Anal Biochem. Sep. 15, 2003;320(2):252-8.
Wittes, et al. Searching for Evidence of Altered Gene Expression: a Comment on Statistical Analysis of Microarray Data. Journal of the National Cancer Institute, 91(5): 400-401 (1999).
Wodicka, et al. Genome-wide expression monitoring in *Saccharomyces cerevisiae*. Nature Biotechnology, 15: 1359-1367 (1997).
Wojdacs, et al. Primer design versus PCR bias in methylation independent PCR amplifications. Epigenetics. May 16, 2009,4(4):231-4. Epub May 14, 2009.
Wood, et al. Using next-generation sequencing for high resolution multiplex analysis of copy number variation from nanogram quantities of DNA from formalin-fixed paraffin-embedded specimens. Nucleic Acids Res. Aug. 2010;38(14):e151. doi: 10.1093/nar/gkq510. Epub Jun. 4, 2010.
Wu, et al. Quantitative assessment of single-cell RNA-sequencing methods. Nat Methods. Jan. 2014;11(1):41-6. doi: 10.1038/nmeth.2694. Epub Oct. 20, 2013.
Yandell, et al. A probabilistic disease-gene finder for personal genomes. Genome Res. Sep. 2011;21(9):1529-42. doi: 10.1101/gr.123158.1 11. Epub Jun. 23, 2011.
Ye, et al. Fluorescent microsphere-based readout technology for multiplexed human single nucleotide polymorphism analysis and bacterial identification. Human Mutation, 17(4): 305-316 (2001).
Yoon, et al. Sensitive and accurate detection of copy number variants using read depth of coverage. Genome Res. Sep. 2009;19(9):1586-92. doi: 10.1101/gr.092981.109. Epub Aug. 5, 2009.
Zhang, et al. The impact of next-generation sequencing on genomics. J Genet Genomics. Mar. 20, 2011;38(3):95-109. doi: 10.1016/j.jgg.2011.02.003. Epub Mar. 15, 2011.
Zhang, et al.,DNA-based hybridization chain reaction for amplified bioelectronic signal and ultrasensitive detection of poroteins.,Anal Chem.,Jun. 19, 2012,84(12),5392-9.
Zhao, et al. Homozygous Deletions and Chromosome Amplifications in Human Lung Carcinomas Revealed by Single Nucleotide Polymorphism Array Analysis. Cancer Research, 65: 5561-5570 (2005).
Zhou, et al. Counting alleles reveals a connection between chromosome 18q loss and vascular invasion. Nature Biotechnology, 19: 78-81 (2001).
Achim, et al.,High-throughput spatial mapping of single-cell RNA-seq data to tissue of origin. Nature Biotechnology, vol. 33, No. 5, May 2015, p. 503-511.

(56) References Cited

OTHER PUBLICATIONS

Alkan, et al. Personalized copy number and segmental duplication maps using next-generation sequencing. Nat Genet. Oct. 2009;41(10):1061-7. doi: 10.1038/ng.437. Epub Aug. 30, 2009.
Anderson, et al.,2010, HIV-1 populations in semen arise through multiple mechanisms, PLOS Pathogens, 6(8) e1001053 (12 pages).
Ansorge. Next-generation DNA sequencing techniques. New Biotechnology, 25(4): 195-203 (2009).
Atanur, et al. The genome sequence of the spontaneously hypertensive rat: Analysis and functional significance. Genome Res. Jun. 2010;20(6):791-803. doi: 10.1101/gr.103499.109. Epub Apr. 29, 2010.
Audic, et al. The Significance of Digital Gene Expression Profiles. Genome Research, 7: 986-995 (1997).
Bendall, et al. Single-cell mass cytometry of differential immune and drug responses across a human hematopoietic continuum. Science. May 6, 2011;332(6030):687-96. doi: 10.1126/science.1198704.
Bonaldo, et al. Normalization and subtraction: two approaches to facilitate gene discovery. Genome Res. Sep. 1996;6(9);791-806.
Chen, et al.,Spatially resolved, highly multiplexed RNA profiling in single cells. Sciencexpress, Apr. 9, 2015, p. 1-21.
Church, et al. Multiplex DNA sequencing. Science, 240: 185-188 (1988).
Costello, et al. Discovery and characterization of artifactual mutations in deep coverage targeted capture sequencing data due to oxidative DNA damage during sample preparation. Nucleic Acids Res. Apr. 1, 2013;41(6):e67. doi: 10.1093/nar/gks1443. Epub Jan. 8, 2013.
Cox. Bar coding objects with DNA. Analyst. May 2001;126(5):545-7.
Craig, et al. Identification of genetic variants using bar-coded multiplexed sequencing. Nat Methods. Oct. 2008;5 (10):887-93. doi; 10.1038/nmeth.1251. Epub Sep. 14, 2008.
Cusanovich, et al.,Multiplex single-cell profiling of chromatin accessibility by combinatorial cellular indexing. Sciencexpress, May 7, 2014, p. 1-9.
Daines, et al. High-throughput multiplex sequencing to discover copy No. variants in Drosophila. Genetics. Aug. 2009;182(4):935-41 doi: 10.1534/genetics.109.103218. Epub Jun. 15, 2009.
D'Antoni, et al. Rapid quantitative analysis using a single molecule counting approach. Anal Biochem. May 1, 2006;352(1):97-109. Epub Feb. 10, 2006.
Daser, et al. Interrogation of genomes by molecular copy-number counting (MCC). Nature Methods, 3(6): 447-453 (2006).
De Saizieu, et al. Bacterial transcript imaging by hybridization of total RNA to oligonucleotide arrays. Nature Biotechnology, 16: 45-48 (1998).
Dirks, et al.,Triggered amplification by hybridization chain reaction.,Proc Natl Acad Sci U S A,Oct. 26, 2004,101(43),15275-8.
Braha, et al. Simultaneous stochastic sensing of divalent metal ions. Nature Biotechnology, 18: 1005-1007 (2000).
Bratke, et al. Differential expression of human granzymes A, B, and K in natural killer cells and during CD8+ T cell differentiation in peripheral blood. Eur J Immunol. Sep. 2005;35(9):2608-16.
Brenner, et al. Gene expression analysis by massively parallel signature sequencing (MPSS) on microbead arrays. Nature Biotechnology, 18: 630-634 (2000).
Brenner, et al. In vitro cloning of complex mixtures of DNA on microbeads: physical separation of differentially expressed cDNAs. Proc Natl Acad Sci U S A. Feb. 15, 2000;97(4):1665-70.
Carr, et al. Inferring relative proportions of DNA variants from sequencing electropherograms. Bioinformatics. Dec. 15, 2009;25(24):3244-50. doi: 10.1093/bioinformatics/btp583. Epub Oct. 9, 2009.
Casbon, et al. A method for counting PCR template molecules with application to next-generation sequencing. Nucleic Acids Res. Jul. 2011;39(12):e81. doi: 10.1093/nar/gkr217. Epub Apr. 13, 2011.

Castle, et al. DNA copy number including telomeres and mitochondria, assayed using next-generation sequencing. BMC Genomics. Apr. 16, 2010;11:244. doi: 10.1186/1471-2164-11-244.
Chamberlain, et al. Deletion screening of the Duchenne muscular dystrophy locus via multiplex DNA amplification. Nucleic Acids Res. Dec. 9, 1988;16(23):11141-56.
Chang, et al. Detection of allelic imbalance in ascitic supernatant by digital single nucleotide polymorphism analysis. Clin Cancer Res. Aug. 2002;8(8):2580-5.
Chee, et al. Accessing genetic information with high-density DNA arrays. Science, 274: 610-6 14 (1996).
Chee. Enzymatic multiplex DNA sequencing. Nucleic Acids Research, 19(12): 3301-3305 (1991).
Gunderson, et al.,Decoding randomly ordered DNA arrays. Genome Res. May 2004;14(5):870-7. Epub Apr. 12, 2004.
Gundry, et al. Direct mutation analysis by high-throughput sequencing: from germline to low-abundant, somatic variants. Mutat Res. Jan. 3, 2012;729(1-2):1-15. doi: 10.1016/mrfmmm.2011.10.001. Epub Oct. 12, 2011.
Gundry, et al. Direct, genome-wide assessment of DNA mutations in single cells. Nucleic Acids Res. Mar. 2012;40(5):2032-40. doi: 10.1093/nar/gkr949. Epub Nov. 15, 2011.
Hacia, et al. Determination of ancestral alleles for human single-nucleotide polymorphisms using high-density oligonucleotide arrays. Nature Genetics, 22: 164-167 (1999).
Hamady, et al. Error-correcting barcoded primers for pyrosequencing hundreds of samples in multiplex. Nat Methods. Mar. 2008;5(3):235-7. doi: 10.1038/nmeth.1184. Epub Feb. 10, 2008.
Harrington, et al.,2009, Cross-sectional characterization of HIV-1 env compartmentalization in cerebrospinal fluid over the full disease course, AIDS, 23(8) 907-915.
Hashimshony, et al. CEL-Seq: single-cell RNA-Seq by multiplexed linear amplification Cell Rep. Sep. 27, 2012;2(3):666-73. doi: 10.1016/j.celrep.2012.08.003. Epub Aug. 30, 2012.
Hensel, et al. Simultaneous identification of bacterial virulence genes by negative selection. Science. Jul. 21, 1995;269(5222):400-3.
Hiatt, et al. Parallel, tag-directed assembly of locally derived short sequence reads. Nat Methods. Feb. 2010;7(2):119-22. doi: 10.1038/nmeth.1416. Epub Jan. 17, 2010.
European search report and search opinion dated Jul. 17, 2015 for EP Application No. 13755319.4.
Fan, et al. Microfluidic digital PCR enables rapid prenatal diagnosis of fetal aneuploidy. Am Obstet Gynecol. 2009; 200:543.e1-543.e7.
Fan, et al. Non-invasive prenatal measurement of the fetal genome. Nature. Jul. 19, 2012;487(7407):320-4. doi: 10.1038/nature11251.
Fan, et al. Parallel Genotyping of Human SNPs Using Generic High-density Oligonucleotide Tag Arrays. Genome Research, 10: 853-860 (2000).
Fan, et al.,Expression profiling. Combinatorial labeling of single cells for gene expression cytometry. Science. Feb. 6, 2015;347(6222):1258367. doi: 10.1126/science.1258367.
Fox-Walsh, et al.,A multiplex RNA-seq strategy to profile poly(A+) RNA: application to analysis of transcription response and 3' end formation.,Genomics,Oct. 2011,98(4),266-71.
Fu, et al. Counting individual DNA molecules by the stochastic attachment of diverse labels. Proc Natl Acad Sci U S A. May 31, 2011;108(22):9026-31. Epub May 11, 2011.
Fu, et al. Digital encoding of cellular mRNAs enabling precise and absolute gene expression measurement by single-molecule counting. Anal Chem. Mar. 18, 2014;86(6):2867-70. doi: 10.1021/ac500459p. Epub Mar. 4, 2014.
Gerry, et al. Universal DNA microarray method for multiplex detection of low abundance point mutations. Journal of Molecular Biology, 292(2): 251-262 (1999).
Gillespie. .Exact stochastic simulation of coupled chemical reactions. The Journal of Physical Chemistry, 81(25): 2340-2361 (1977).
Grant, et al. SNP genotyping on a genome-wide amplified DOP-PCR template. Nucleic Acids Res. Nov. 15, 2002;30(22):e125.
Communication pursuant to Article 94(3) EPC issued in counterpart EP Application No. 13754428.4 dated Mar. 16, 2018 (six (6) pages).
Jabara, Cassandra B. et al., "Accurate Sampling and Deep Sequencing HIV-1 Protease Using Primer ID" CROI, Mar. 1, 2011.

(56) References Cited

OTHER PUBLICATIONS

Miner, et al. Molecular Barcodes Detect Redundancy and Contamination in Hairpin-bisulfite PCR. Department of Biology, University of Washington, Seattle. Published Sep. 30, 2004. Nucleic Acids Research, vol. 32, No. 17 (four (4) pages).
Communication pursuant to Article 94(3) EPC issued in counterpart EP Application No. 13754428.4 dated Feb. 6, 2019 (six (6) pages).
Communication pursuant to Rule 71(3) EPC issued in counterpart EP Application No. 13754428.4 dated Jul. 9, 2019 (seven (7) pages).

* cited by examiner

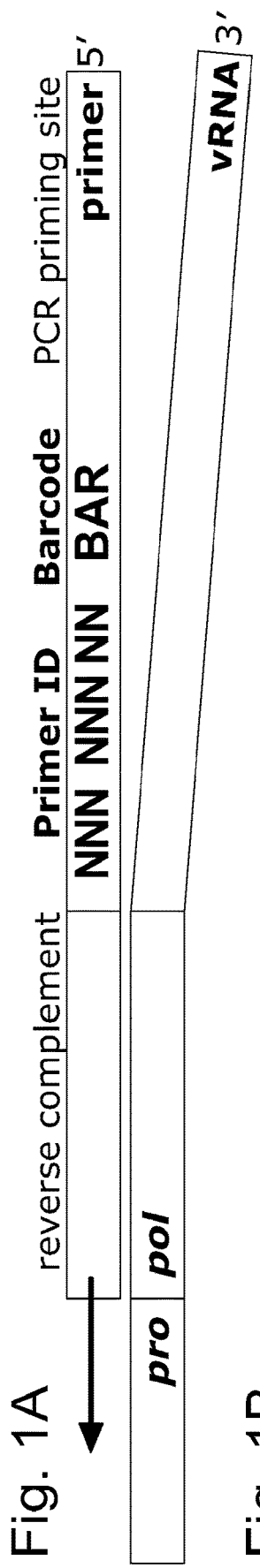

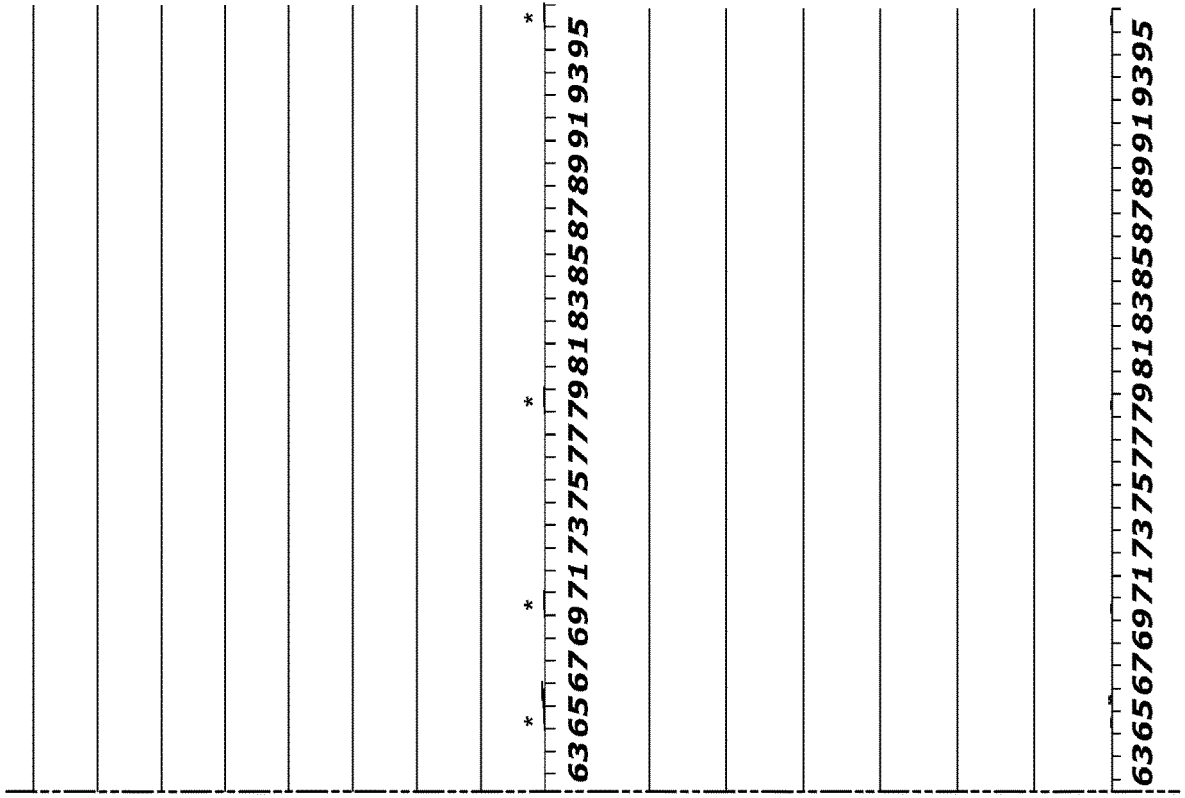

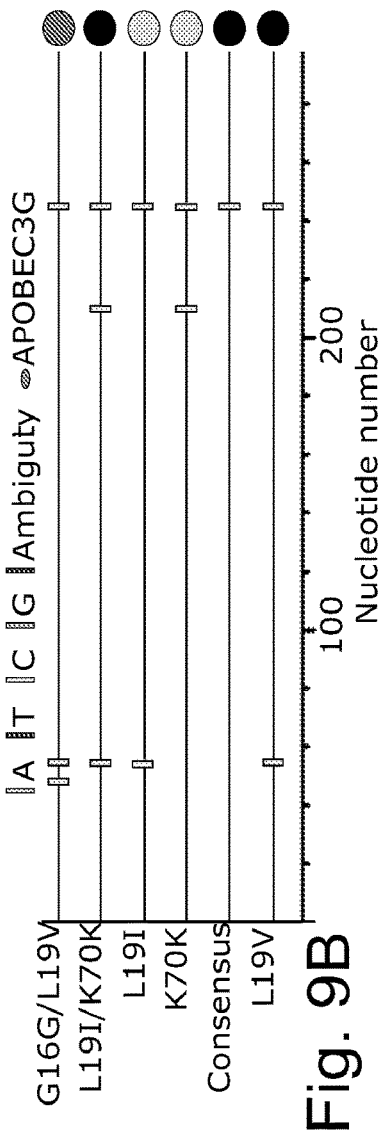
Fig. 9A
Fig. 9B
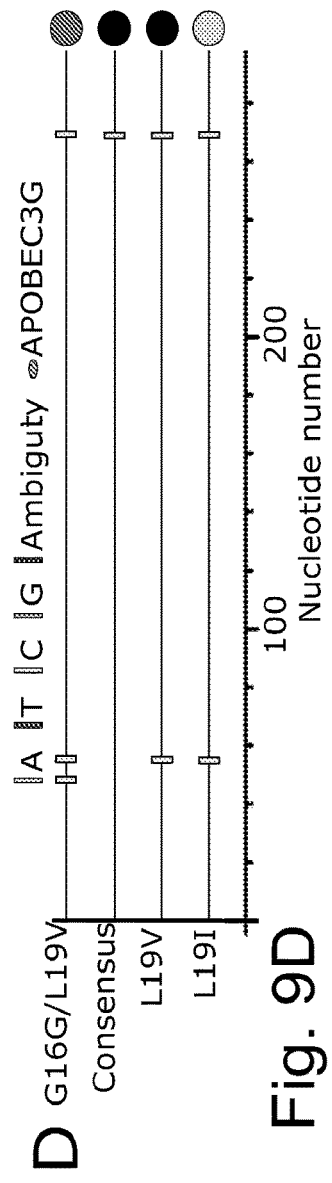
Fig. 9C
Fig. 9D
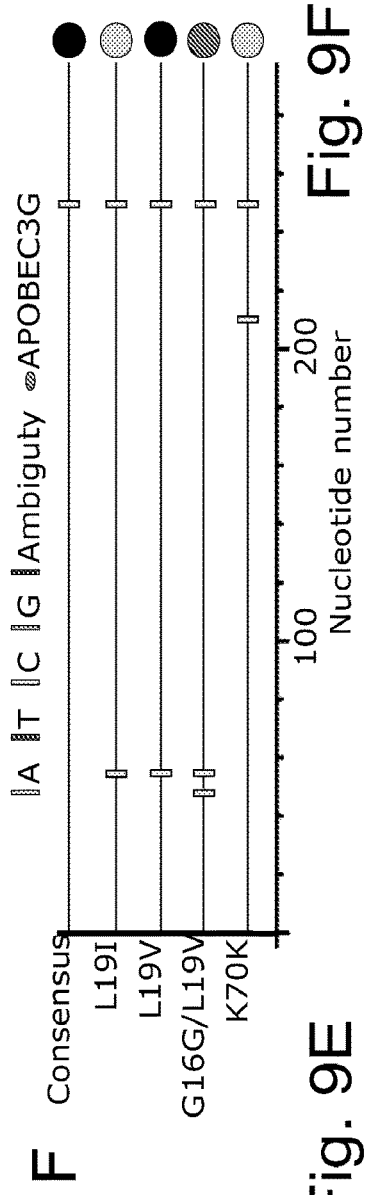
Fig. 9E
Fig. 9F

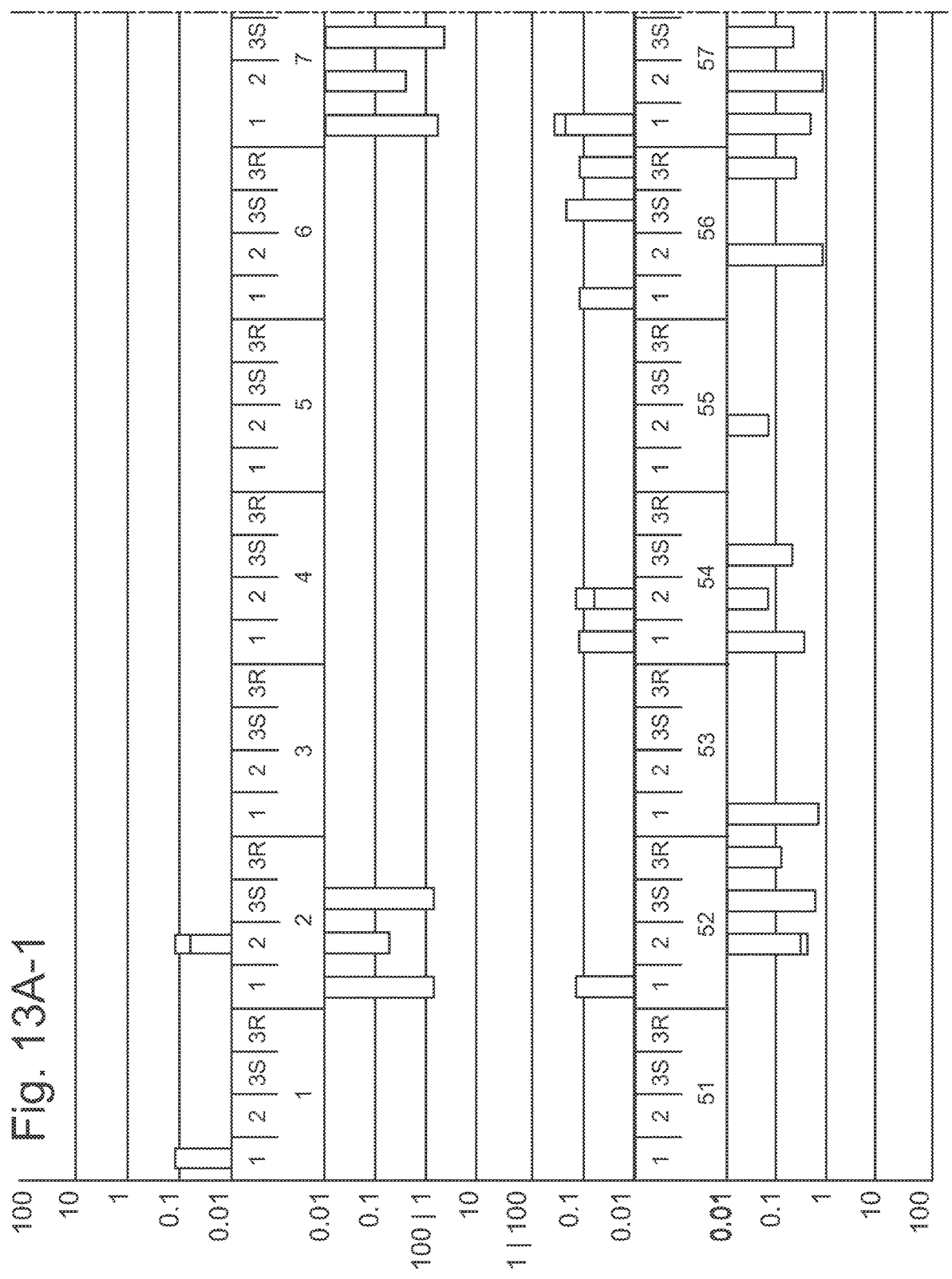

| Sample | T1 | T1 | T1 |
|---|---|---|---|
| Ritonavir | − | − | + |
| Total sequences | 21,706 | 25,414 | 28,264 |
| Consensus sequences | 892 | 1,576 | 2,283 |

Fig. 13B

SEQUENCE LISTING

<160> NUMBER OF SEQ ID NOS: 6

<210> SEQ ID NO 1
<211> LENGTH: 11
<212> TYPE: DNA
<213> ORGANISM: Artificial Sequence
<220> FEATURE:

```
<223> OTHER INFORMATION: Laboratory synthesized sequence

<400> SEQUENCE: 1
cataatacta g                                                           11

<210> SEQ ID NO 2
<211> LENGTH: 67
<212> TYPE: DNA
<213> ORGANISM: Artificial Sequence
<220> FEATURE:
<223> OTHER INFORMATION: Laboratory synthesized sequence
<220> FEATURE:
<221> NAME/KEY: misc_feature
<222> LOCATION: (28)..(30)
<223> OTHER INFORMATION: nnn may be TCA, GTA, and TAT
<220> FEATURE:
<221> NAME/KEY: misc_feature
<222> LOCATION: (33)..(40)
<223> OTHER INFORMATION: n may be A, T, G or C.

<400> SEQUENCE: 2
gccttgccag cacgctcagg ccttgcannn cgnnnnnnnn tcctggcttt aattttactg      60
gtacagt                                                               67

<210> SEQ ID NO 3
<211> LENGTH: 23
<212> TYPE: DNA
<213> ORGANISM: Artificial Sequence
<220> FEATURE:
<223> OTHER INFORMATION: Laboratory synthesized sequence

<400> SEQUENCE: 3
gagagacagg ctaatttttt agg                                              23

<210> SEQ ID NO 4
<211> LENGTH: 20
<212> TYPE: DNA
<213> ORGANISM: Artificial Sequence
<220> FEATURE:
<223> OTHER INFORMATION: Laboratory synthesized sequence

<400> SEQUENCE: 4
atagacaagg aactgtatcc                                                  20

<210> SEQ ID NO 5
<211> LENGTH: 21
<212> TYPE: DNA
<213> ORGANISM: Artificial Sequence
<220> FEATURE:
<223> OTHER INFORMATION: Laboratory synthesized sequence

<400> SEQUENCE: 5
gccttgccag cacgctcagg c                                                21

<210> SEQ ID NO 6
<211> LENGTH: 21
<212> TYPE: DNA
<213> ORGANISM: Artificial Sequence
<220> FEATURE:
<223> OTHER INFORMATION: Laboratory synthesized sequence

<400> SEQUENCE: 6
ccagcacgct caggccttgc a                                                21
```

METHODS AND USES FOR MOLECULAR TAGS

CROSS REFERENCE TO RELATED APPLICATIONS

This application is a § 371 U.S. National Stage of International Application PCT/US2013/027891, filed Feb. 27, 2013, which claims the benefit of U.S. Provisional Appn. No. 61/603,909, filed Feb. 27, 2012, Jabara et al., entitled "Methods and Uses for Molecular Tags", which are hereby incorporated by reference in their entireties.

STATEMENT REGARDING FEDERALLY SPONSORED RESEARCH OR DEVELOPMENT

This invention was made with government support under Grant No. AI044667 awarded by the U.S. National Institutes of Health (NIH). The government has certain rights in the invention.

FIELD OF THE INVENTION

The present invention relates generally to molecular tags and more specifically to compositions comprising molecular tags and methods for using molecular tags in genetic analysis. Molecular tags may also be used in the identification of drug-resistant variants. Also provided are methods for using molecular tags to detect and correct PCR amplification errors and sequencing errors.

BACKGROUND OF THE INVENTION

Deep sequencing technologies allow extensive sampling of genetic populations. Limitations of these technologies, however, potentially bias this sampling, particularly when a PCR step precedes the sequencing protocol. Typically, an unknown number of templates are used in initiating the PCR amplification, and this can lead to unrecognized sequence resampling creating apparent homogeneity; also, PCR-mediated recombination can disrupt linkage, and differential amplification efficiency or templates entering at different PCR cycles can skew the frequency of alleles. Finally, misincorporation of nucleotides during PCR and errors during the sequencing protocol can inflate diversity.

SUMMARY OF THE INVENTION

Limitations to current techniques can be overcome by including a unique sequence tag in the initial primer such that each template receives a unique Primer ID. After sequencing, repeated identification of a Primer ID reveals sequence resampling. These resampled sequences are then used to create an accurate consensus sequence for each template, correcting for recombination, allelic skewing, misincorporation errors, and sequencing errors. The resulting population of consensus sequences directly represents the initial sampled templates. Use of these molecular tags, can detect and correct for PCR error and/or sequencing error.

This approach can also be used in genetic analysis. Use of molecular tags, such as the Primer ID, enables analysis of the distribution of sequence variation of a gene in a complex genetic population. With this approach, major and minor polymorphisms at coding and noncoding positions have been identified. In addition, dynamic genetic changes within the population during intermittent drug exposure can be observed, including the emergence of multiple resistant alleles. The methods disclosed herein provide an unprecedented view of a complex genetic population in the absence of PCR resampling, PCR biases, and sequencing error.

Methods and uses for molecular tags are disclosed. Each copy of a nucleic acid molecule randomly chooses from a non-depleting reservoir of diverse Primer IDs. Attachment of the Primer ID to the nucleic acid molecule prior to amplification and sequencing enables direct counting of nucleic acid molecules and increased accuracy in detecting genetic variants. Primer IDs may also be used for detection of drug-resistant variants. Lastly, Primer IDs may also be used for reducing and/or correcting PCR errors and/or sequencing errors.

Disclosed herein is a method for determining genetic diversity of a sample comprising: (a) providing a sample comprising a nucleic acid template molecule; (b) attaching a primer comprising a Primer ID to each nucleic acid template molecule to be analyzed to generate a tagged nucleic acid template, wherein each tagged nucleic acid template is attached to a unique Primer ID; (c) amplifying the tagged nucleic acid template to produce tagged amplicons; and (d) detecting the tagged amplicons, thereby determining genetic diversity of a sample.

Further provided is a method for detecting genetic variants comprising: (a) providing a sample comprising a nucleic acid template molecule; (b) attaching a primer comprising a Primer ID to each nucleic acid template molecule to be analyzed to generate a tagged nucleic acid template, wherein each tagged nucleic acid template is attached to a unique Primer ID; (c) amplifying the tagged nucleic acid template to produce tagged amplicons; and (d) detecting the tagged amplicons, thereby detecting genetic variants.

Also provided herein is a method for determining or screening for drug-resistant variants comprising: (a) providing a sample comprising a nucleic acid template molecule; (b) attaching a primer comprising a Primer ID to each nucleic acid template molecule to be analyzed to generate a tagged nucleic acid template, wherein each tagged nucleic acid template is attached to a unique Primer ID; (c) amplifying the tagged nucleic acid template to produce tagged amplicons; and (d) detecting the tagged amplicons, thereby determining or screening for drug-resistant variants.

Further disclosed herein is a method for determining PCR resampling in an amplification reaction comprising: (a) providing a sample comprising a nucleic acid template molecule; (b) attaching a primer comprising a Primer ID to each nucleic acid template molecule to be analyzed to generate a tagged nucleic acid template, wherein each tagged nucleic acid template is attached to a unique Primer ID; (c) amplifying the tagged nucleic acid template to produce tagged amplicons; and (d) detecting the tagged amplicons, thereby determining PCR resampling in an amplification reaction.

Further disclosed herein is a method for determining PCR error and/or sequencing error comprising: (a) providing a sample comprising a nucleic acid template molecule; (b) attaching a primer comprising a Primer ID to each nucleic acid template molecule to be analyzed to generate a tagged nucleic acid template, wherein each tagged nucleic acid template is attached to a unique Primer ID; (c) amplifying the tagged nucleic acid template to produce tagged amplicons; and (d) detecting the tagged amplicons, thereby determining PCR error and/or sequencing error. In some embodiments, determining the PCR error and/or sequencing error comprises determining fidelity of a polymerase. In some embodiments, determining the PCR error and/or sequencing error comprises determining accuracy of oligonucleotides synthesized in vitro.

Further disclosed herein is a method for correcting PCR error and/or sequencing error comprising: (a) providing a sample comprising a nucleic acid template molecule; (b) attaching a primer comprising a Primer ID to each nucleic acid template molecule to be analyzed to generate a tagged nucleic acid template, wherein each tagged nucleic acid template is attached to a unique Primer ID; (c) amplifying the tagged nucleic acid template to produce tagged amplicons; and (d) detecting the tagged amplicons, thereby correcting PCR error and/or sequencing error.

In some embodiments, the Primer ID comprises a degenerate sequence. In some embodiments, the Primer ID comprises a semi-degenerate sequence. In some embodiments, the Primer ID comprises a mixed sequence. In some embodiments, the Primer ID comprises an ambiguous sequence. In some embodiments, the Primer ID comprises a wobble sequence. In some embodiments, the Primer ID comprises a random sequence. In some embodiments, the Primer ID comprises a predetermined sequence.

In some embodiments, the Primer ID is attached to the template by ligation. In some embodiments, the Primer ID is attached to the template by hybridization. In some embodiments, the Primer ID is attached to the template through PCR. In some embodiments, at least one template molecule is analyzed. In some embodiments, at least two different template molecules are analyzed. In some embodiments, detecting the tagged amplicons comprises sequencing the tagged amplicons. Sequencing of the tagged amplicons may occur by a variety of methods, including, but not limited to the Maxam-Gilbert sequencing method, the Sanger dideoxy sequencing method, dye-terminator sequencing method, pyrosequencing, multiple-primer DNA sequencing, shotgun sequencing, and primer walking. In some embodiments, sequencing comprises pyrosequencing.

In some embodiments, detecting the tagged amplicons further comprises counting a number of different Primer IDs associated with the tagged amplicons, wherein the number of different Primer IDs associated with the tagged amplicons reflects the number of templates sampled. In some embodiments, the method further comprises forming a consensus sequence for tagged amplicons comprising the same Primer ID.

In some embodiments, the nucleic acid template comprises a DNA template. In some embodiments, the nucleic acid template comprises an RNA template.

In some embodiments, amplifying comprises a PCR-based method. In some embodiments, the PCR-based method comprises PCR. In some embodiments, the PCR-based method comprises quantitative PCR. In some embodiments, the PCR-based method comprises emulsion PCR. In some embodiments, the PCR-based method comprises droplet PCR. In some embodiments, the PCR-based method comprises hot start PCR. In some embodiments, the PCR-based method comprises in situ PCR. In some embodiments, the PCR-based method comprises inverse PCR. In some embodiments, the PCR-based method comprises multiplex PCR. In some embodiments, the PCR-based method comprises Variable Number of Tandem Repeats (VNTR) PCR. In some embodiments, the PCR-based method comprises asymmetric PCR. In some embodiments, the PCR-based method comprises long PCR. In some embodiments, the PCR-based method comprises nested PCR. In some embodiments, the PCR-based method comprises hemi-nested PCR. In some embodiments, the PCR-based method comprises touchdown PCR. In some embodiments, the PCR-based method comprises assembly PCR. In some embodiments, the PCR-based method comprises colony PCR.

In some embodiments, amplifying comprises a non-PCR-based method. In some embodiments, the non-PCR-based method comprises multiple displacement amplification (MDA). In some embodiments, the non-PCR-based method comprises transcription-mediated amplification (TMA). In some embodiments, the non-PCR-based method comprises nucleic acid sequence-based amplification (NASBA). In some embodiments, the non-PCR-based method comprises strand displacement amplification (SDA). In some embodiments, the non-PCR-based method comprises real-time SDA. In some embodiments, the non-PCR-based method comprises rolling circle amplification. In some embodiments, the non-PCR-based method comprises circle-to-circle amplification.

BRIEF DESCRIPTION OF THE DRAWINGS

The skilled artisan will understand that the drawings described below are for illustration purposes only. The drawings are not intended to limit the scope of the present teachings in any way.

FIG. 1A shows an example primer comprising a Primer ID and Barcode.

FIG. 1B shows the use of a primer comprising a Primer ID and Barcode to detect and correct PCR biases and sequencing error (SEQ ID No. 1).

FIG. 1C shows the creation of a consensus sequence. In particular, FIG. 1A-1C show tagging viral RNA templates with a Primer ID before PCR amplification and sequencing allows for direct removal of artifactual errors and identifies resampling. FIG. 1A shows a primer that was designed to bind downstream of the protease coding domain. In the 5' tail of the primer, a degenerate string of eight nucleotides created a Primer ID, allowing for 65,536 unique combinations. An a priori selected three nucleotide barcode was designed for the sample ID. Finally, a heterologous string of nucleotides with low affinity to the HIV-1 genome was included in the far 5' end for use as the priming site in the PCR amplification. (FIG. 1B) PCR biases and sequencing error are introduced during amplification and sequencing of viral templates. Repetitive identification of the barcode and Primer ID allow for tracking of each templating event from a single tagged cDNA. As errors are minor components within the Primer ID population, forming a consensus sequence directly removes them, and corrects for PCR resampling. (FIG. 1C) HIV-1 RNA templates isolated from plasma samples from two pre- and one post-intermittent ritonavir drug therapy were tagged, amplified, and deep sequenced. Tagged sequences containing full-length protease were used to create a population of consensus sequences when at least three sequences contained an identical barcode and Primer ID.

FIG. 6B shows the number of consensus sequences containing an ambiguity as a function of extent of resampling. All three time points were combined. Dark gray bars represent consensus sequences without an ambiguity, and light gray bars represent consensus sequences with an ambiguity. There is a discernible pattern of an increased number of ambiguities going out to 22 reads/consensus sequence for those consensus sequences created from an even number of reads, the result of having a tie between two different sequences at one position. However, this represents only a small fraction of the total reads (5.4%). The amino acid position with the highest ambiguity total was used per Primer ID subpopulation.

FIG. 8A shows the frequency of major and minor unique pro gene sequences. Gray colors represent pro gene sequences present between 2.5 and 0.5% in frequency. Black represents the sum of all pro gene sequences individually present at <0.5%. FIG. 8B shows SNP distribution of the most abundant pro gene sequences (>2.5%), with the shaded dots on the right indicating the corresponding sequences identified in the pie chart (FIG. 8A). FIG. 8C shows SNP distribution of variants present between 2.5 and 0.5%, the same sequences indicated in panel FIG. 8A with the gray bar. The line at the bottom indicated by the black circle represents the sum of all variants <0.5% in frequency for the sequences shown in black in the pie chart (FIG. 8A).

FIG. 9A-9F shows the major and minor unique pro gene sequences in the major resistant populations V82A, L90M, and I84V. (FIG. 9A) Frequency of different unique pro gene sequences carrying the V82A mutation at high frequency (colored >2.5%) and low frequency (<2.5%, black and with the abundance pooled). (FIG. 9B) Highlighter plot showing the sequence changes from the consensus sequence for the major (>2.5%) pro gene variants carrying the V82A mutation. The V82A substitution is indicated by the nucleotide change at position 245 shown in light gray. (FIG. 9C) Frequency of different unique pro gene sequences carrying the L90M mutation at high frequency (colored >2.5%) and low frequency (<2.5%, black and with the abundance pooled). (FIG. 9D) Highlighter plot showing the sequence changes from the consensus sequence for the major (>2.5%) pro gene variants carrying the L90M mutation. The L90M substitution is indicated by the nucleotide change at position 268 shown in gray. (FIG. 9E) Frequency of different unique pro gene sequences carrying the I84V mutation at high frequency (colored >2.5%) and low frequency (<2.5%, black and with the abundance pooled). (FIG. 9F) Highlighter plot showing the sequence changes from the consensus sequence for the major (>2.5%) pro gene variants carrying the I84V mutation. The I84V substitution is indicated by the nucleotide change at position 250 shown in gray.

FIG. 13B shows the summary of resolved sequences. Total sequences are the number of sequences containing full-length protease with the tagging primer. Within a sample, when three or more sequences contained an identical Primer ID, a consensus sequence was generated.

Figure 2A:
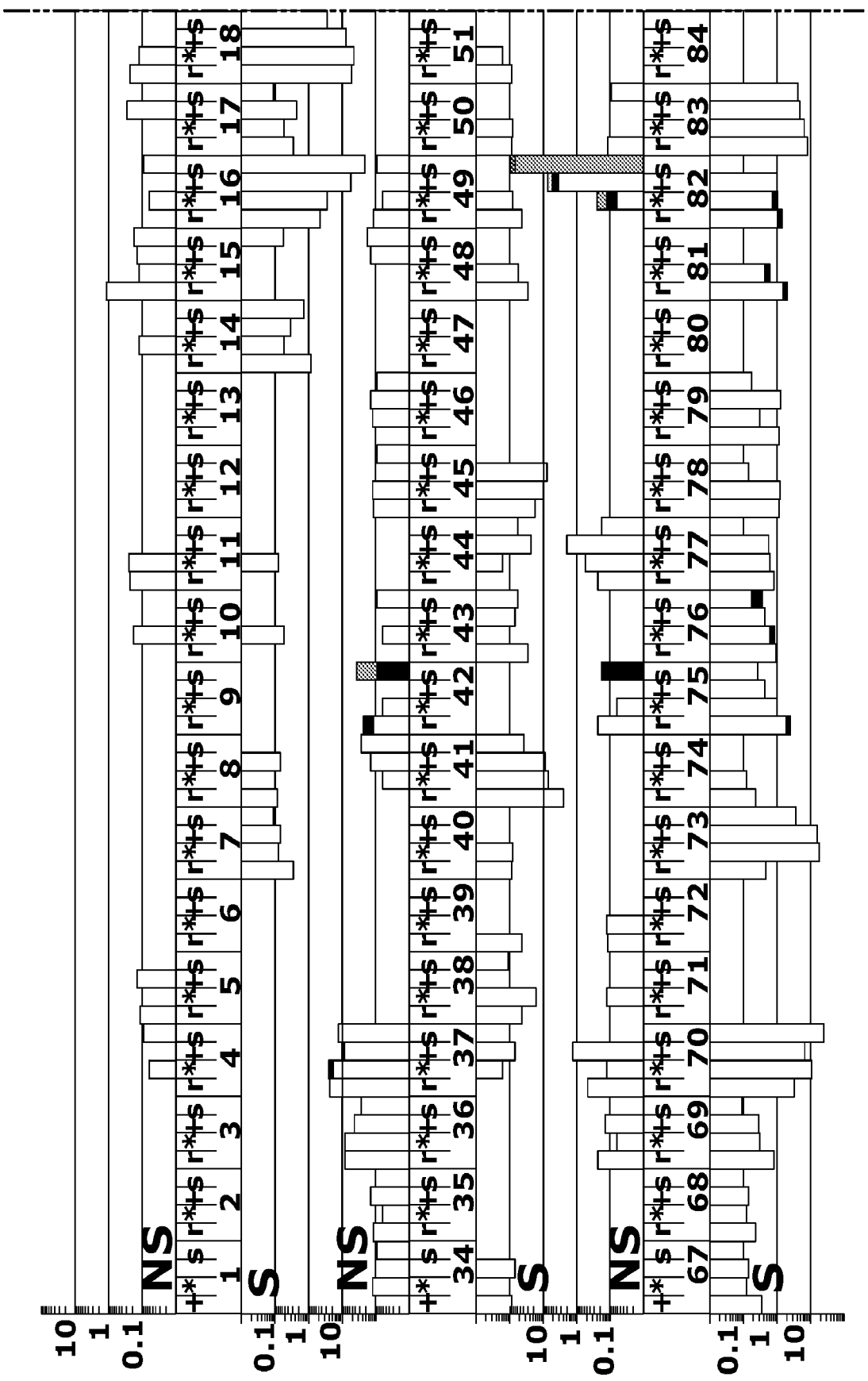
FIG. 2A-2B shows the frequency of codon variation across all 99 positions in protease over three time points. Within a codon position, the first two bars represent untreated time points 1 and 2, respectively. Bars 3 and 4 are the third time point split based on the presence or absence of the resistance mutations to ritonavir. Bar 3 is the population of susceptible genotypes (defined as not V82A, I84V, or L90M), and bar 4 is the major resistant variant, V82A, population. Upward facing bars are nonsynonymous changes (scale in regular typeface), and downward facing bars are synonymous changes (scale in bolded typeface). Within a codon position, different shading represents different SNPs.

Table 1. Frequency of nonconsensus codons per position
Table 2. Summary of nucleotide variation in sampled time points

DETAILED DESCRIPTION OF THE INVENTION

Disclosed herein are methods, kits, and systems for analyzing one or more nucleic acid molecules in a sample. Generally, the method comprises (a) attaching a Primer ID to a nucleic acid molecule or fragment thereof to produce a tagged nucleic acid; and (b) detecting the tagged nucleic acid molecule or a derivative or product thereof.

Attachment of the Primer ID to the nucleic acid molecule may occur by any method known in the art. For example, attachment of the Primer ID may comprise ligation. Ligation may comprise blunt end ligation. Alternatively, ligation comprises sticky end ligation. Alternatively, or additionally, attachment of the Primer ID may comprise primer extension. Attachment of the Primer ID to the nucleic acid molecule may comprise transcription or reverse transcription. Attachment of the Primer ID to the nucleic acid molecule may comprise one or more end-repair techniques of the ends of the nucleic acid molecule.

The method may further comprise, prior to the detecting step, amplifying the tagged nucleic acid molecule to produce one or more tagged amplicons, wherein detecting comprises detecting the tagged amplicons. Amplification of the tagged amplicons may comprise any method known in the art. For example, amplification may comprise a PCR based amplification method. Alternatively, or additionally, amplification may comprise a non-PCR based amplification method.

The method may further comprise, prior to the attaching step, fragmenting a nucleic acid molecule to produce nucleic acid fragments, wherein the Primer IDs are attached to the nucleic acid fragments. Fragmenting the nucleic acid molecule may occur by any method known in the art. For example, fragmenting the nucleic acid molecule may comprise shearing. Shearing may comprise mechanical shearing. Fragmenting may comprise sonicating the sample. Alternatively, fragmenting may comprise one or more restriction enzymes. The one or more restriction enzymes may be a restriction endonuclease.

Detection of the tagged nucleic acid molecule may comprise any method known in the art. Detection of the tagged nucleic acid molecule may comprise hybridization, sequencing, capture of the tagged nucleic acid molecule, electrophoresis, luminescence, chemiluminescence, or any combination thereof. Detection may comprise detection of the Primer ID portion of the tagged nucleic acid molecule. The Primer ID may comprise a detectable label (e.g., fluorophore, dye, bead, antigen, antibody, peptide, etc). Detection of the tagged nucleic acid molecule may comprise hybridization of the tagged nucleic acid molecule to a solid support (e.g., array, bead, plate).

The method may further comprise detecting one or more genetic variants based on the detection of the tagged nucleic acid molecule. For example, genetic variants may be detected by sequencing the tagged nucleic acid molecule. Sequences with the same Primer ID can be grouped together to form a Primer ID family. A genetic variant can be detected when at least 50% of the nucleic acid molecules in the Primer ID family contain the same nucleotide sequence variation. When less than 105 of the nucleic acid molecules in the Primer ID family contain the same nucleotide sequence variation, then the nucleotide sequence variation can be due to sequencing and/or amplification error.

The method may further comprise determining the amplification bias of an amplification reaction based on the detection of the tagged nucleic acid molecules. Amplification bias or PCR resampling can be used interchangeable and may refer to the unequal amplification of nucleic acid templates. Amplification bias may result in a skewing of the distribution of PCR products (e.g., amplicons). Amplification bias may be due to differences in the amplification efficiency of two or more nucleic acid templates. Alternatively, or additionally, amplification bias may be due to inhibition of amplification of a nucleic acid template. Determining the amplification bias may be based on comparison of two or more ratios, wherein comparison of the two or more ratios comprises comparing a first ratio of the quantification of different Primer IDs associated with two or more types of nucleic acid molecules to a second ratio of the quantification of the total number of amplicons of two or more types of nucleic acid molecules. The first ratio may be based on the amount of different Primer IDs associated with a first type of nucleic acid molecule and the amount of different Primer IDs associated with a second type of nucleic acid molecule. The second ratio may be based on the number of total amplicons associated with the first type of nucleic acid molecule and the number of total amplicons associated with the second type of nucleic acid molecule. In some instances, the difference in the first ratio and the second ratio can reveal amplification bias.

The method may further comprise determining the amplification efficiency of a nucleic acid molecule based on detection of the tagged nucleic acid molecule. Determining the amplification efficiency may comprise quantifying the number of different Primer IDs associated with the nucleic acid molecule. The method may further comprise comparing the number different Primer IDs associated with the nucleic acid molecule to the number of different Primer IDs associated with a nucleic acid control.

Reference will now be made in detail to exemplary embodiments of the invention. While the invention will be described in conjunction with the exemplary embodiments, it will be understood that they are not intended to limit the invention to these embodiments. On the contrary, the invention is intended to cover alternatives, modifications and equivalents, which may be included within the spirit and scope of the invention.

The invention has many preferred embodiments and relies on many patents, applications and other references for details known to those of the art. Therefore, when a patent, application, or other reference, such as a printed publication, is cited or repeated below, it should be understood that it is incorporated by reference in its entirety for all purposes and particularly for the proposition that is recited.

As used in this application, the singular form "a," "an," and "the" include plural references unless the context clearly dictates otherwise. For example, the term "an agent" includes a plurality of agents, including mixtures thereof.

An individual is not limited to a human being, but may also be other organisms including, but not limited to, mammals, plants, bacteria, cells derived from any of the above, viruses or virally-infected cells.

Throughout this disclosure, various aspects of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Suitable samples for analysis may be derived from a variety of sources. Biological samples may be of any biological tissue or fluid or cells from any organism. Frequently the sample will be a "clinical sample" which is a sample derived from a patient. Clinical samples provide a rich source of information regarding the various states of gene expression and copy number. Typical clinical samples include, but are not limited to, sputum, blood, tissue or fine needle biopsy samples, urine, peritoneal fluid, and pleural fluid, or cells therefrom. Biological samples may also include sections of tissues, such as frozen sections or formalin-fixed sections taken for histological purposes, which may include formalin-fixed, paraffin embedded (FFPE) samples and samples derived therefrom. FFPE samples are a particularly important source for study of archived tissue as they can nucleic acids can be recovered from these samples even after long term storage of the samples at room temperature. See, for example, Specht et al. *Am J. Path.* (2001), 158(2):419-429. Nucleic acids isolated from fresh-frozen samples may also be analyzed using the disclosed methods.

The practice of the present invention may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as *Genome Analysis: A Laboratory Manual Series (Vols. I-IV), Using Antibodies: A Laboratory Manual, Cells: A Laboratory Manual, PCR Primer: A Laboratory Manual,* and *Molecular Cloning: A Laboratory Manual* (all from Cold Spring Harbor Laboratory Press), Gait, "*Oligonucleotide Synthesis: A Practical Approach*" 1984, *IRL Press,* London, Nelson and Cox (2000), Lehninger et al., (2008) *Principles of Biochemistry* 5th Ed., W.H. Freeman Pub., New York, N.Y. and Berg et al. (2006) *Biochemistry, 6$^{th}$ Ed.,* W.H. Freeman Pub., New York, N.Y., all of which are herein incorporated in their entirety by reference for all purposes.

The present invention can employ solid substrates, including arrays in some preferred embodiments. Methods and techniques applicable to polymer (including protein) array synthesis have been described in U.S. Patent Pub. No. 20050074787, WO 00/58516, U.S. Pat. Nos. 5,143,854, 5,242,974, 5,252,743, 5,324,633, 5,384,261, 5,405,783, 5,424,186, 5,451,683, 5,482,867, 5,491,074, 5,527,681, 5,550,215, 5,571,639, 5,578,832, 5,593,839, 5,599,695, 5,624,711, 5,631,734, 5,795,716, 5,831,070, 5,837,832, 5,856,101, 5,858,659, 5,936,324, 5,968,740, 5,974,164, 5,981,185, 5,981,956, 6,025,601, 6,033,860, 6,040,193, 6,090,555, 6,136,269, 6,269,846 and 6,428,752, in PCT Publication No. WO 99/36760 and WO 01/58593, which are all incorporated herein by reference in their entirety for all purposes. Patents that describe synthesis techniques in specific embodiments include U.S. Pat. Nos. 5,412,087, 6,147, 205, 6,262,216, 6,310,189, 5,889,165, and 5,959,098. Nucleic acid arrays are described in many of the above patents, but many of the same techniques may be applied to polypeptide arrays.

The present invention also contemplates many uses for polymers attached to solid substrates. These uses include gene expression monitoring, transcript profiling, library screening, genotyping, epigenetic analysis, methylation pattern analysis, tumor typing, pharmacogenomics, agrigenetics, pathogen profiling and detection and diagnostics. Gene expression monitoring and profiling methods have been shown in U.S. Pat. Nos. 5,800,992, 6,013,449, 6,020,135, 6,033,860, 6,040,138, 6,177,248 and 6,309,822. Genotyping and uses therefore are shown in U.S. Patent Publication Nos. 20030036069 and 20070065816 and U.S. Pat. Nos. 5,856, 092, 6,300,063, 5,858,659, 6,284,460, 6,361,947, 6,368,799 and 6,333,179. Other uses are embodied in U.S. Pat. Nos. 5,871,928, 5,902,723, 6,045,996, 5,541,061, and 6,197,506.

The present invention also contemplates sample preparation methods in certain embodiments. Prior to or concurrent with analysis, the sample may be amplified by a variety of mechanisms. In some aspects nucleic acid amplification methods such as PCR may be combined with the disclosed methods and systems. See, for example, *PCR Technology: Principles and Applications for DNA Amplification* (Ed. H.

A. Erlich, Freeman Press, NY, NY, 1992); *PCR Protocols: A Guide to Methods and Applications* (Eds. Innis, et al., Academic Press, San Diego, Calif., 1990); Mattila et al., *Nucleic Acids Res.* 19, 4967 (1991); Eckert et al., *PCR Methods and Applications* 1, 17 (1991); PCR (Eds. McPherson et al., IRL Press, Oxford); and U.S. Pat. Nos. 4,683,202, 4,683,195, 4,800,159, 4,965,188, and 5,333,675, each of which is incorporated herein by reference in their entireties for all purposes. Additional methods of sample preparation and techniques for reducing the complexity of a nucleic sample are described in Dong et al., *Genome Research* 11, 1418 (2001), in U.S. Pat. No. 6,300,070 (amplification on an array), U.S. Pat. Nos. 6,361,947, 6,391,592, 6,872,529 and 6,458,530 and U.S. Patent Pub. Nos. 20030096235, 20030082543, 20030039069, 20050079536, 20040072217, 20050142577, 20050233354, 20050227244, 20050208555, 20050074799, 20050042654, and 20040067493, which are each incorporated herein by reference in their entireties.

Many of the methods and systems disclosed herein utilize enzyme activities. Enzymes and related methods of use in molecular biology that may be used in combination with the disclosed methods and systems are reviewed, for example, in Rittie and Perbal, *J. Cell Commun. Signal.* (2008) 2:25-45, incorporated herein by reference in its entirety. A variety of enzymes are well known, have been characterized and many are commercially available from one or more supplier. Exemplary enzymes include DNA dependent DNA polymerases (such as those shown in Table 1 of Rittie and Perbal), RNA dependent DNA polymerase (see Table 2 of Rittie and Perbal), RNA polymerases (such as T7 and SP6), ligases (see Table 3 of Rittie and Perbal), enzymes for phosphate transfer and removal (see Table 4 of Rittie and Perbal), nucleases (see Table 5 of Rittie and Perbal), and methylases.

Other methods of genome analysis and complexity reduction include, for example, AFLP, see U.S. Pat. No. 6,045,994, which is incorporated herein by reference, and arbitrarily primed-PCR (AP-PCR) see McClelland and Welsh, in *PCR Primer: A laboratory Manual,* (1995) eds. C. Dieffenbach and G. Dveksler, Cold Spring Harbor Lab Press, for example, at p 203, which is incorporated herein by reference in its entirety.

Other suitable amplification methods include the ligase chain reaction (LCR) (for example, Wu and Wallace, *Genomics* 4, 560 (1989), Landegren et al., *Science* 241, 1077 (1988) and Barringer et al. *Gene* 89:117 (1990)), transcription amplification (Kwoh et al., *Proc. Natl. Acad. Sci. USA* 86, 1173 (1989) and WO88/10315), self-sustained sequence replication (Guatelli et al., *Proc. Nat. Acad. Sci. USA,* 87, 1874 (1990) and WO90/06995), selective amplification of target polynucleotide sequences (U.S. Pat. No. 6,410,276), consensus sequence primed polymerase chain reaction (CP-PCR) (U.S. Pat. No. 4,437,975), arbitrarily primed polymerase chain reaction (AP-PCR) (U.S. Pat. Nos. 5,413,909, 5,861,245), rolling circle amplification (RCA) (for example, Fire and Xu, PNAS 92:4641 (1995) and Liu et al., *J. Am. Chem. Soc.* 118:1587 (1996)) and U.S. Pat. No. 5,648,245, strand displacement amplification (see Lasken and Egholm, *Trends Biotechnol.* 2003 21(12):531-5; Barker et al. *Genome Res.* 2004 May; 14(5):901-7; Dean et al. *Proc Natl Acad Sci USA.* 2002; 99(8):5261-6; Walker et al. 1992, Nucleic Acids Res. 20(7):1691-6, 1992 and Paez, et al. *Nucleic Acids Res.* 2004; 32(9):e71), Qbeta Replicase, described in PCT Patent Application No. PCT/US87/00880 and nucleic acid based sequence amplification (NABSA). (See, U.S. Pat. Nos. 5,409,818, 5,554,517, and 6,063,603, each of which is incorporated herein by reference), Other amplification methods that may be used are described in, U.S. Pat. Nos. 6,582,938, 5,242,794, 5,494,810, 4,988,617, and US Pub. No. 20030143599 each of which is incorporated herein by reference. DNA may also be amplified by multiplex locus-specific PCR or using Primer ID-ligation and single primer PCR (See Kinzler and Vogelstein, NAR (1989) 17:3645-53. Other available methods of amplification, such as balanced PCR (Makrigiorgos, et al. (2002), *Nat Biotechnol*, Vol. 20, pp. 936-9), may also be used.

Molecular inversion probes ("MIPs") may also be used for amplification of selected targets. MIPs may be generated so that the ends of the pre-circle probe are complementary to regions that flank the region to be amplified. The gap can be closed by extension of the end of the probe so that the complement of the target is incorporated into the MIP prior to ligation of the ends to form a closed circle. The closed circle can be amplified and detected by sequencing or hybridization as previously disclosed in Hardenbol et al., *Genome Res.* 15:269-275 (2005) and in U.S. Pat. No. 6,858,412.

Methods of ligation will be known to those of skill in the art and are described, for example in Sambrook et al. (2001) and the New England BioLabs catalog both of which are incorporated herein by reference for all purposes. Methods include using T4 DNA Ligase which catalyzes the formation of a phosphodiester bond between juxtaposed 5' phosphate and 3' hydroxyl termini in duplex DNA or RNA with blunt and sticky ends; Taq DNA Ligase which catalyzes the formation of a phosphodiester bond between juxtaposed 5' phosphate and 3' hydroxyl termini of two adjacent oligonucleotides which are hybridized to a complementary target DNA; *E. coli* DNA ligase which catalyzes the formation of a phosphodiester bond between juxtaposed 5'-phosphate and 3'-hydroxyl termini in duplex DNA containing cohesive ends; and T4 RNA ligase which catalyzes ligation of a 5' phosphoryl-terminated nucleic acid donor to a 3' hydroxyl-terminated nucleic acid acceptor through the formation of a 3'-5' phosphodiester bond, substrates include single-stranded RNA and DNA as well as dinucleoside pyrophosphates; or any other methods described in the art. Fragmented DNA may be treated with one or more enzymes, for example, an endonuclease, prior to ligation of Primer IDs to one or both ends to facilitate ligation by generating ends that are compatible with ligation.

Methods for ligating primers comprising Primer IDs to fragments of nucleic acid are well known. Primers may be double-stranded, single-stranded or partially single-stranded. In some aspects, primers are formed from two oligonucleotides that have a region of complementarity, for example, about 10 to 30, or about 15 to 40 bases of perfect complementarity, so that when the two oligonucleotides are hybridized together they form a double stranded region. Optionally, either or both of the oligonucleotides may have a region that is not complementary to the other oligonucleotide and forms a single stranded overhang at one or both ends of the primer. Single-stranded overhangs may preferably by about 1 to about 8 bases, and most preferably about 2 to about 4. The overhang may be complementary to the overhang created by cleavage with a restriction enzyme to facilitate "sticky-end" ligation. Primers may include other features, such as primer binding sites and restriction sites. In some aspects the restriction site may be for a Type IIS restriction enzyme or another enzyme that cuts outside of its recognition sequence, such as EcoP151 (see, Mucke et al. *J Mol Biol* 2001, 312(4):687-698 and U.S. Pat. No. 5,710,000 which is incorporated herein by reference in its entirety).

Methods for using mapping arrays see, for example, Applications of microarrays for SNP genotyping have been described in e.g., U.S. Pat. Nos. 6,300,063, 6,361,947, 6,368,799 and US Patent Publication Nos. 20040067493, 20030232353, 20030186279, 20050260628, 20070065816 and 20030186280, and Kennedy et al., *Nat. Biotech.* 21:1233-1237 (2003), Matsuzaki et al., *Genome Res.* 14:414-425 (2004), Matsuzaki et al., *Nat. Meth.* 1:109-111 (2004) and U.S. Patent Pub. Nos. 20040146890 and 20050042654, each incorporated herein by reference. Fixed content mapping arrays are available from Affymetrix, for example, the SNP 6.0 array and the AXIOM® array system. Selected panels of SNPs and markers (e.g. copy number markers) can also be interrogated using a panel of locus specific probes in combination with a universal array as described in Hardenbol et al., *Genome Res.* 15:269-275 (2005) and in U.S. Pat. No. 6,858,412. Universal tag arrays and reagent kits for performing such locus specific genotyping using panels of custom molecular inversion probes (MIPs) are available from Affymetrix.

Methods for analyzing chromosomal copy number using mapping arrays are disclosed, for example, in Bignell et al., *Genome Res.* 14:287-95 (2004), Lieberfarb, et al., *Cancer Res.* 63:4781-4785 (2003), Zhao et al., *Cancer Res.* 64:3060-71 (2004), Huang et al., *Hum Genomics* 1:287-299 (2004), Nannya et al., *Cancer Res.* 65:6071-6079 (2005), Slater et al., *Am. J. Hum. Genet.* 77:709-726 (2005) and Ishikawa et al., *Biochem. and Biophys. Res. Comm.*, 333: 1309-1314 (2005). Computer implemented methods for estimation of copy number based on hybridization intensity are disclosed in U.S. Patent Pub. Nos. 20040157243, 20050064476, 20050130217, 20060035258, 20060134674 and 20060194243.

Methods for conducting polynucleotide hybridization assays have been well developed in the art. Hybridization assay procedures and conditions will vary depending on the application and are selected in accordance with known general binding methods, including those referred to in: Maniatis et al. *Molecular Cloning: A Laboratory Manual* ($2^{nd}$ Ed. Cold Spring Harbor, N. Y, 1989); Berger and Kimmel *Methods in Enzymology*, Vol. 152, *Guide to Molecular Cloning Techniques* (Academic Press, Inc., San Diego, Calif., 1987); Young and Davis, *P.N.A.S*, 80: 1194 (1983). Methods and apparatus for carrying out repeated and controlled hybridization reactions have been described in U.S. Pat. Nos. 5,871,928, 5,874,219, 6,045,996 and 6,386, 749, 6,391,623 each of which are incorporated herein by reference.

The present invention also contemplates signal detection of hybridization between ligands in certain preferred embodiments. See U.S. Pat. Nos. 5,143,854, 5,578,832, 5,631,734, 5,834,758, 5,936,324, 5,981,956, 6,025,601, 6,141,096, 6,185,030, 6,201,639, 6,218,803, and 6,225,625 in U.S. Patent Pub. No. 20040012676 and in PCT Application PCT/US99/06097 (published as WO99/47964), each of which also is hereby incorporated by reference in its entirety for all purposes.

Methods and apparatus for signal detection and processing of intensity data are disclosed in, for example, U.S. Pat. Nos. 5,143,854, 5,547,839, 5,578,832, 5,631,734, 5,800, 992, 5,834,758, 5,856,092, 5,902,723, 5,936,324, 5,981,956, 6,025,601, 6,090,555, 6,141,096, 6,185,030, 6,201,639; 6,218,803; and 6,225,625, in U.S. Patent Pub. Nos. 20040012676 and 20050059062 and in PCT Application PCT/US99/06097 (published as WO99/47964), each of which also is hereby incorporated by reference in its entirety for all purposes.

The practice of the present invention may also employ conventional biology methods, software and systems. Computer software products of the invention typically include computer readable medium having computer-executable instructions for performing the logic steps of the method of the invention. Suitable computer readable medium include floppy disk, CD-ROM/DVD/DVD-ROM, hard-disk drive, flash memory, ROM/RAM, magnetic tapes, etc. The computer-executable instructions may be written in a suitable computer language or combination of several languages. Basic computational biology methods are described in, for example, Setubal and Meidanis et al., *Introduction to Computational Biology Methods* (PWS Publishing Company, Boston, 1997); Salzberg, Searles, Kasif, (Ed.), *Computational Methods in Molecular Biology*, (Elsevier, Amsterdam, 1998); Rashidi and Buehler, *Bioinformatics Basics: Application in Biological Science and Medicine* (CRC Press, London, 2000) and Ouelette and Bzevanis *Bioinformatics: A Practical Guide for Analysis of Gene and Proteins* (Wiley & Sons, Inc., $2^{nd}$ ed., 2001). See also U.S. Pat. No. 6,420,108.

The present invention may also make use of various computer program products and software for a variety of purposes, such as probe design, management of data, analysis, and instrument operation. See, U.S. Pat. Nos. 5,593,839, 5,795,716, 5,733,729, 5,974,164, 6,066,454, 6,090,555, 6,185,561, 6,188,783, 6,223,127, 6,229,911 and 6,308,170. Computer methods related to genotyping using high density microarray analysis may also be used in the present methods, see, for example, US Patent Pub. Nos. 20050250151, 20050244883, 20050108197, 20050079536 and 20050042654. Additionally, the present disclosure may have preferred embodiments that include methods for providing genetic information over networks such as the Internet as shown in U.S. Patent Pub. Nos. 20030097222, 20020183936, 20030100995, 20030120432, 20040002818, 20040126840, and 20040049354.

An allele refers to one specific form of a genetic sequence (such as a gene) within a cell, an individual or within a population, the specific form differing from other forms of the same gene in the sequence of at least one, and frequently more than one, variant sites within the sequence of the gene. The sequences at these variant sites that differ between different alleles are termed "variances", "polymorphisms", or "mutations". At each autosomal specific chromosomal location or "locus" an individual possesses two alleles, one inherited from one parent and one from the other parent, for example one from the mother and one from the father. An individual is "heterozygous" at a locus if it has two different alleles at that locus. An individual is "homozygous" at a locus if it has two identical alleles at that locus.

The term "polymorphism" as used herein refers to the occurrence of two or more genetically determined alternative sequences or alleles in a population. A polymorphic marker or site is the locus at which divergence occurs. In some instances, the polymorphic markers occur at a frequency of less than 0.5%. In some instances, the polymorphic markers occur at a frequency of less than 1%. In some instances, the polymorphic markers occur at a frequency of less than 2%. In some instances, the polymorphic markers occur at a frequency of less than 5%. In some instances, the polymorphic markers occur at a frequency of greater than 1%. In some instances, the polymorphic markers occur at a frequency of greater than 5%. In some instances, the polymorphic markers occur at a frequency of greater than 10%. In some instances, the polymorphic markers occur at a frequency of greater than 20%. In some instances, the polymorphic markers occur at a frequency of greater than 30%. In some instances, preferred markers have at least two alleles, each occurring at frequency of greater than 1%, and more preferably greater than 10% or 20% in a selected population. In some instances, preferred polymorphic markers comprise viral or bacterial sequences and occur at a frequency of less than 5%, and more preferably, less than 1% in a selected population. A polymorphism may comprise one or more base changes, an insertion, a repeat, or a deletion of one or more bases. Copy number variants (CNVs), transversions and other rearrangements are also forms of genetic variation. Polymorphic markers include restriction fragment length polymorphisms, variable number of tandem repeats (VNTR's), hypervariable regions, minisatellites, dinucleotide repeats, trinucleotide repeats, tetranucleotide repeats, simple sequence repeats, and insertion elements such as Alu. The allelic form occurring most frequently in a selected population is sometimes referred to as the wildtype form. Diploid organisms may be homozygous or heterozygous for allelic forms. A diallelic polymorphism has two forms. A triallelic polymorphism has three forms. Single nucleotide polymorphisms (SNPs) are a form of polymorphisms. SNPs are a common type of human genetic variation and are useful in the performance of genome wide association studies (GWAS). GWAS may be used, for example for the analysis of biological pathways, see Wang and Hakonarson, Nat. Rev. Genet. 2010, 11:843-854.

The term genotyping refers to the determination of the genetic information an individual carries at one or more positions in the genome. For example, genotyping may comprise the determination of which allele or alleles an individual carries for a single SNP or the determination of which allele or alleles an individual carries for a plurality of SNPs or CNVs. A diploid individual may be homozygous for each of the two possible alleles (for example, AA or BB) or heterozygous (for example, AB). For additional information regarding genotyping and genome structure see, Color Atlas of Genetics, Ed. Passarge, Thieme, New York, N.Y. (2001), which is incorporated by reference.

Normal cells that are heterozygous at one or more loci may give rise to tumor cells that are homozygous at those loci. This loss of heterozygosity (LOH) may result from structural deletion of normal genes or loss of the chromosome carrying the normal gene, mitotic recombination between normal and mutant genes, followed by formation of daughter cells homozygous for deleted or inactivated (mutant) genes; or loss of the chromosome with the normal gene and duplication of the chromosome with the deleted or inactivated (mutant) gene. LOH may be copy neutral or may result from a deletion or amplification.

The term "array" as used herein refers to an intentionally created collection of molecules which can be prepared either synthetically or biosynthetically. The molecules in the array can be identical or different from each other. The array can assume a variety of formats, for example, libraries of soluble molecules; libraries of compounds tethered to resin beads, silica chips, microparticles, nanoparticles or other solid supports.

The term "complementary" as used herein refers to the hybridization or base pairing between nucleotides or nucleic acids, such as, for instance, between the two strands of a double stranded DNA molecule or between an oligonucleotide primer and a primer binding site on a single stranded nucleic acid to be sequenced or amplified. See, M. Kanehisa Nucleic Acids Res. 12:203 (1984), incorporated herein by reference.

The term "copy number variation" or "CNV" refers to differences in the copy number of genetic information. In many aspects it refers to differences in the per genome copy number of a genomic region. For example, in a diploid organism the expected copy number for autosomal genomic regions is 2 copies per genome. Such genomic regions should be present at 2 copies per cell. For a recent review see Zhang et al. *Annu. Rev. Genomics Hum. Genet.* 2009. 10:451-81. CNV is a source of genetic diversity in humans and can be associated with complex disorders and disease, for example, by altering gene dosage, gene disruption, or gene fusion. They can also represent benign polymorphic variants. CNVs can be large, for example, larger than 1 Mb, but many are smaller, for example between 100 bp and 1 Mb. More than 38,000 CNVs greater than 100 bp (and less than 3 Mb) have been reported in humans. Along with SNPs these CNVs account for a significant amount of phenotypic variation between individuals. In addition to having deleterious impacts, e.g. causing disease, they may also result in advantageous variation.

Digital PCR is a technique where a limiting dilution of the sample is made across a large number of separate PCR reactions so that most of the reactions have no template molecules and give a negative amplification result. Those reactions that are positive at the reaction endpoint are counted as individual template molecules present in the original sample in a 1 to 1 relationship. See Kalina et al. NAR 25:1999-2004 (1997) and Vogelstein and Kinzler, PNAS 96:9236-9241 (1999). This method is an absolute counting method where solutions are partitioned into containers until there is an average probability of one molecule per two containers or when, $P_0=(1-e^{-n/c})=\frac{1}{2}$; where n is the number of molecules and c is the number of containers, or n/c is 0.693. Quantitative partitioning is assumed, and the dynamic range is governed by the number of containers available for stochastic separation. The molecules are then detected by PCR and the number of positive containers is counted. Each successful amplification is counted as one molecule, independent of the actual amount of product. PCR-based techniques have the additional advantage of only counting molecules that can be amplified, e.g. that are relevant to the massively parallel PCR step in the sequencing workflow. Because digital PCR has single molecule sensitivity, only a few hundred library molecules are required for accurate quantification. Elimination of the quantification bottleneck reduces the sample input requirement from micrograms to nanograms or less, opening the way for minute and/or precious samples onto the next-generation sequencing platforms without the distorting effects of pre-amplification. Digital PCR has been used to quantify sequencing libraries to eliminate uncertainty associated with the construction and application of standard curves to PCR-based quantification and enable direct sequencing without titration runs. See White et al. *BMC Genomics* 10: 116 (2009). To vary dynamic range, microfabrication can be used to substantially increase the number of containers. See, Fan et al. *Am J Obstet Gynecol* 200, 543 el (May, 2009).

Similarly, in stochastic labeling, the same statistical conditions are met when $P_0=(1-e^{-n/m})=\frac{1}{2}$; where m is the number of Primer IDs, and one half of the Primer IDs will be used at least once when n/m=0.693. The dynamic range is governed by the number of Primer IDs used, and the number of Primer IDs can be easily increased to extend the dynamic range. The number of containers in digital PCR plays the same role as the number of Primer IDs in stochastic labeling and by substituting containers for Primer IDs identical statistical equations may be applied. Using the principles of physical separation, digital PCR stochastically expands identical molecules into physical space, whereas the principle governing stochastic labeling is identity based and expands identical molecules into identity space. See PCT Application PCT/US11/65291, which also is hereby incorporated by reference in its entirety for all purposes The term "hybridization" as used herein refers to the process in which two single-stranded polynucleotides bind non-covalently to form a stable double-stranded polynucleotide; triple-stranded hybridization is also theoretically possible. The resulting (usually) double-stranded polynucleotide is a "hybrid." The proportion of the population of polynucleotides that forms stable hybrids is referred to herein as the "degree of hybridization." Hybridizations may be performed under stringent conditions, for example, at a salt concentration of no more than 1 M and a temperature of at least 25° C. For example, conditions of 5×SSPE (750 mM NaCl, 50 mM Na Phosphate, 5 mM EDTA, pH 7.4) and a temperature of 25-30° C. are suitable for allele-specific probe hybridizations. For stringent conditions, see, for example, Sambrook, Fritsche and Maniatis. "Molecular Cloning A laboratory Manual" $2^{nd}$ Ed. Cold Spring Harbor Press (1989) which is hereby incorporated by reference in its entirety for all purposes above. In some aspects salt concentrations for hybridization are preferably between about 200 mM and about 1M or between about 200 mM and about 500 mM. Hybridization temperatures can be as low as 5° C., but are typically greater than 22° C., more typically greater than about 30° C., and preferably in excess of about 37° C. Longer fragments may require higher hybridization temperatures for specific hybridization. As other factors may affect the stringency of hybridization, including base composition and length of the complementary strands, presence of organic solvents and extent of base mismatching, the combination of parameters is more important than the absolute measure of any one alone.

The term "mRNA" or sometimes refer by "mRNA transcripts" as used herein, include, but not limited to premRNA transcript(s), transcript processing intermediates, mature mRNA(s) ready for translation and transcripts of the gene or genes, or nucleic acids derived from the mRNA transcript(s). Transcript processing may include splicing, editing and degradation. As used herein, a nucleic acid derived from an mRNA transcript refers to a nucleic acid for whose synthesis the mRNA transcript or a subsequence thereof has ultimately served as a template. Thus, a cDNA reverse transcribed from an mRNA, an RNA transcribed from that cDNA, a DNA amplified from the cDNA, an RNA transcribed from the amplified DNA, etc., are all derived from the mRNA transcript and detection of such derived products is indicative of the presence and/or abundance of the original transcript in a sample. Thus, mRNA derived samples include, but are not limited to, mRNA transcripts of the gene or genes, cDNA reverse transcribed from the mRNA, cRNA transcribed from the cDNA, DNA amplified from the genes, RNA transcribed from amplified DNA, and the like.

Other classes of RNAs are also expressed, including, for example, ribosomal RNA, snRNA, miRNA and siRNA. Recent evidence suggests that the human transcriptome contains many functional RNA transcripts that are not translated into proteins. These non-coding RNAs have been recognized as important to a more complete understanding of biology. Mature miRNAs are relatively small (21-23 nucleotides) RNA duplexes that act as translational repressors of protein expression. The guide strand of a miRNA interacts with proteins to form RNA-Induced Silencing Complexes (RISC) in the cell. These sequence-specific ribonucleoprotein complexes bind target mRNAs typically in the 3'UTR and can subsequently silence gene expression either through directed mRNA degradation or by simply sequestering the target mRNA in an ineffectual form (Lee et al., Cell (1993), 75: 843-854; Bartel, Cell (2009), 136: 215-233). It has been demonstrated that miRNA based regulation plays a significant role in routine cellular processes including metabolism (Esau et al, Cell Met. 2006, v. 3, p 87-98), development (Carthew et al., Cell 2009, v. 137, p. 273-282), and even apoptosis (Cheng et al, Nucl. Acids Res. 2005, v. 33, p 1290-1297). Further research has revealed that miRNAs play critical roles in diverse disease processes such as hepatitis C (Jopling et al., Science 2005, v. 309, p. 1577-1581), diabetes (Poy et al., Nature 2004, v. 432, p. 226-230), and most notably multiple cancer types (Hammond, Can. Chemo. Pharma. 2006 v. 58, s63-s68; Calin et al., Cancer Res. 2006, v. 66, p. 7390-7394) including leukemia (Calin et al., PNAS 2002, v. 101, p. 2999-3004) and glioma (Corsten et al., Cancer Res. 2007, v. 67, p. 8994-9000). Over one thousand miRNAs have now been identified in animals, but only a few individual miRNAs have been linked to specific functions. Methods of the invention disclosed herein can be used for tagging of relatively short regulatory non-coding RNAs, such as micro RNAs (miRNAs), Piwi-interacting RNAs (piRNAs), snoRNAs, snRNAs, moRNAs, PARs, sdRNAs, tel-sRNAs, crasiRNAs, and small interfering RNAs (siRNAs). Methods of the invention can also be used for tagging long non-coding RNAs (long ncRNAs), traditional non-coding tRNAs and ribosomal RNA (rRNA).

The term "nucleic acid" as used herein refers to a polymeric form of nucleotides of any length, either ribonucleotides, deoxyribonucleotides or peptide nucleic acids (PNAs), that comprise purine and pyrimidine bases, or other natural, chemically or biochemically modified, non-natural, or derivatized nucleotide bases. The backbone of the polynucleotide can comprise sugars and phosphate groups, as may typically be found in RNA or DNA, or modified or substituted sugar or phosphate groups. A polynucleotide may comprise modified nucleotides, such as methylated nucleotides and nucleotide analogs. The sequence of nucleotides may be interrupted by non-nucleotide components. Thus the terms nucleoside, nucleotide, deoxynucleoside and deoxynucleotide generally include analogs such as those described herein. These analogs are those molecules having some structural features in common with a naturally occurring nucleoside or nucleotide such that when incorporated into a nucleic acid or oligonucleoside sequence, they allow hybridization with a naturally occurring nucleic acid sequence in solution. Typically, these analogs are derived from naturally occurring nucleosides and nucleotides by replacing and/or modifying the base, the ribose or the phosphodiester moiety. The changes can be tailor made to stabilize or destabilize hybrid formation or enhance the specificity of hybridization with a complementary nucleic acid sequence as desired.

The term "oligonucleotide" or sometimes refer by "polynucleotide" as used herein refers to a nucleic acid ranging from at least 2, preferable at least 8, and more preferably at least 20 nucleotides in length or a compound that specifically hybridizes to a polynucleotide. Polynucleotides of the present invention include sequences of deoxyribonucleic acid (DNA) or ribonucleic acid (RNA) that may be isolated from natural sources, recombinantly produced or artificially synthesized and mimetics thereof. A further example of a polynucleotide of the present invention may include non natural analogs that may increase specificity of hybridization, for example, peptide nucleic acid (PNA) linkages and Locked Nucleic Acid (LNA) linkages. The LNA linkages are conformationally restricted nucleotide analogs that bind to complementary target with a higher melting temperature and greater mismatch discrimination. Other modifications that may be included in probes include: 2'OMe, 2'OAllyl, 2'O-propargyl, 2'O-alkyl, 2' fluoro, 2' arabino, 2' xylo, 2' fluoro arabino, phosphorothioate, phosphorodithioate, phosphoroamidates, 2'Amino, 5-alkyl-substituted pyrimidine, 5-halo-substituted pyrimidine, alkyl-substituted purine, halo-substituted purine, bicyclic nucleotides, 2'MOE, LNA-like molecules and derivatives thereof. The invention also encompasses situations in which there is a nontraditional base pairing such as Hoogsteen base pairing which has been identified in certain tRNA molecules and postulated to exist in a triple helix. "Polynucleotide" and "oligonucleotide" are used interchangeably in this application.

The term "primer" as used herein refers to a double-stranded, single-stranded, or partially single-stranded oligonucleotide. In some embodiments, primers are capable of acting as a point of initiation for template-directed nucleic acid synthesis under suitable conditions for example, buffer and temperature, in the presence of four different nucleoside triphosphates and an agent for polymerization, such as, for example, DNA or RNA polymerase or reverse transcriptase. The length of the primer, in any given case, depends on, for example, the intended use of the primer, and generally ranges from 15 to 100 nucleotides. Short primer molecules generally require cooler temperatures to form sufficiently stable hybrid complexes with the template. A primer need not reflect the exact sequence of the template but must be sufficiently complementary to hybridize with such template. The primer site is the area of the template to which a primer hybridizes. The primer pair is a set of primers including a 5' upstream primer that hybridizes with the 5' end of the sequence to be amplified and a 3' downstream primer that hybridizes with the complement of the 3' end of the sequence to be amplified. As used herein, the primer may comprise a target specific sequence and a Primer ID sequence. The primer may further comprise a barcode sequence. The barcode sequence may be used to identify the presence of a Primer ID sequence. The primer may also comprise a PCR priming sequence. The PCR priming sequence may be used to initiate amplification of a tagged nucleic acid molecule.

The term "probe" as used herein refers to a surface-immobilized molecule that can be recognized by a particular target. See U.S. Pat. No. 6,582,908 for an example of arrays having all possible combinations of probes with 10, 12, and more bases. Examples of probes that can be investigated by this invention include, but are not restricted to, agonists and antagonists for cell membrane receptors, toxins and venoms, viral epitopes, hormones (for example, opioid peptides, steroids, etc.), hormone receptors, peptides, enzymes, enzyme substrates, cofactors, drugs, lectins, sugars, oligonucleotides, nucleic acids, oligosaccharides, proteins, and monoclonal antibodies.

The term "solid support", "support", and "substrate" as used herein are used interchangeably and refer to a material or group of materials having a rigid or semi-rigid surface or surfaces. In many embodiments, at least one surface of the solid support will be substantially flat, although in some embodiments it may be desirable to physically separate synthesis regions for different compounds with, for example, wells, raised regions, pins, etched trenches, or the like. According to other embodiments, the solid support(s) will take the form of beads, resins, gels, microspheres, or other geometric configurations. See U.S. Pat. No. 5,744,305 and US Patent Pub. Nos. 20090149340 and 20080038559 for exemplary substrates.

The term "Primer ID" as used herein to refer to the information that is added to. Libraries of primer having a diversity of unique Primer IDs, for example about 1,000, about 5,000, about 10,000, about 100,000 or more than 100,000 may be used to uniquely identify occurrences of target species thereby marking each species with an identifier that can be used to distinguish between two otherwise identical or nearly identical targets. For example, each Primer ID may be a short string of nucleotides that can be attached to different copies of an mRNA, for example, a first Primer ID may be 5'GCATCTTC3' and a second may be 5'CAAGTAAC3'. Each has a unique identity that can be determined by determining the identity and order of the bases in the Primer ID.

Although nucleic acids are used throughout as a preferred embodiment of Primer ID, one of skill in the art will appreciate that a number of types of molecules or items that can be generated with the diversity needed may be used as Primer IDs. Primer IDs should be compounds, structures or elements that are amenable to at least one method of detection that allows for discrimination between different Primer IDs and should be associable in some means with the elements to be counted. For example, a pool of Primer IDs may be comprised of a collection of different semiconductor nanocrystals, metal compounds, peptides, antibodies, small molecules, isotopes, particles or structures having different shapes, colors, or diffraction patterns associated therewith or embedded therein, strings of numbers, random fragments of proteins or nucleic acids, or different isotopes (see, Abdelrahman, A. I. et al. *Journal of Analytical Atomic Spectrometry* 25 (3):260-268, 2010 for use of metal containing polystyrene beads as standards for mass cytometry, incorporated herein by reference). Pools of Primer IDs may be partitioned into distinct sets that can be attached to separate sample mixtures and then combined for later analysis. For example, a set of 1,000,000 different Primer IDs could be physically divided into 10 sets of 100,000 different Primer IDs and each could be used to Primer ID a different mixture. The identity of the Primer IDs in each set can be used as an indication of the original source. Counting of multiple samples in parallel can be facilitated.

In one embodiment the Primer ID may also be used in conjunction with a barcode, which may be 2-10 nucleotides, e.g., 2, 3, 4, 5, 6, 7, 8, 9, or 10 nucleotides. The barcode may be directly linked to the Primer ID or there may be an intervening sequence between the barcode and the Primer ID. The barcode may represent an analysis date, time or location; a clinical trial; a collection date, time or location; a patient number; a sample number; a species; a subspecies; a subtype; a therapeutic regimen; or a tissue type. In one non-limiting embodiment, both the Primer ID and the barcode are single-stranded. A 3 nucleotide barcode representing different study dates is exemplified herein.

The term "detectable label" as used herein refers to any chemical moiety attached to a nucleotide, nucleotide polymer, or nucleic acid binding factor, wherein the attachment may be covalent or non-covalent. Preferably, the label is detectable and renders the nucleotide or nucleotide polymer detectable to the practitioner of the invention. Detectable labels that may be used in combination with the methods disclosed herein include, for example, a fluorescent label, a chemiluminescent label, a quencher, a radioactive label, biotin and gold, or combinations thereof. Detectable labels include luminescent molecules, fluorochromes, fluorescent quenching agents, colored molecules, radioisotopes or scintillants. Detectable labels also include any useful linker molecule (such as biotin, avidin, streptavidin, HRP, protein A, protein G, antibodies or fragments thereof, Grb2, polyhistidine, $Ni^{2+}$, FLAG tags, myc tags), heavy metals, enzymes (examples include alkaline phosphatase, peroxidase and luciferase), electron donors/acceptors, acridinium esters, dyes and calorimetric substrates. It is also envisioned that a change in mass may be considered a detectable label, as is the case of surface plasmon resonance detection. The skilled artisan would readily recognize useful detectable labels that are not mentioned above, which may be employed in the operation of the present invention. In some instances, detectable labels are used with primers. In some instances, detectable labels are used with the Primer IDs. In some instances, detectable labels are used with the nucleic acid template molecule. In some instances, detectable labels are used to detect the tagged amplicons. In some instances, detectable labels are used to detect the nucleic acid template molecule.

The term "consensus sequence" as used herein refers to a sequence formed from two or more sequences containing an identical Primer ID. In some instances, a consensus sequence is the most common variant of a nucleic acid molecule.

Disclosed herein is a method for determining genetic diversity of a sample comprising: (a) providing a sample comprising a nucleic acid template molecule; (b) attaching a primer comprising a Primer ID to each nucleic acid template molecule to be analyzed to generate a tagged nucleic acid template, wherein each tagged nucleic acid template is attached to a unique Primer ID; (c) amplifying the tagged nucleic acid template to produce tagged amplicons; and (d) detecting the tagged amplicons, thereby determining genetic diversity of a sample. In some embodiments, the Primer ID comprises a degenerate sequence. In some embodiments, the Primer ID comprises a semi-degenerate sequence. In some embodiments, the Primer ID comprises a mixed sequence. In some embodiments, the Primer ID comprises an ambiguous sequence. In some embodiments, the Primer ID comprises a wobble sequence. In some embodiments, the Primer ID comprises a random sequence. In some embodiments, the Primer ID comprises a predetermined sequence. In some embodiments, the Primer ID is attached to the template by ligation. In some embodiments, the Primer ID is attached to the template by hybridization. In some embodiments, the Primer ID is attached to the template through PCR. In some embodiments, at least one template molecule is analyzed. In some embodiments, at least two different template molecules are analyzed. In some embodiments, detecting the tagged amplicons comprises sequencing the tagged amplicons. Sequencing of the tagged amplicons may occur by a variety of methods, including, but not limited to the Maxam-Gilbert sequencing method, the Sanger dideoxy sequencing method, dye-terminator sequencing method, pyrosequencing, multiple-primer DNA sequencing, shotgun sequencing, and primer walking. In some embodiments, sequencing comprises pyrosequencing. In some embodiments, detecting the tagged amplicons further comprises counting a number of different Primer IDs associated with the tagged amplicons, wherein the number of different Primer IDs associated with the tagged amplicons reflects the number of templates sampled. In some embodiments, the method further comprises forming a consensus sequence for tagged amplicons comprising the same Primer ID. In some embodiments, the nucleic acid template comprises a DNA template. In some embodiments, the nucleic acid template comprises an RNA template. In some embodiments, amplifying comprises a PCR-based method. In some embodiments, the PCR-based method comprises PCR. In some embodiments, the PCR-based method comprises quantitative PCR. In some embodiments, the PCR-based method comprises emulsion PCR. In some embodiments, the PCR-based method comprises droplet PCR. In some embodiments, the PCR-based method comprises hot start PCR. In some embodiments, the PCR-based method comprises in situ PCR. In some embodiments, the PCR-based method comprises inverse PCR. In some embodiments, the PCR-based method comprises multiplex PCR. In some embodiments, the PCR-based method comprises Variable Number of Tandem Repeats (VNTR) PCR. In some embodiments, the PCR-based method comprises asymmetric PCR. In some embodiments, the PCR-based method comprises long PCR. In some embodiments, the PCR-based method comprises nested PCR. In some embodiments, the PCR-based method comprises a hemi-nested PCR. In some embodiments, the PCR-based method comprises touchdown PCR. In some embodiments, the PCR-based method comprises assembly PCR. In some embodiments, the PCR-based method comprises colony PCR. In some embodiments, amplifying comprises a non-PCR-based method. In some embodiments, the non-PCR-based method comprises multiple displacement amplification (MDA). In some embodiments, the non-PCR-based method comprises transcription-mediated amplification (TMA). In some embodiments, the non-PCR-based method comprises nucleic acid sequence-based amplification (NASBA). In some embodiments, the non-PCR-based method comprises strand displacement amplification (SDA). In some embodiments, the non-PCR-based method comprises real-time SDA. In some embodiments, the non-PCR-based method comprises rolling circle amplification. In some embodiments, the non-PCR-based method comprises circle-to-circle amplification.

Suitable next generation sequencing technologies are widely available for use in connection with the methods described herein. Examples include the 454 Life Sciences platform (Roche, Branford, Conn.) (Margulies et al. 2005 *Nature*, 437, 376-380); Illumina's Genome Analyzer, GoldenGate Methylation Assay, or Infinium Methylation Assays, i.e., Infinium HumanMethylation 27K BeadArray or VeraCode GoldenGate methylation array (Illumina, San Diego, Calif.; Bibkova et al., 2006, *Genome Res.* 16, 383-393; U.S. Pat. Nos. 6,306,597 and 7,598,035 (Macevicz); U.S. Pat. No. 7,232,656 (Balasubramanian et al.)); or DNA Sequencing by Ligation, SOLiD System (Applied Biosystems/Life Technologies; U.S. Pat. Nos. 6,797,470, 7,083,917, 7,166, 434, 7,320,865, 7,332,285, 7,364,858, and 7,429,453 (Barany et al.); or the Helicos True Single Molecule DNA sequencing technology (Harris et al., 2008 *Science*, 320, 106-109; U.S. Pat. Nos. 7,037,687 and 7,645,596 (Williams et al.); U.S. Pat. No. 7,169,560 (Lapidus et al.); U.S. Pat. No. 7,769,400 (Harris)), the single molecule, real-time (SMRT™) technology of Pacific Biosciences, and sequencing (Soni and Meller, 2007, *Clin. Chem.* 53, 1996-2001) which are incorporated herein by reference in their entirety. These systems allow the sequencing of many nucleic acid molecules isolated from a specimen at high orders of multiplexing in a parallel fashion (Dear, 2003, *Brief Funct. Genomic Proteomic*, 1(4), 397-416 and McCaughan and Dear, 2010, *J. Pathol.*, 220, 297-306). Each of these platforms allow sequencing of clonally expanded or non-amplified single molecules of nucleic acid fragments. Certain platforms involve, for example, (i) sequencing by ligation of dye-modified probes (including cyclic ligation and cleavage), (ii) pyrosequencing, and (iii) single-molecule sequencing.

Pyrosequencing is a nucleic acid sequencing method based on sequencing by synthesis, which relies on detection of a pyrophosphate released on nucleotide incorporation. Generally, sequencing by synthesis involves synthesizing, one nucleotide at a time, a DNA strand complimentary to the strand whose sequence is being sought. Study nucleic acids may be immobilized to a solid support, hybridized with a sequencing primer, incubated with DNA polymerase, ATP sulfurylase, luciferase, apyrase, adenosine 5' phosphsulfate and luciferin. Nucleotide solutions are sequentially added and removed. Correct incorporation of a nucleotide releases a pyrophosphate, which interacts with ATP sulfurylase and produces ATP in the presence of adenosine 5' phosphsulfate, fueling the luciferin reaction, which produces a chemiluminescent signal allowing sequence determination. Machines for pyrosequencing and methylation specific reagents are available from Qiagen, Inc. (Valencia, Calif.). See also Tost and Gut, 2007, *Nat. Prot.* 2 2265-2275. An example of a system that can be used by a person of ordinary skill based on pyrosequencing generally involves the following steps: ligating an adaptor nucleic acid to a study nucleic acid and hybridizing the study nucleic acid to a bead; amplifying a nucleotide sequence in the study nucleic acid in an emulsion; sorting beads using a picoliter multiwell solid support; and sequencing amplified nucleotide sequences by pyrosequencing methodology (e.g., Nakano et al., 2003, *J. Biotech.* 102, 117-124). Such a system can be used to exponentially amplify amplification products generated by a process described herein, e.g., by ligating a heterologous nucleic acid to the first amplification product generated by a process described herein.

Certain single-molecule sequencing embodiments are based on the principal of sequencing by synthesis, and utilize single-pair Fluorescence Resonance Energy Transfer (single pair FRET) as a mechanism by which photons are emitted as a result of successful nucleotide incorporation. The emitted photons often are detected using intensified or high sensitivity cooled charge-couple-devices in conjunction with total internal reflection microscopy (TIRM). Photons are only emitted when the introduced reaction solution contains the correct nucleotide for incorporation into the growing nucleic acid chain that is synthesized as a result of the sequencing process. In FRET based single-molecule sequencing or detection, energy is transferred between two fluorescent dyes, sometimes polymethine cyanine dyes Cy3 and Cy5, through long-range dipole interactions. The donor is excited at its specific excitation wavelength and the excited state energy is transferred, non-radiatively to the acceptor dye, which in turn becomes excited. The acceptor dye eventually returns to the ground state by radiative emission of a photon. The two dyes used in the energy transfer process represent the "single pair", in single pair FRET. Cy3 often is used as the donor fluorophore and often is incorporated as the first labeled nucleotide. Cy5 often is used as the acceptor fluorophore and is used as the nucleotide label for successive nucleotide additions after incorporation of a first Cy3 labeled nucleotide. The fluorophores generally are within 10 nanometers of each other for energy transfer to occur successfully. Bailey et al. recently reported a highly sensitive (15 pg methylated DNA) method using quantum dots to detect methylation status using fluorescence resonance energy transfer (MS-qFRET)(Bailey et al. 2009, *Genome Res.* 19(8), 1455-1461, which is incorporated herein by reference in its entirety).

An example of a system that can be used based on single-molecule sequencing generally involves hybridizing a primer to a study nucleic acid to generate a complex; associating the complex with a solid phase; iteratively extending the primer by a nucleotide tagged with a fluorescent molecule; and capturing an image of fluorescence resonance energy transfer signals after each iteration (e.g., Braslaysky et al., PNAS 100(7): 3960-3964 (2003); U.S. Pat. No. 7,297,518 (Quake et al.) which are incorporated herein by reference in their entirety). Such a system can be used to directly sequence amplification products generated by processes described herein. In some embodiments the released linear amplification product can be hybridized to a primer that contains sequences complementary to immobilized capture sequences present on a solid support, a bead or glass slide for example. Hybridization of the primer-released linear amplification product complexes with the immobilized capture sequences, immobilizes released linear amplification products to solid supports for single pair FRET based sequencing by synthesis. The primer often is fluorescent, so that an initial reference image of the surface of the slide with immobilized nucleic acids can be generated. The initial reference image is useful for determining locations at which true nucleotide incorporation is occurring. Fluorescence signals detected in array locations not initially identified in the "primer only" reference image are discarded as non-specific fluorescence. Following immobilization of the primer-released linear amplification product complexes, the bound nucleic acids often are sequenced in parallel by the iterative steps of, a) polymerase extension in the presence of one fluorescently labeled nucleotide, b) detection of fluorescence using appropriate microscopy, TIRM for example, c) removal of fluorescent nucleotide, and d) return to step a with a different fluorescently labeled nucleotide.

In some embodiments, at least 2 different nucleic acid template molecules are analyzed. In some embodiments, at least 3 different nucleic acid template molecules are analyzed. In some embodiments, at least 4 different nucleic acid template molecules are analyzed. In some embodiments, at least 5 different nucleic acid template molecules are analyzed. In some embodiments, at least 6 different nucleic acid template molecules are analyzed. In some embodiments, at least 7 different nucleic acid template molecules are analyzed. In some embodiments, at least 8 different nucleic acid template molecules are analyzed. In some embodiments, at least 9 different nucleic acid template molecules are analyzed. In some embodiments, at least 10 different nucleic acid template molecules are analyzed. In some embodiments, at least 15 different nucleic acid template molecules are analyzed. In some embodiments, at least 20 different nucleic acid template molecules are analyzed. In some embodiments, at least 25, at least 30, at least 35, at least 40, at least 45, at least 50, at least 55, at least 60, at least 65, at least 70, at least 75, at least 80, at least 85, at least 90, at least 95, at least 100, at least 125, at least 150, at least 175, at least 200, at least 250, at least 300, at least 350, or at least 400 different nucleic acid template molecules are analyzed. In some embodiments, at least 500 different nucleic acid template molecules are analyzed. In some embodiments, at least 1,000 different nucleic acid template molecules are analyzed. In some embodiments, at least 5,000 different nucleic acid template molecules are analyzed. In some embodiments, at least 10,000 different nucleic acid template molecules are analyzed. In some embodiments, at least 20,000 different nucleic acid template molecules are analyzed. In some embodiments, at least 30,000 different nucleic acid template molecules are analyzed. In some embodiments, at least 40,000 different nucleic acid template molecules are analyzed. In some embodiments, at least 50,000 different nucleic acid template molecules are analyzed. In some embodiments, at least 60,000 different nucleic acid template molecules are analyzed. In some embodiments, at least 70,000 different nucleic acid template molecules are analyzed. In some embodiments, at least 80,000 different nucleic acid template molecules are analyzed. In some embodiments, at least 90,000 different nucleic acid template molecules are analyzed. In some embodiments, at least 100,000 different nucleic acid template molecules are analyzed. In some embodiments, the Primer IDs are attached to the nucleic acid template molecules simultaneously. In some embodiments, the Primer IDs are attached to the nucleic acid template molecules sequentially. In some embodiments, the nucleic acid template molecules are amplified and/or detected simultaneously. In some embodiments, the nucleic acid template molecules are amplified and/or detected sequentially. In some embodiments, the Primer ID comprises a nucleic acid sequence. In some embodiments, the Primer ID comprises a deoxyribonucleic acid sequence. In some embodiments, the Primer ID comprises a ribonucleic acid sequence. In some embodiments, the Primer ID comprises 5-100 nucleotides. In some embodiments, the Primer ID comprises 5-50 nucleotides. In some embodiments, the Primer ID comprises at least 6 nucleotides. In some embodiments, the Primer ID comprises at least 7 nucleotides. In some embodiments, the Primer ID comprises at least 8 nucleotides. In some embodiments, the Primer ID comprises at least 9 nucleotides. In some embodiments, the Primer ID comprises at least 10 nucleotides. In some embodiments, the Primer ID comprises at least 12 nucleotides. In some embodiments, the Primer ID comprises at least 15 nucleotides. In some embodiments, the Primer ID comprises at least 20 nucleotides. In some embodiments, the Primer ID comprises at least 25 nucleotides. In some embodiments, the Primer ID comprises at least 35 nucleotides.

Further provided is a method for detecting genetic variants comprising: (a) providing a sample comprising a nucleic acid template molecule; (b) attaching a primer comprising a Primer ID to each nucleic acid template molecule to be analyzed to generate a tagged nucleic acid template, wherein each tagged nucleic template is attached to a unique Primer ID; (c) amplifying the tagged nucleic acid template to produce tagged amplicons; and (d) detecting the tagged amplicons, thereby detecting genetic variants. In some embodiments, detecting the genetic variants comprises determining the prevalence of mutations. In some embodiments, detecting the genetic variants comprises forming a consensus sequence for tagged nucleic acid templates comprising the same Primer ID. In some embodiments, detecting genetic variants comprises sequencing the tagged amplicons. Sequencing of the tagged amplicons may occur by a variety of methods, including, but not limited to the Maxam-Gilbert sequencing method, the Sanger dideoxy sequencing method, dye-terminator sequencing method, pyrosequencing, multiple-primer DNA sequencing, shotgun sequencing, primer walking. In some embodiments, sequencing comprises pyrosequencing. In some embodiments, detecting genetic variants comprises counting a number of different tagged amplicons. In some embodiments, the genetic variant comprises a polymorphism. In some embodiments, the polymorphism comprises a single nucleotide polymorphism. In some instances, the polymorphism occurs at a frequency of less than 0.5%. In some instances, the polymorphism occurs at a frequency of less than 1%. In some instances, the polymorphism occurs at a frequency of less than 2%. In some instances, the polymorphism occurs at a frequency of less than 5%. In some instances, the polymorphism occurs at a frequency of greater than 1%. In some instances, the polymorphism occurs at a frequency of greater than 5%. In some instances, the polymorphism occurs at a frequency of greater than 10%. In some instances, the polymorphism occurs at a frequency of greater than 20%. In some instances, the polymorphism occurs at a frequency of greater than 30%. In some embodiments, the genetic variant comprises a mutation. In some embodiments, the genetic variant comprises a deletion. In some embodiments, the genetic variant comprises an insertion. In some embodiments, the Primer ID comprises a degenerate sequence. In some embodiments, the Primer ID comprises a semi-degenerate sequence. In some embodiments, the Primer ID comprises a mixed sequence. In some embodiments, the Primer ID comprises an ambiguous sequence. In some embodiments, the Primer ID comprises a wobble sequence. In some embodiments, the Primer ID comprises a random sequence. In some embodiments, the Primer ID comprises a predetermined sequence. In some embodiments, the Primer ID is attached to the template by ligation. In some embodiments, the Primer ID is attached to the template by hybridization. In some embodiments, the Primer ID is attached to template through PCR. In some embodiments, at least one template molecule is analyzed. In some embodiments, at least two different template molecules are analyzed. In some embodiments, detecting the tagged amplicons further comprises counting a number of different Primer IDs associated with the tagged amplicons, wherein the number of different Primer IDs associated with the tagged amplicons reflects the number of templates sampled. In some embodiments, the method further comprises forming a consensus sequence for tagged amplicons comprising the same Primer ID. In some embodiments, amplifying comprises a PCR-based method. In some embodiments, the PCR-based method comprises PCR. In some embodiments, the PCR-based method comprises quantitative PCR. In some embodiments, the PCR-based method comprises emulsion PCR. In some embodiments, the PCR-based method comprises droplet PCR. In some embodiments, the PCR-based method comprises hot start PCR. In some embodiments, the PCR-based method comprises in situ PCR. In some embodiments, the PCR-based method comprises inverse PCR. In some embodiments, the PCR-based method comprises multiplex PCR. In some embodiments, the PCR-based method comprises Variable Number of Tandem Repeats (VNTR) PCR. In some embodiments, the PCR-based method comprises asymmetric PCR. In some embodiments, the PCR-based method comprises long PCR. In some embodiments, the PCR-based method comprises nested PCR. In some embodiments, the PCR-based method comprises hemi-nested PCR. In some embodiments, the PCR-based method comprises touchdown PCR. In some embodiments, the PCR-based method comprises assembly PCR. In some embodiments, the PCR-based method comprises colony PCR. In some embodiments, amplifying comprises a non-PCR-based method. In some embodiments, the non-PCR-based method comprises multiple displacement amplification (MDA). In some embodiments, the non-PCR-based method comprises transcription-mediated amplification (TMA). In some embodiments, the non-PCR-based method comprises nucleic acid sequence-based amplification (NASBA). In some embodiments, the non-PCR-based method comprises strand displacement amplification (SDA). In some embodiments, the non-PCR-based method comprises real-time SDA. In some embodiments, the non-PCR-based method comprises rolling circle amplification. In some embodiments, the non-PCR-based method comprises circle-to-circle amplification. In some embodiments, the nucleic acid template comprises a DNA template. In some embodiments, the nucleic acid template comprises an RNA template. In some embodiments, at least 2 different nucleic acid template molecules are analyzed. In some embodiments, at least 3 different nucleic acid template molecules are analyzed. In some embodiments, at least 4 different nucleic acid template molecules are analyzed. In some embodiments, at least 5 different nucleic acid template molecules are analyzed. In some embodiments, at least 6 different nucleic acid template molecules are analyzed. In some embodiments, at least 7 different nucleic acid template molecules are analyzed. In some embodiments, at least 8 different nucleic acid template molecules are analyzed. In some embodiments, at least 9 different nucleic acid template molecules are analyzed. In some embodiments, at least 10 different nucleic acid template molecules are analyzed. In some embodiments, at least 15 different nucleic acid template molecules are analyzed. In some embodiments, at least 20 different nucleic acid template molecules are analyzed. In some embodiments, at least 25, at least 30, at least 35, at least 40, at least 45, at least 50, at least 55, at least 60, at least 65, at least 70, at least 75, at least 80, at least 85, at least 90, at least 95, at least 100, at least 125, at least 150, at least 175, at least 200, at least 250, at least 300, at least 350, or at least 400 different nucleic acid template molecules are analyzed. In some embodiments, at least 500 different nucleic acid template molecules are analyzed. In some embodiments, at least 1,000 different nucleic acid template molecules are analyzed. In some embodiments, at least 5,000 different nucleic acid template molecules are analyzed. In some embodiments, at least 10,000 different nucleic acid template molecules are analyzed. In some embodiments, at least 20,000 different nucleic acid template molecules are analyzed. In some embodiments, at least 30,000 different nucleic acid template molecules are analyzed. In some embodiments, at least 40,000 different nucleic acid template molecules are analyzed. In some embodiments, at least 50,000 different nucleic acid template molecules are analyzed. In some embodiments, at least 60,000 different nucleic acid template molecules are analyzed. In some embodiments, at least 70,000 different nucleic acid template molecules are analyzed. In some embodiments, at least 80,000 different nucleic acid template molecules are analyzed. In some embodiments, at least 90,000 different nucleic acid template molecules are analyzed. In some embodiments, at least 100,000 different nucleic acid template molecules are analyzed. In some embodiments, the Primer IDs are attached to the nucleic acid template molecules simultaneously. In some embodiments, the Primer IDs are attached to the nucleic acid template molecules sequentially. In some embodiments, the nucleic acid template molecules are amplified and/or detected simultaneously. In some embodiments, the nucleic acid template molecules are amplified and/or detected sequentially. In some embodiments, the Primer ID comprises 5-100 nucleotides. In some embodiments, the Primer ID comprises 5-50 nucleotides. In some embodiments, the Primer ID comprises at least 6 nucleotides. In some embodiments, the Primer ID comprises at least 7 nucleotides. In some embodiments, the Primer ID comprises at least 8 nucleotides. In some embodiments, the Primer ID comprises at least 9 nucleotides. In some embodiments, the Primer ID comprises at least 10 nucleotides. In some embodiments, the Primer ID comprises at least 12 nucleotides. In some embodiments, the Primer ID comprises at least 15 nucleotides. In some embodiments, the Primer ID comprises at least 20 nucleotides. In some embodiments, the Primer ID comprises at least 25 nucleotides. In some embodiments, the Primer ID comprises at least 35 nucleotides.

Also provided herein is a method for determining or screening for drug-resistant variants comprising: (a) providing a sample comprising a nucleic acid template molecule; (b) attaching a primer comprising a Primer ID to each nucleic acid template molecule to be analyzed to generate a tagged nucleic acid template, wherein each tagged nucleic acid template is attached to a unique Primer ID; (c) amplifying the tagged nucleic acid template to produce tagged amplicons; and (d) detecting the tagged amplicons, thereby determining or screening for drug-resistant variants. In some embodiments, detecting the tagged amplicons comprises sequencing the tagged amplicons. Sequencing of the tagged amplicons may occur by a variety of methods, including, but not limited to the Maxam-Gilbert sequencing method, the Sanger dideoxy sequencing method, dye-terminator sequencing method, pyrosequencing, multiple-primer DNA sequencing, shotgun sequencing, primer walking. In some embodiments, sequencing comprises pyrosequencing. In some embodiments, detecting the tagged amplicons further comprises forming a consensus sequence for the tagged amplicons comprising the same Primer ID. In some embodiments, the nucleic acid template molecule comprises a viral sequence. In some embodiments, the nucleic acid template molecule comprises a bacterial sequence. In some embodiments, the sample is from an individual suffering from a viral infection. In some embodiments, the sample is from an individual suffering from a bacterial infection. In some embodiments, the sample is from an individual suffering from cancer. In some embodiments, the sample is from an individual suffering from an autoimmune disorder. In some embodiments, the Primer ID comprises a degenerate sequence. In some embodiments, the Primer ID comprises a semi-degenerate sequence. In some embodiments, the Primer ID comprises a mixed sequence. In some embodiments, the Primer ID comprises an ambiguous sequence. In some embodiments, the Primer ID comprises a wobble sequence. In some embodiments, the Primer ID comprises a random sequence. In some embodiments, the Primer ID comprises a predetermined sequence. In some embodiments, the Primer ID is attached to the template by ligation. In some embodiments, the Primer ID is attached to the template by hybridization. In some embodiments, the Primer ID is attached to the template through PCR. In some embodiments, at least one template molecule is analyzed. In some embodiments, at least two different template molecules are analyzed. In some embodiments, detecting the tagged amplicons further comprises counting a number of different Primer IDs associated with the tagged amplicons, wherein the number of different Primer IDs associated with the tagged amplicons reflects the number of templates sampled. In some embodiments, amplifying comprises a PCR-based method. In some embodiments, the PCR-based method comprises PCR. In some embodiments, the PCR-based method comprises quantitative PCR. In some embodiments, the PCR-based method comprises emulsion PCR. In some embodiments, the PCR-based method comprises droplet PCR. In some embodiments, the PCR-based method comprises hot start PCR. In some embodiments, the PCR-based method comprises in situ PCR. In some embodiments, the PCR-based method comprises inverse PCR. In some embodiments, the PCR-based method comprises multiplex PCR. In some embodiments, the PCR-based method comprises Variable Number of Tandem Repeats (VNTR) PCR.

In some embodiments, the PCR-based method comprises asymmetric PCR. In some embodiments, the PCR-based method comprises long PCR. In some embodiments, the PCR-based method comprises nested PCR. In some embodiments, the PCR-based method comprises hemi-nested PCR. In some embodiments, the PCR-based method comprises touchdown PCR. In some embodiments, the PCR-based method comprises assembly PCR. In some embodiments, the PCR-based method comprises colony PCR. In some embodiments, amplifying comprises a non-PCR-based method. In some embodiments, the non-PCR-based method comprises multiple displacement amplification (MDA). In some embodiments, the non-PCR-based method comprises transcription-mediated amplification (TMA). In some embodiments, the non-PCR-based method comprises nucleic acid sequence-based amplification (NASBA). In some embodiments, the non-PCR-based method comprises strand displacement amplification (SDA). In some embodiments, the non-PCR-based method comprises real-time SDA. In some embodiments, the non-PCR-based method comprises rolling circle amplification. In some embodiments, the non-PCR-based method comprises circle-to-circle amplification. In some embodiments, at least 2 different nucleic acid template molecules are analyzed. In some embodiments, at least 3 different nucleic acid template molecules are analyzed. In some embodiments, at least 4 different nucleic acid template molecules are analyzed. In some embodiments, at least 5 different nucleic acid template molecules are analyzed. In some embodiments, at least 6 different nucleic acid template molecules are analyzed. In some embodiments, at least 7 different nucleic acid template molecules are analyzed. In some embodiments, at least 8 different nucleic acid template molecules are analyzed. In some embodiments, at least 9 different nucleic acid template molecules are analyzed. In some embodiments, at least 10 different nucleic acid template molecules are analyzed. In some embodiments, at least 15 different nucleic acid template molecules are analyzed. In some embodiments, at least 20 different nucleic acid template molecules are analyzed. In some embodiments, at least 25, at least 30, at least 35, at least 40, at least 45, at least 50, at least 55, at least 60, at least 65, at least 70, at least 75, at least 80, at least 85, at least 90, at least 95, at least 100, at least 125, at least 150, at least 175, at least 200, at least 250, at least 300, at least 350, or at least 400 different nucleic acid template molecules are analyzed. In some embodiments, at least 500 different nucleic acid template molecules are analyzed. In some embodiments, at least 1,000 different nucleic acid template molecules are analyzed. In some embodiments, at least 5,000 different nucleic acid template molecules are analyzed. In some embodiments, at least 10,000 different nucleic acid template molecules are analyzed. In some embodiments, at least 20,000 different nucleic acid template molecules are analyzed. In some embodiments, at least 30,000 different nucleic acid template molecules are analyzed. In some embodiments, at least 40,000 different nucleic acid template molecules are analyzed. In some embodiments, at least 50,000 different nucleic acid template molecules are analyzed. In some embodiments, at least 60,000 different nucleic acid template molecules are analyzed. In some embodiments, at least 70,000 different nucleic acid template molecules are analyzed. In some embodiments, at least 80,000 different nucleic acid template molecules are analyzed. In some embodiments, at least 90,000 different nucleic acid template molecules are analyzed. In some embodiments, at least 100,000 different nucleic acid template molecules are analyzed. In some embodiments, the Primer IDs are attached to the nucleic acid template molecules simultaneously. In some embodiments, the Primer IDs are attached to the nucleic acid template molecules sequentially. In some embodiments, the nucleic acid template molecules are amplified and/or detected simultaneously. In some embodiments, the nucleic acid template molecules are amplified and/or detected sequentially. In some embodiments, the Primer ID comprises 5-100 nucleotides. In some embodiments, the Primer ID comprises 5-50 nucleotides. In some embodiments, the Primer ID comprises at least 6 nucleotides. In some embodiments, the Primer ID comprises at least 7 nucleotides. In some embodiments, the Primer ID comprises at least 8 nucleotides. In some embodiments, the Primer ID comprises at least 9 nucleotides. In some embodiments, the Primer ID comprises at least 10 nucleotides. In some embodiments, the Primer ID comprises at least 12 nucleotides. In some embodiments, the Primer ID comprises at least 15 nucleotides. In some embodiments, the Primer ID comprises at least 20 nucleotides. In some embodiments, the Primer ID comprises at least 25 nucleotides. In some embodiments, the Primer ID comprises at least 35 nucleotides.

Further disclosed herein is a method for determining PCR resampling in an amplification reaction comprising: (a) providing a sample comprising a nucleic acid template molecule; (b) attaching a primer comprising a Primer ID to each nucleic acid template molecule to be analyzed to generate a tagged nucleic acid template, wherein each tagged nucleic acid template is attached to a unique Primer ID; (c) amplifying the tagged nucleic acid template to produce tagged amplicons; and (d) detecting the tagged amplicons, thereby determining PCR resampling in an amplification reaction. In some embodiments, the Primer ID comprises a degenerate sequence. In some embodiments, the Primer ID comprises a semi-degenerate sequence. In some embodiments, the Primer ID comprises a mixed sequence. In some embodiments, the Primer ID comprises an ambiguous sequence. In some embodiments, the Primer ID comprises a wobble sequence. In some embodiments, the Primer ID comprises a random sequence. In some embodiments, the Primer ID comprises a predetermined sequence. In some embodiments, the Primer ID is attached to the template by ligation. In some embodiments, the Primer ID is attached to the template by hybridization. In some embodiments, the Primer ID is attached to the template through PCR. In some embodiments, at least one template molecule is analyzed. In some embodiments, at least two different template molecules are analyzed. In some embodiments, detecting the tagged amplicons comprises sequencing the tagged amplicons. Sequencing of the tagged amplicons may occur by a variety of methods, including, but not limited to the Maxam-Gilbert sequencing method, the Sanger dideoxy sequencing method, dye-terminator sequencing method, pyrosequencing, multiple-primer DNA sequencing, shotgun sequencing, primer walking. In some embodiments, sequencing comprises pyrosequencing. In some embodiments, detecting the tagged amplicons further comprises counting a number of different Primer IDs associated with the tagged amplicons, wherein the number of different Primer IDs associated with the tagged amplicons reflects the number of templates sampled. In some embodiments, the method further comprises forming a consensus sequence for tagged amplicons comprising the same Primer ID. In some embodiments, the nucleic acid template comprises a DNA template. In some embodiments, the nucleic acid template comprises an RNA template. In some embodiments, amplifying comprises a PCR-based method. In some embodiments, the PCR-based method comprises PCR. In some embodiments, the PCR-based method comprises quantitative PCR. In some embodiments, the PCR-based method comprises emulsion PCR. In some embodiments, the PCR-based method comprises droplet PCR. In some embodiments, the PCR-based method comprises hot start PCR. In some embodiments, the PCR-based method comprises in situ PCR. In some embodiments, the PCR-based method comprises inverse PCR. In some embodiments, the PCR-based method comprises multiplex PCR. In some embodiments, the PCR-based method comprises Variable Number of Tandem Repeats (VNTR) PCR. In some embodiments, the PCR-based method comprises asymmetric PCR. In some embodiments, the PCR-based method comprises long PCR. In some embodiments, the PCR-based method comprises nested PCR. In some embodiments, the PCR-based method comprises hemi-nested PCR. In some embodiments, the PCR-based method comprises touchdown PCR. In some embodiments, the PCR-based method comprises assembly PCR. In some embodiments, the PCR-based method comprises colony PCR. In some embodiments, amplifying comprises a non-PCR-based method. In some embodiments, the non-PCR-based method comprises multiple displacement amplification (MDA). In some embodiments, the non-PCR-based method comprises transcription-mediated amplification (TMA). In some embodiments, the non-PCR-based method comprises nucleic acid sequence-based amplification (NASBA). In some embodiments, the non-PCR-based method comprises strand displacement amplification (SDA). In some embodiments, the non-PCR-based method comprises real-time SDA. In some embodiments, the non-PCR-based method comprises rolling circle amplification. In some embodiments, the non-PCR-based method comprises circle-to-circle amplification. In some embodiments, at least 2 different nucleic acid template molecules are analyzed. In some embodiments, at least 3 different nucleic acid template molecules are analyzed. In some embodiments, at least 4 different nucleic acid template molecules are analyzed. In some embodiments, at least 5 different nucleic acid template molecules are analyzed. In some embodiments, at least 6 different nucleic acid template molecules are analyzed. In some embodiments, at least 7 different nucleic acid template molecules are analyzed. In some embodiments, at least 8 different nucleic acid template molecules are analyzed. In some embodiments, at least 9 different nucleic acid template molecules are analyzed. In some embodiments, at least 10 different nucleic acid template molecules are analyzed. In some embodiments, at least 15 different nucleic acid template molecules are analyzed. In some embodiments, at least 20 different nucleic acid template molecules are analyzed. In some embodiments, at least 25, at least 30, at least 35, at least 40, at least 45, at least 50, at least 55, at least 60, at least 65, at least 70, at least 75, at least 80, at least 85, at least 90, at least 95, at least 100, at least 125, at least 150, at least 175, at least 200, at least 250, at least 300, at least 350, or at least 400 different nucleic acid template molecules are analyzed. In some embodiments, at least 500 different nucleic acid template molecules are analyzed. In some embodiments, at least 1,000 different nucleic acid template molecules are analyzed. In some embodiments, at least 5,000 different nucleic acid template molecules are analyzed. In some embodiments, at least 10,000 different nucleic acid template molecules are analyzed. In some embodiments, at least 20,000 different nucleic acid template molecules are analyzed. In some embodiments, at least 30,000 different nucleic acid template molecules are analyzed. In some embodiments, at least 40,000 different nucleic acid template molecules are analyzed. In some embodiments, at least 50,000 different nucleic acid template molecules are analyzed. In some embodiments, at least 60,000 different nucleic acid template molecules are analyzed. In some embodiments, at least 70,000 different nucleic acid template molecules are analyzed. In some embodiments, at least 80,000 different nucleic acid template molecules are analyzed. In some embodiments, at least 90,000 different nucleic acid template molecules are analyzed. In some embodiments, at least 100,000 different nucleic acid template molecules are analyzed. In some embodiments, the Primer IDs are attached to the nucleic acid template molecules simultaneously. In some embodiments, the Primer IDs are attached to the nucleic acid template molecules sequentially. In some embodiments, the nucleic acid template molecules are amplified and/or detected simultaneously. In some embodiments, the nucleic acid template molecules are amplified and/or detected sequentially. In some embodiments, the Primer ID comprises 5-100 nucleotides. In some embodiments, the Primer ID comprises 5-50 nucleotides. In some embodiments, the Primer ID comprises at least 6 nucleotides. In some embodiments, the Primer ID comprises at least 7 nucleotides. In some embodiments, the Primer ID comprises at least 8 nucleotides. In some embodiments, the Primer ID comprises at least 9 nucleotides. In some embodiments, the Primer ID comprises at least 10 nucleotides. In some embodiments, the Primer ID comprises at least 12 nucleotides. In some embodiments, the Primer ID comprises at least 15 nucleotides. In some embodiments, the Primer ID comprises at least 20 nucleotides. In some embodiments, the Primer ID comprises at least 25 nucleotides. In some embodiments, the Primer ID comprises at least 35 nucleotides.

Further disclosed herein is a method for determining PCR errors and/or sequencing errors comprising: (a) providing a sample comprising a nucleic acid template molecule; (b) attaching a primer comprising a Primer ID to each nucleic acid template molecule to be analyzed to generate a tagged nucleic acid template, wherein each tagged nucleic acid template is attached to a unique Primer ID; (c) amplifying the tagged nucleic acid template to produce tagged amplicons; and (d) detecting the tagged amplicons, thereby determining PCR errors and/or sequencing errors. In some embodiments, determining the PCR errors and/or sequencing error comprises determining fidelity of a polymerase. In some embodiments, determining the PCR error and/or sequencing error comprises determining accuracy of oligonucleotides synthesized in vitro. In some embodiments, determining the PCR error and/or sequencing error comprises determining the PCR error and/or sequencing error comprises determining accuracy of the sequencing reaction. In some embodiments, the Primer ID comprises a degenerate sequence. In some embodiments, the Primer ID comprises a semi-degenerate sequence. In some embodiments, the Primer ID comprises a mixed sequence. In some embodiments, the Primer ID comprises an ambiguous sequence. In some embodiments, the Primer ID comprises a wobble sequence. In some embodiments, the Primer ID comprises a random sequence. In some embodiments, the Primer ID comprises a predetermined sequence. In some embodiments, the Primer ID is attached to the template by ligation. In some embodiments, the Primer ID is attached to the template by hybridization. In some embodiments, the Primer ID is attached to the template through PCR. In some embodiments, at least one template molecule is analyzed. In some embodiments, at least two different template molecules are analyzed. In some embodiments, detecting the tagged amplicons further comprises counting a number of different Primer IDs associated with the tagged amplicons, wherein the number of different Primer IDs associated with the tagged amplicons reflects the number of templates sampled. In some embodiments, the method further comprises forming a consensus sequence for tagged amplicons comprising the same Primer ID. In some embodiments, the nucleic acid template comprises a DNA template. In some embodiments, the nucleic acid template comprises an RNA template. In some embodiments, amplifying comprises a PCR-based method. In some embodiments, the PCR-based method comprises PCR. In some embodiments, the PCR-based method comprises quantitative PCR. In some embodiments, the PCR-based method comprises emulsion PCR. In some embodiments, the PCR-based method comprises droplet PCR. In some embodiments, the PCR-based method comprises hot start PCR. In some embodiments, the PCR-based method comprises in situ PCR. In some embodiments, the PCR-based method comprises inverse PCR. In some embodiments, the PCR-based method comprises multiplex PCR. In some embodiments, the PCR-based method comprises Variable Number of Tandem Repeats (VNTR) PCR. In some embodiments, the PCR-based method comprises asymmetric PCR. In some embodiments, the PCR-based method comprises long PCR. In some embodiments, the PCR-based method comprises nested PCR. In some embodiments, the PCR-based method comprises hemi-nested PCR. In some embodiments, the PCR-based method comprises touchdown PCR. In some embodiments, the PCR-based method comprises assembly PCR. In some embodiments, the PCR-based method comprises colony PCR. In some embodiments, amplifying comprises a non-PCR-based method. In some embodiments, the non-PCR-based method comprises multiple displacement amplification (MDA). In some embodiments, the non-PCR-based method comprises transcription-mediated amplification (TMA). In some embodiments, the non-PCR-based method comprises nucleic acid sequence-based amplification (NASBA). In some embodiments, the non-PCR-based method comprises strand displacement amplification (SDA). In some embodiments, the non-PCR-based method comprises real-time SDA. In some embodiments, the non-PCR-based method comprises rolling circle amplification. In some embodiments, the non-PCR-based method comprises circle-to-circle amplification. In some embodiments, at least 2 different nucleic acid template molecules are analyzed. In some embodiments, at least 3 different nucleic acid template molecules are analyzed. In some embodiments, at least 4 different nucleic acid template molecules are analyzed. In some embodiments, at least 5 different nucleic acid template molecules are analyzed. In some embodiments, at least 6 different nucleic acid template molecules are analyzed. In some embodiments, at least 7 different nucleic acid template molecules are analyzed. In some embodiments, at least 8 different nucleic acid template molecules are analyzed. In some embodiments, at least 9 different nucleic acid template molecules are analyzed. In some embodiments, at least 10 different nucleic acid template molecules are analyzed. In some embodiments, at least 15 different nucleic acid template molecules are analyzed. In some embodiments, at least 20 different nucleic acid template molecules are analyzed. In some embodiments, at least 25, at least 30, at least 35, at least 40, at least 45, at least 50, at least 55, at least 60, at least 65, at least 70, at least 75, at least 80, at least 85, at least 90, at least 95, at least 100, at least 125, at least 150, at least 175, at least 200, at least 250, at least 300, at least 350, or at least 400 different nucleic acid template molecules are analyzed.

In some embodiments, at least 500 different nucleic acid template molecules are analyzed. In some embodiments, at least 1,000 different nucleic acid template molecules are analyzed. In some embodiments, at least 5,000 different nucleic acid template molecules are analyzed. In some embodiments, at least 10,000 different nucleic acid template molecules are analyzed. In some embodiments, at least 20,000 different nucleic acid template molecules are analyzed. In some embodiments, at least 30,000 different nucleic acid template molecules are analyzed. In some embodiments, at least 40,000 different nucleic acid template molecules are analyzed. In some embodiments, at least 50,000 different nucleic acid template molecules are analyzed. In some embodiments, at least 60,000 different nucleic acid template molecules are analyzed. In some embodiments, at least 70,000 different nucleic acid template molecules are analyzed. In some embodiments, at least 80,000 different nucleic acid template molecules are analyzed. In some embodiments, at least 90,000 different nucleic acid template molecules are analyzed. In some embodiments, at least 100,000 different nucleic acid template molecules are analyzed. In some embodiments, the Primer IDs are attached to the nucleic acid template molecules simultaneously. In some embodiments, the Primer IDs are attached to the nucleic acid template molecules sequentially. In some embodiments, the nucleic acid template molecules are amplified and/or detected simultaneously. In some embodiments, the nucleic acid template molecules are amplified and/or detected sequentially. In some embodiments, the Primer ID comprises 5-100 nucleotides. In some embodiments, the Primer ID comprises 5-50 nucleotides. In some embodiments, the Primer ID comprises at least 6 nucleotides. In some embodiments, the Primer ID comprises at least 7 nucleotides. In some embodiments, the Primer ID comprises at least 8 nucleotides. In some embodiments, the Primer ID comprises at least 9 nucleotides. In some embodiments, the Primer ID comprises at least 10 nucleotides. In some embodiments, the Primer ID comprises at least 12 nucleotides. In some embodiments, the Primer ID comprises at least 15 nucleotides. In some embodiments, the Primer ID comprises at least 20 nucleotides. In some embodiments, the Primer ID comprises at least 25 nucleotides. In some embodiments, the Primer ID comprises at least 35 nucleotides.

Further disclosed herein is a method for correcting PCR errors and/or sequencing errors comprising: (a) providing a sample comprising a nucleic acid template molecule; (b) attaching a primer comprising a Primer ID to each nucleic acid template molecule to be analyzed to generate a tagged nucleic acid template, wherein each tagged nucleic acid template is attached to a unique Primer ID; (c) amplifying the tagged nucleic acid template to produce tagged amplicons; and (d) detecting the tagged amplicons, thereby correcting PCR error and/or sequencing error. In some embodiments, the Primer ID comprises a degenerate sequence. In some embodiments, the Primer ID comprises a semi-degenerate sequence. In some embodiments, the Primer ID comprises a mixed sequence. In some embodiments, the Primer ID comprises an ambiguous sequence. In some embodiments, the Primer ID comprises a wobble sequence. In some embodiments, the Primer ID comprises a random sequence. In some embodiments, the Primer ID comprises a predetermined sequence. In some embodiments, the Primer ID is attached to the template by ligation. In some embodiments, the Primer ID is attached to the template by hybridization. In some embodiments, the Primer ID is attached to the template through PCR. In some embodiments, at least one template molecule is analyzed. In some embodiments, at least two different template molecules are analyzed. In some embodiments, detecting the tagged amplicons further comprises counting a number of different Primer IDs associated with the tagged amplicons, wherein the number of different Primer IDs associated with the tagged amplicons reflects the number of templates sampled. In some embodiments, the method further comprises forming a consensus sequence for tagged amplicons comprising the same Primer ID. In some embodiments, the nucleic acid template comprises a DNA template. In some embodiments, the nucleic acid template comprises an RNA template. In some embodiments, amplifying comprises a PCR-based method. In some embodiments, the PCR-based method comprises PCR. In some embodiments, the PCR-based method comprises quantitative PCR. In some embodiments, the PCR-based method comprises emulsion PCR. In some embodiments, the PCR-based method comprises droplet PCR. In some embodiments, the PCR-based method comprises hot start PCR. In some embodiments, the PCR-based method comprises in situ PCR. In some embodiments, the PCR-based method comprises inverse PCR. In some embodiments, the PCR-based method comprises multiplex PCR. In some embodiments, the PCR-based method comprises Variable Number of Tandem Repeats (VNTR) PCR. In some embodiments, the PCR-based method comprises asymmetric PCR. In some embodiments, the PCR-based method comprises long PCR. In some embodiments, the PCR-based method comprises nested PCR. In some embodiments, the PCR-based method comprises hemi-nested PCR. In some embodiments, the PCR-based method comprises touchdown PCR. In some embodiments, the PCR-based method comprises assembly PCR. In some embodiments, the PCR-based method comprises colony PCR. In some embodiments, amplifying comprises a non-PCR-based method. In some embodiments, the non-PCR-based method comprises multiple displacement amplification (MDA). In some embodiments, the non-PCR-based method comprises transcription-mediated amplification (TMA). In some embodiments, the non-PCR-based method comprises nucleic acid sequence-based amplification (NASBA). In some embodiments, the non-PCR-based method comprises strand displacement amplification (SDA). In some embodiments, the non-PCR-based method comprises real-time SDA. In some embodiments, the non-PCR-based method comprises rolling circle amplification. In some embodiments, the non-PCR-based method comprises circle-to-circle amplification. In some embodiments, at least 2 different nucleic acid template molecules are analyzed. In some embodiments, at least 3 different nucleic acid template molecules are analyzed. In some embodiments, at least 4 different nucleic acid template molecules are analyzed. In some embodiments, at least 5 different nucleic acid template molecules are analyzed. In some embodiments, at least 6 different nucleic acid template molecules are analyzed. In some embodiments, at least 7 different nucleic acid template molecules are analyzed. In some embodiments, at least 8 different nucleic acid template molecules are analyzed. In some embodiments, at least 9 different nucleic acid template molecules are analyzed. In some embodiments, at least 10 different nucleic acid template molecules are analyzed. In some embodiments, at least 15 different nucleic acid template molecules are analyzed. In some embodiments, at least 20 different nucleic acid template molecules are analyzed. In some embodiments, at least 25, at least 30, at least 35, at least 40, at least 45, at least 50, at least 55, at least 60, at least 65, at least 70, at least 75, at least 80, at least 85, at least 90, at least 95, at least 100, at least 125, at least 150, at least 175, at least 200, at least 250, at least 300, at least 350, or at least 400 different nucleic acid template molecules are analyzed. In some embodiments, at least 500 different nucleic acid template molecules are analyzed. In some embodiments, at least 1,000 different nucleic acid template molecules are analyzed. In some embodiments, at least 5,000 different nucleic acid template molecules are analyzed. In some embodiments, at least 10,000 different nucleic acid template molecules are analyzed. In some embodiments, at least 20,000 different nucleic acid template molecules are analyzed. In some embodiments, at least 30,000 different nucleic acid template molecules are analyzed. In some embodiments, at least 40,000 different nucleic acid template molecules are analyzed. In some embodiments, at least 50,000 different nucleic acid template molecules are analyzed. In some embodiments, at least 60,000 different nucleic acid template molecules are analyzed. In some embodiments, at least 70,000 different nucleic acid template molecules are analyzed. In some embodiments, at least 80,000 different nucleic acid template molecules are analyzed. In some embodiments, at least 90,000 different nucleic acid template molecules are analyzed. In some embodiments, at least 100,000 different nucleic acid template molecules are analyzed. In some embodiments, the Primer IDs are attached to the nucleic acid template molecules simultaneously. In some embodiments, the Primer IDs are attached to the nucleic acid template molecules sequentially. In some embodiments, the nucleic acid template molecules are amplified and/or detected simultaneously. In some embodiments, the nucleic acid template molecules are amplified and/or detected sequentially. In some embodiments, the Primer ID comprises 5-100 nucleotides. In some embodiments, the Primer ID comprises 5-50 nucleotides. In some embodiments, the Primer ID comprises at least 6 nucleotides. In some embodiments, the Primer ID comprises at least 7 nucleotides. In some embodiments, the Primer ID comprises at least 8 nucleotides. In some embodiments, the Primer ID comprises at least 9 nucleotides. In some embodiments, the Primer ID comprises at least 10 nucleotides. In some embodiments, the Primer ID comprises at least 12 nucleotides. In some embodiments, the Primer ID comprises at least 15 nucleotides. In some embodiments, the Primer ID comprises at least 20 nucleotides. In some embodiments, the Primer ID comprises at least 25 nucleotides. In some embodiments, the Primer ID comprises at least 35 nucleotides.

Disclosed herein is a method to analyze nucleic acid sequences, comprising (a) attaching a Primer ID to a first end of each of a plurality of nucleic acid fragments to form tagged-nucleic acid templates; (b) redundantly determining nucleotide sequence of a tagged-nucleic acid template, wherein determined nucleotide sequences which share a Primer ID form a family of members; and (c) identifying a nucleotide sequence as accurately representing an analyte nucleic acid fragment when at least 1% of members of the family contain the sequence.

The nucleotide sequence may be identified when at least 5% of members of the family contain the sequence. The nucleotide sequence may be identified when at least 10%, 15%, 20%, 25%, 30%, 35%, 40%, 45%, 50%, 55%, 60%, 65%, 70%, 75%, 80%, 85%, 90%, 92%, 95%, 97%, 98%, 99% or more of members of the family contain the sequence. The nucleotide sequence may be identified when at least about 75% to about 99% of members of the family contain the sequence. The nucleotide sequence may be identified when at least about 85% to about 99% of members of the family contain the sequence. The nucleotide sequence may be identified when at least about 92% to about 98% of members of the family contain the sequence.

A first universal priming site may be attached to a second end of each of a plurality of analyte nucleic acid fragments.

At least two cycles of polymerase chain reaction may be performed such that a family may be formed of tagged-nucleic acid templates that have a Primer ID on the first end and a first universal priming site on a second end.

The Primer ID may be covalently linked to a second universal priming site. The Primer ID may be attached to the 5' end of a nucleic acid fragment and the second universal priming site may be 5' to the Primer ID. The Primer ID may be attached to the 3' end of a nucleic acid fragment and the second universal priming site may be 3' to the Primer ID.

The nucleic acid fragments may be formed by applying a shear force to a nucleic acid. Alternatively, the nucleic acid fragments may be formed by one or more restriction endonucleases.

The method may further comprise, prior to the step of redundantly determining, amplifying the tagged-nucleic acid templates. The method may further comprise, prior to the step of redundantly determining, amplifying the tagged-nucleic acid templates by using a pair of primers which may be complementary to the first and the second universal priming sites, respectively.

The method may further comprise, prior to the step of redundantly determining, amplifying the tagged-nucleic acid templates, and wherein prior to said amplification, a single strand-specific exonuclease may be used to digest excess primers used to attach the Primer ID the nucleic acid fragments.

The method may further comprise, prior to the step of redundantly determining, amplifying the tagged-nucleic acid templates, and wherein prior to said amplification, the single strand-specific exonuclease may be inactivated, inhibited, or removed. The single strand-specific exonuclease may be inactivated by heat treatment.

The primers used in said amplification may comprise one or more chemical modifications rendering them resistant to exonucleases. The primers used in said amplification may comprise one or more phosphorothioate linkages.

The method may further comprise, prior to the amplification step, treating the DNA with bisulfite to convert unmethylated cytosine bases to uracil.

The method may further comprise the step of comparing number of families representing a first DNA fragment to number of families representing second DNA fragment to determine a relative concentration of a first DNA fragment to a second DNA fragment in the plurality of DNA fragments.

Disclosed herein is a method to analyze nucleic acid sequences, comprising (a) attaching a Primer ID to a first end of each of a plurality of DNA fragments using at least two cycles of amplification with first and second primers to form tagged-DNA fragments, wherein the Primer IDs are in excess of the DNA fragments during amplification, wherein the first primers comprise (i) a first segment complementary to a desired amplicon; (ii) a second segment containing the Primer ID; and (iii) a third segment containing a universal priming site for subsequent amplification; and wherein the second primers comprise a universal priming site for subsequent amplification; wherein each cycle of amplification attaches one universal priming site to a strand; (b) amplifying the tagged-DNA fragments to form a family of tagged-DNA fragments from each tagged-DNA fragment; and (c) determining nucleotide sequences of a plurality of members of the family.

The method may further comprise the steps of (d) comparing sequences of a family of tagged-DNA fragments; and (e) identifying a nucleotide sequence as accurately representing an DNA fragment when at least 1% of members of the family contain the sequence.

The nucleotide sequence may be identified when at least 5% of members of the family contain the sequence. The nucleotide sequence may be identified when at least 10%, 15%, 20%, 25%, 30%, 35%, 40%, 45%, 50%, 55%, 60%, 65%, 70%, 75%, 80%, 85%, 90%, 92%, 95%, 97%, 98%, 99% or more of members of the family contain the sequence. The nucleotide sequence may be identified when at least about 75% to about 99% of members of the family contain the sequence. The nucleotide sequence may be identified when at least about 85% to about 99% of members of the family contain the sequence. The nucleotide sequence may be identified when at least about 92% to about 98% of members of the family contain the sequence.

The second primers may each comprise a Primer ID.

The Primer IDs may be from 2 to 4000 bases or base pairs inclusive. The Primer IDs may be from 20 to 100 bases or base pairs inclusive. The Primer IDs may be from 20 to 80 bases or base pairs inclusive. The Primer IDs may be from 20 to 60 bases or base pairs inclusive. The Primer IDs may be at least about 10, 15, 20, 25, 30, 35, 40, 45, 50, 60, 70, 80, 90, 100 or more bases or base pairs. The Primer IDs may be at least about 125, 150, 175, 200, 250, 300, 350, 400, 450, 500 or more bases or base pairs. The Primer IDs may be less than about 400, 300, 200, 100, 90, 80, 70, 60 or fewer bases or base pairs.

The method may further comprise, prior to the step of amplifying the tagged-DNA fragments, digesting excess primers used to attach the Primer ID the DNA fragments with a single strand-specific exonuclease. The method may further comprise, prior to the step of amplifying, inactivating, inhibiting or removing the single strand-specific exonuclease. The single strand-specific exonuclease may be inactivated by heat treatment. The primers used in the step of amplifying may comprise one or more phosphorothioate linkages.

The method may further comprise, prior to the amplification step, treating the DNA with bisulfite to convert unmethylated cytosine bases to uracil. The method may further comprise the step of comparing number of families representing a first DNA fragment to number of families representing second DNA fragment to determine a relative concentration of a first DNA fragment to a second DNA fragment in the plurality of DNA fragments.

Disclosed herein is a method to analyze DNA using endogenous unique identifiers, comprising (a) attaching adapter oligonucleotides to ends of fragments of DNA of between 30 to 2000 bases, inclusive, to form adapted fragments, wherein each end of a fragment before said attaching is an endogenous unique identifier for the fragment; (b) amplifying the adapted fragments using primers complementary to the adapter oligonucleotides to form families of adapted fragments; (c) determining nucleotide sequence of a plurality of members of a family; comparing nucleotide sequences of the plurality of members of the family; and (d) identifying a nucleotide sequence as accurately representing an DNA fragment when at least 1% of members of the family contain the sequence.

The method may further comprise enriching for fragments representing one or more selected genes by means of capturing a subset of the fragments using capture oligonucleotides complementary to selected genes in the DNA.

The method may further comprise enriching for fragments representing one or more selected genes by means of amplifying fragments complementary to selected genes.

The step of attaching may be prior to the step of enriching.

The fragments may be formed by shearing. The fragments may be formed by digestion with one or more restriction enzymes.

The nucleotide sequence may be identified when at least 5% of members of the family contain the sequence. The nucleotide sequence may be identified when at least 10%, 15%, 20%, 25%, 30%, 35%, 40%, 45%, 50%, 55%, 60%, 65%, 70%, 75%, 80%, 85%, 90%, 92%, 95%, 97%, 98%, 99% or more of members of the family contain the sequence. The nucleotide sequence may be identified when at least about 75% to about 99% of members of the family contain the sequence. The nucleotide sequence may be identified when at least about 85% to about 99% of members of the family contain the sequence. The nucleotide sequence may be identified when at least about 92% to about 98% of members of the family contain the sequence.

The method may further comprise, prior to the amplification step, treating the DNA with bisulfite to convert unmethylated cytosine bases to uracil.

The method may further comprise the step of comparing number of families representing a first DNA fragment to number of families representing second DNA fragment to determine a relative concentration of a first DNA fragment to a second DNA fragment in the plurality of DNA fragments.

Disclosed herein is a population of primer pairs, wherein each pair comprises a first and second primer for amplifying and identifying a gene or gene portion, wherein (a) the first primer comprises a first portion of 10-100 nucleotides complementary to the gene or gene portion and a second portion of 10 to 100 nucleotides comprising a site for hybridization to a third primer; (b) the second primer comprises a first portion of 10-100 nucleotides complementary to the gene or gene portion and a second portion of 10 to 100 nucleotides comprising a site for hybridization to a fourth primer, wherein interposed between the first portion and the second portion of the second primer is a third portion consisting of 2 to 4000 nucleotides forming a Primer ID, wherein the Primer IDs in the population have at least 4 different sequences, wherein the first and second primers are complementary to opposite strands of the gene or gene portion.

The first portion of the first primer and/or the first portion of the second primer may comprise at least about 10, 15, 20, 25, 30 or more nucleotides complementary to the gene or gene portion. The first portion of the first primer and/or the first portion of the second primer may comprise less than about 80, 70, 60, 50 or fewer nucleotides complementary to the gene or gene portion. The first portion of the first primer and/or the first portion of the second primer may comprise between about 10 to about 90, between about 10 to about 80, between about 10 to about 70, between about 10 to about 60 nucleotides complementary to the gene or gene portion.

The first primer may further comprise a Primer ID.

The Primer IDs in the population can have at least at least 10, 15, 20, 25, 30, 35, 40, 45, 50, 60, 70, 80, 90, 100, 200, 300, 400, 500, 600, 700, 800, 900, 1000 or more different sequences. The Primer IDs in the population can have at least at least 2,000; 3,000; 4,000; 5,000; 6,000; 7,000; 8,000; 9,000; 10,000; 15,000; 20,000; 25,000; 30,000; 35,000; 40,000; 45,000; 50,000; 60,000; 70,000; 80,000; 90,000; 100,000; 200,000; 300,000; 400,000; 500,000; 600,000; 700,000; 800,000; 900,000; 1,000,000 or more different sequences.

Further disclosed herein is a kit comprising a population of primer primers, wherein each pair comprises a first and second primer for amplifying and identifying a gene or gene portion, wherein (a) the first primer comprises a first portion of 10-100 nucleotides complementary to the gene or gene portion and a second portion of 10 to 100 nucleotides comprising a site for hybridization to a third primer; (b) the second primer comprises a first portion of 10-100 nucleotides complementary to the gene or gene portion and a second portion of 10 to 100 nucleotides comprising a site for hybridization to a fourth primer, wherein interposed between the first portion and the second portion of the second primer is a third portion consisting of 2 to 4000 nucleotides forming a Primer ID, wherein the Primer IDs in the population have at least 4 different sequences, wherein the first and second primers are complementary to opposite strands of the gene or gene portion.

The kit may further comprise third and fourth primers complementary to the second portions of each of the first and second primers. The first portion of the first primer and/or the first portion of the second primer may comprise at least about 10, 15, 20, 25, 30 or more nucleotides complementary to the gene or gene portion. The first portion of the first primer and/or the first portion of the second primer may comprise less than about 80, 70, 60, 50 or fewer nucleotides complementary to the gene or gene portion. The first portion of the first primer and/or the first portion of the second primer may comprise between about 10 to about 90, between about 10 to about 80, between about 10 to about 70, between about 10 to about 60 nucleotides complementary to the gene or gene portion.

The first primer may further comprise a Primer ID. The Primer IDs in the population can have at least at least 10, 15, 20, 25, 30, 35, 40, 45, 50, 60, 70, 80, 90, 100, 200, 300, 400, 500, 600, 700, 800, 900, 1000 or more different sequences. The Primer IDs in the population can have at least at least 2,000; 3,000; 4,000; 5,000; 6,000; 7,000; 8,000; 9,000; 10,000; 15,000; 20,000; 25,000; 30,000; 35,000; 40,000; 45,000; 50,000; 60,000; 70,000; 80,000; 90,000; 100,000; 200,000; 300,000; 400,000; 500,000; 600,000; 700,000; 800,000; 900,000; 1,000,000 or more different sequences.

The invention provides kits for detecting and/or measuring types and/or levels. In one non-limiting embodiment, kits for carrying out diagnostic assays of the invention typically include, a suitable container means, (i) a probe that comprises a nucleic acid sequence (including Primer ID and optionally barcode) that specifically binds to a polynucleotide of interest; (ii) a label for detecting the presence of the probe; and (iii) instructions for how to use and/or interpret the results. The container means of the kits will generally include at least one vial, test tube, flask, bottle, syringe and/or other container into which a nucleic acid specific for one of a polynucleotide of interest of the present invention may be placed and/or suitably aliquoted. Where a second and/or third and/or additional component is provided, the kit will also generally contain a second, third and/or other additional container into which this component may be placed. Alternatively, a container may contain a mixture of more than one nucleic acid reagent, each reagent specifically binding a different marker in accordance with the present invention. The kits of the present invention will also typically include means for containing the nucleic acid probes in close confinement for commercial sale. Such containers may include injection and/or blow-molded plastic containers into which the desired vials are retained.

The kits may further comprise positive and negative controls, as well as instructions for the use of kit components contained therein, in accordance with the methods of the present invention. The kit may also include a package insert with instructions in connection with an approved indication.

The Primer ID may comprise randomly selected sequences. The Primer ID may comprise pre-defined nucleotide sequences. The Primer ID may comprise both randomly selected sequences and pre-defined nucleotides.

The method may further comprise, prior to the amplification step, treating the DNA with bisulfite to convert unmethylated cytosine bases to uracil.

The method may further comprise the step of comparing number of families representing a first DNA fragment to number of families representing second DNA fragment to determine a relative concentration of a first DNA fragment to a second DNA fragment in the plurality of DNA fragments. See also, Jabara et al. 2011 PNAS 20166-20171, the contents of which are hereby incorporated in its entirety.

Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps. The present invention may suitably "comprise", "consist of", or "consist essentially of", the steps, elements, and/or reagents described in the claims.

It is further noted that the claims may be drafted to exclude any optional element. As such, this statement is intended to serve as antecedent basis for use of such exclusive terminology as "solely", "only" and the like in connection with the recitation of claim elements, or the use of a "negative" limitation.

The following Examples further illustrate the invention and are not intended to limit the scope of the invention. In particular, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

EXAMPLES

Example 1

Use of Primer IDs for the Analysis of a Viral Template Molecule

High throughput sequencing allows the acquisition of large amounts of sequence data that can encompass entire genomes. With sufficient amounts of starting DNA, PCR is not needed before the library preparation step of the sequencing protocol. Sequencing miscalls inherent in high throughput sequencing approaches are resolved using multiple reads over a given base.

Deep sequencing can also capture the genetic diversity of viral populations, including intrahost populations derived from clinical samples. This approach offers the opportunity to view population diversity and dynamics and viral evolution in unprecedented detail. One place where the presence of minor variants is of immediate practical importance is in the detection of drug-resistant variants. Standard bulk sequencing methods typically miss allelic variants below 20% in frequency within a population. Alternative assays can detect less abundant variants that confer drug resistance, but require a priori selection of sites and variants. Thus, deep sequencing approaches offer the opportunity to identify minor variants associated with resistance de novo with the goal of understanding their role in therapy failure.

Although screening for drug-resistant variants is a practical application of the deep sequencing technology, this technology also addresses broader questions of sequence diversity and structure for a complex population like HIV-1. However, the relatively high sequencing error rates of these technologies artificially increase genetic diversity, which confounds the detection of natural genetic variation especially when sequencing a highly heterogeneous viral population. Moreover, the use of PCR to amplify the amount of material before starting the sequencing protocol adds the potential for several serious artifacts: First, nucleotide misincorporation by the polymerase during many rounds of amplification artificially increases sequence diversity; second, artifactual recombination during amplification occurs when premature termination products prime a subsequent round of synthesis, which can obscure the linkage of two sequence polymorphisms; third, differential amplification can skew allelic frequencies; and fourth, PCR amplification can create a significant mass of DNA from a small number of starting templates, which obscures the true sampling of the original population as these few starting templates/genomes get resampled in the PCR product, creating sequence resampling rather than the observation of independent genomes. Overall, these biases artificially decrease true diversity while introducing artifactual diversity and also skew allelic frequencies, which can lead to incongruence between the real and observed viral populations. Most investigators use statistical tools to attempt to control for the types of sequencing errors that are associated with each sequencing platform.

To make deep sequencing useful for complex populations, it is necessary to overcome PCR resampling, which is mistaken for sampling of the original population, and PCR and sequencing errors, which can be mistaken for diversity. As nucleotide misincorporation is largely random across sites and template switching/recombination is more likely to occur in the later cycles of a PCR, strategies that create a bulk or consensus sequence for each sampled template will call the correct base at each position. One approach to sampling highly heterogeneous populations, such as the HIV-1 env gene, is through endpoint dilution titration of the template before nested PCR, such that a single template is present in each PCR amplification. In addition to masking the misincorporations, PCR-mediated recombination produces recombinant templates identical to the parental sequence. Although highly accurate, this technique is labor-intensive and, as population sampling is dependent on the number of templates sequenced, this methodology does not lend itself to the identification of minor variants or to understanding the structure of a complex population, nor is it easily adaptable to a high throughput approach.

We have developed a high throughput technique for directly resolving the genetic diversity of a viral population. This technique avoids the recording of PCR and sequencing errors that create artificial diversity, and corrects for artificial allelic skewing and PCR resampling, revealing the original genomes in the population. This is accomplished by embedding a degenerate block of nucleotides within the primer used in the first round of cDNA synthesis. This creates a random library of sequences within the primer population.

As primers are individually used out of this library, each viral template is copied such that the complement (cDNA) now includes a unique sequence tag, or Primer ID. This Primer ID is carried through all of the subsequent manipulations to mark all sequences that derive from each independent templating event, and PCR resampling then becomes over-coverage for each template to create a consensus sequence of that template. Using this approach, we were able to directly remove error, correct for PCR resampling, and capture the fluctuation of minor variants in the viral population within a host. We also resolved minor drug-resistant variants below 1% in frequency before the initiation of antiretroviral therapy, and were able to correlate these variants with the emergence of drug resistance.

Results

A cDNA Synthesis Primer Containing a Primer ID Can Be Used to Track Individual Viral Templates. A population of cDNA synthesis primers was designed to prime DNA synthesis downstream of the HIV-1 protease (pro) gene, with the primer containing two additional blocks of identifying information (FIG. 1A). The first block was a string of eight degenerate nucleotides that created 65,536 distinct sequence combinations, or Primer IDs. This region was flanked by an a priori selected three nucleotide barcode, creating a sample identification block so that multiple samples could be pooled together in a sequencing run. A designed sequence at the 5' end of the cDNA primer was used for subsequent amplification of the cDNA sequences by nested PCR.

Figure 4:
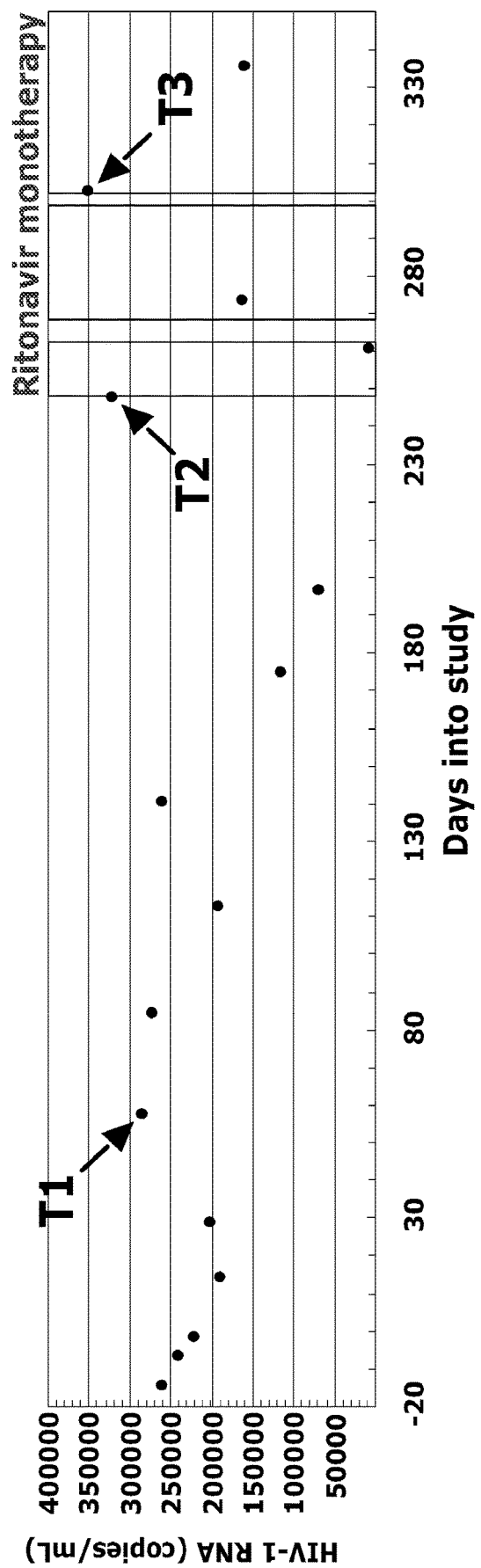
FIG. 4 shows a longitudinal sampling of blood plasma from a single individual infected with HIV-1 subtype B pre- and post- a failed ritonavir monotherapy regime. Two time-points ~6 mo apart were sampled before ritonavir therapy (T1 and T2). One time point was sampled after failed, intermittent ritonavir monotherapy (T3). The shaded areas represent times of therapy compliance based on self-report.
Figure 5:
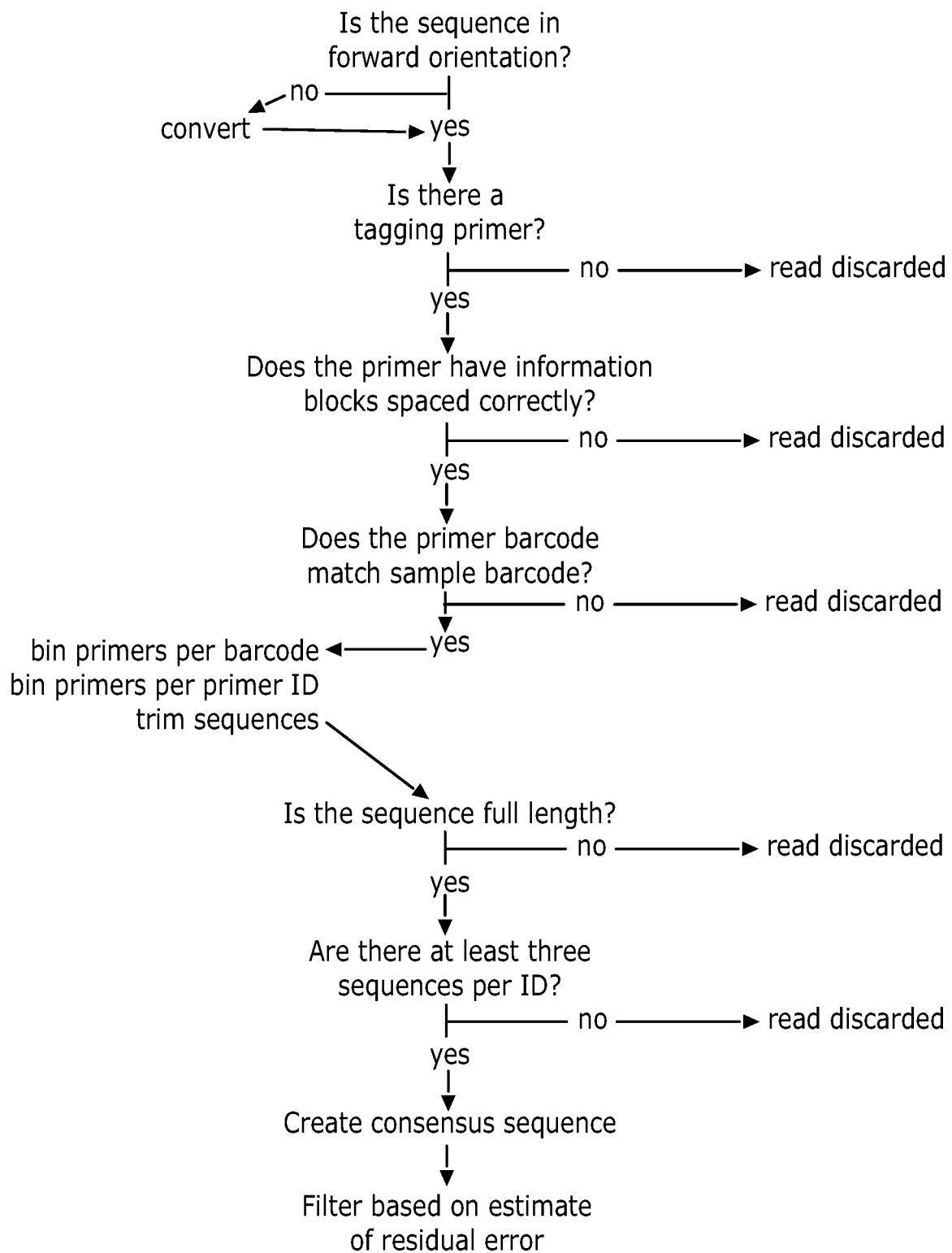
FIG. 5 shows the logic flow of the bioinformatic pipeline that processed raw sequence reads into consensus sequences. First, when applicable, reads were converted to forward orientation. Next, reads were assessed for the cDNA synthesis tagging primer containing correctly spaced sample and primer identifying information (barcode and Primer ID, respectively). Sequences were then binned based on the barcode, and within each barcode, binned by Primer ID, then trimmed to just the protease coding domain. For full-length protease sequences, when at least 3 sequences within a barcode bin contained an identical Primer ID, a consensus sequence was made based on majority-rule and the use of ambiguous nucleotide designations for ties. Sequences were then further filtered based on background estimates of error for the in vitro RT cDNA synthesis and the first round of Taq DNA polymerase synthesis.

Viral RNA was extracted from three longitudinal blood plasma samples from an individual infected with subtype B HIV-1 who was participating in a protease inhibitor efficacy trial (M94-247) (FIG. 4). Approximately 10,000 copies of viral RNA from each sample were used in a reverse transcription reaction for cDNA synthesis and tagging using the Primer ID. The cDNA product was separated from the unused cDNA primers, and then the viral sequences were amplified by nested PCR and sequenced on the 454 GS FLX Titanium. Our data were distilled from total reads of 20,429, 24,658, and 27,075 for the three time points (T1, T2, and T3, respectively). Raw sequence reads were assessed for the cDNA tagging primer and a full length pro gene sequence (297 nucleotides long representing 99 codons), and when three or more sequences within a sample contained an identical Primer ID, a consensus sequence was formed to represent one sequence/genome in the population (FIGS. 1B and 1C and FIG. 5).

Figure 6A:
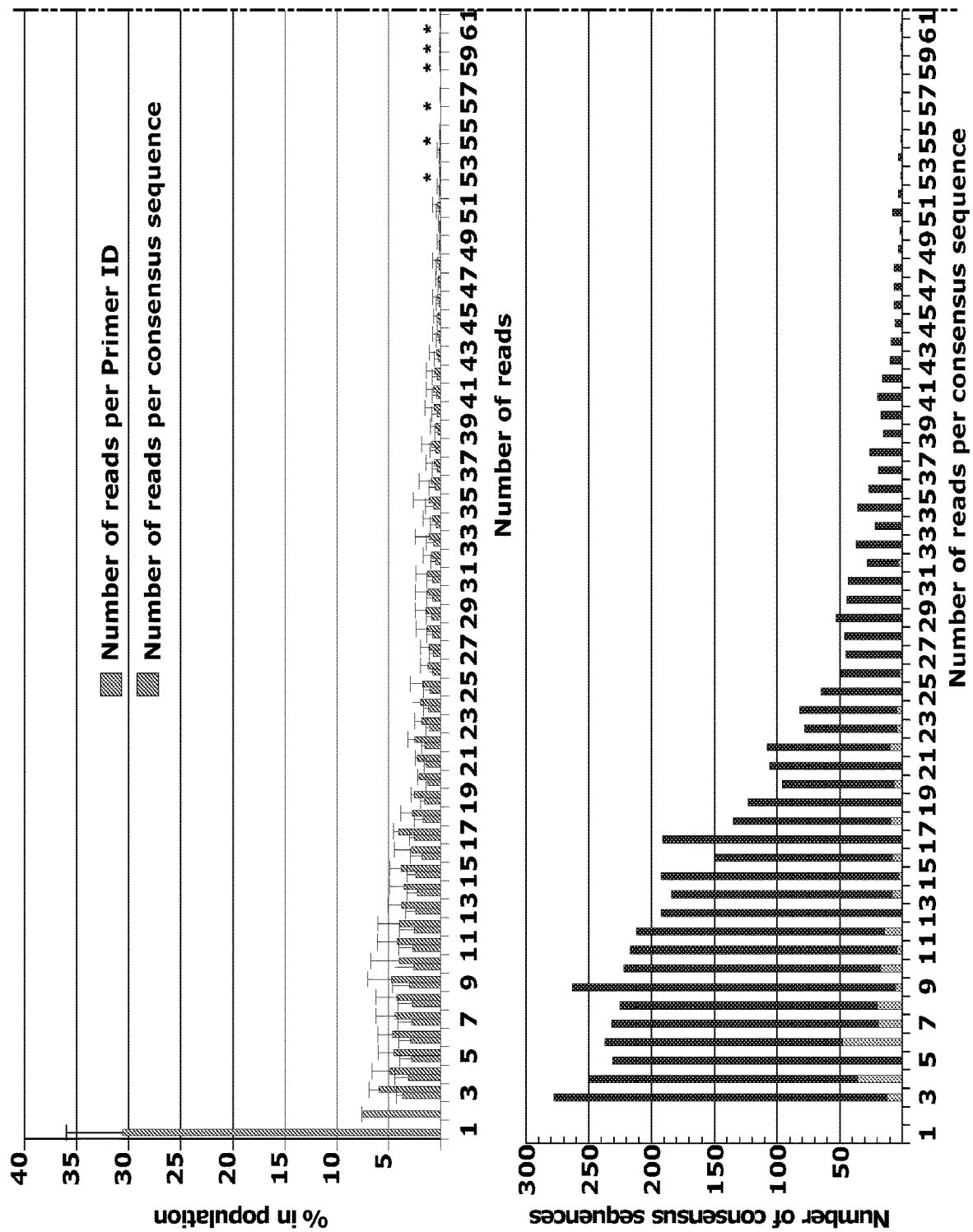
FIG. 6A shows the distribution of the number of reads per Primer ID or consensus sequence. Left gray bars represent the distribution of resampling of the filtered sequence population immediately before consensus sequence generation. Within a single Primer ID, when three or more sequences were present, a consensus sequence was formed. The right gray bars represent the distribution of the number of reads that went into each consensus sequence. The values shown represent the mean for the data from the three time points with the error bars representing the SD between the three samples. Starred bars are included to mark positions where a single sequence had high resampling occurrence.
Figure 7:
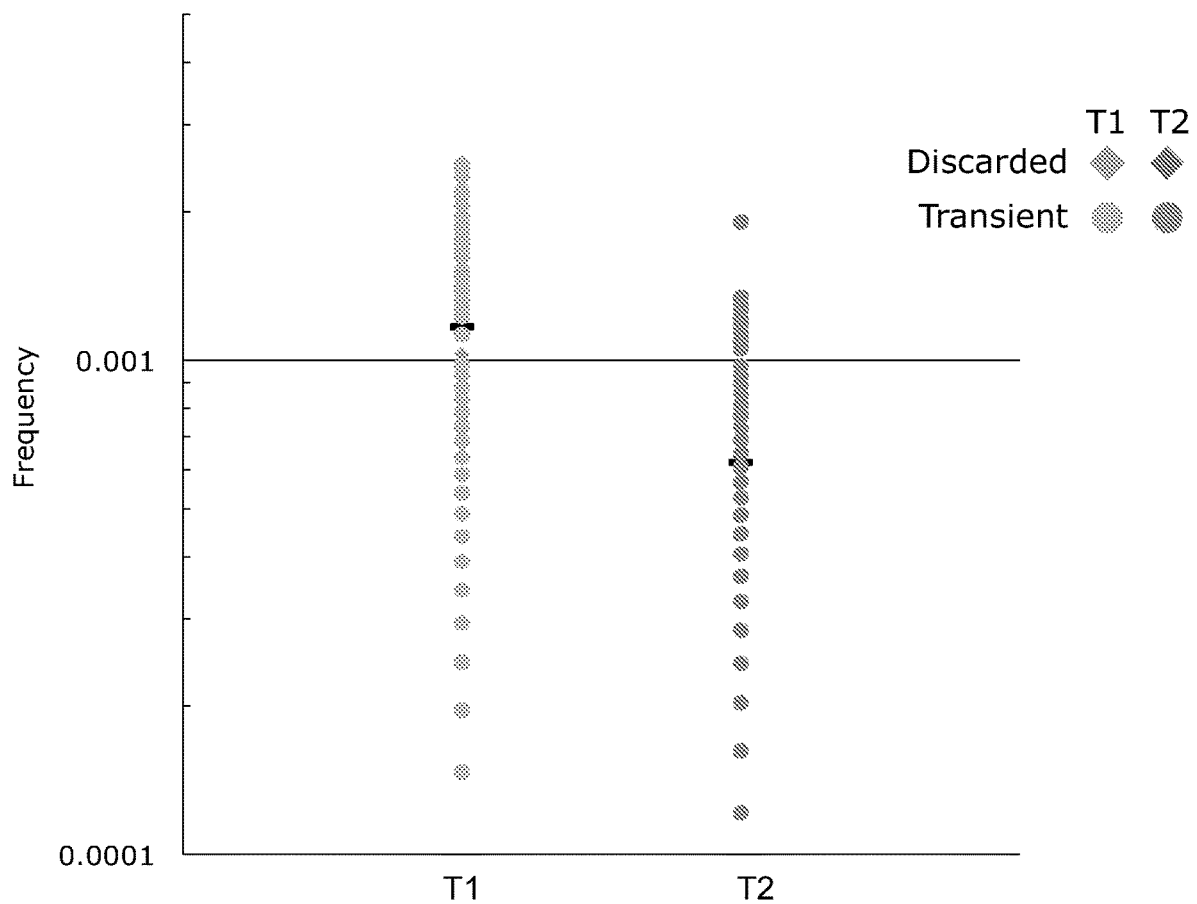
FIG. 7 shows an analysis of low abundance variants for the distribution of allelic skewing. We used discarded sequences (i.e., unique sequences represented by a single Primer ID) and transient genomes defined as having a low abundance SNP in the preconsensus population per untreated time point. Transient sequences were defined as having at least two sequences at only one of the untreated time points, or one copy at one of the untreated time points and then again at the third time point. These sequences were used to define a set of sequences that could be compared for low frequency abundance in the total data set versus the consensus sequences. The horizontal bars represent the measured frequency of a single copy sequences in the consensus population at T1 and T2. Dark points represent discarded genomes, and light points represent transient genomes with their position indicating their abundance in the total sequence population before construction of the consensus sequences. Light gray points represent sequences present at T1, darker gray points represent sequences present at T2. These data show that allelic skewing of 2-fold upward and 10-fold downward is common before the formation of the consensus sequence.

With these manipulations we generated 857, 1,609, and 2,213 consensus sequences, respectively, for the three time points (FIG. 1C). The median number of reads per Primer ID was 6, ranging from 1 to 96 (FIG. 6A). The distribution of identical Primer IDs did not form a normal distribution as would be expected if all templates were amplified equally. We saw a higher than expected number of single reads of Primer IDs; although we do not know the reason for this, such a result is consistent with different cDNA templates entering the PCR at different cycles. Because each template is individually tagged the different number of reads is an indication of allelic skewing, as noted this can be nearly 100-fold. In an analysis of a number of low abundant variants we saw a 20-fold range of representation through allelic skewing, with half of the variants up to 2- to 3-fold more abundant than the mean, and the other half up to 5- to 10-fold less abundant (FIG. 7).

We conservatively estimate the combined in vitro error rate of the cDNA synthesis step by reverse transcriptase (RT) and the first strand synthesis by the Taq polymerase to be on the order of 1 mutation in 10,000 bases, or approximately one mutation per 33 pro gene sequences, based on an RT error rate of 1 in 22,000 nucleotides (38) and a Taq polymerase error rate of 1.1 in 10,000 nucleotides (39) but reduced by half because only the first round of synthesis is relevant and a misincorporation at this step gives a mixture. Later rounds of Taq polymerase errors should be largely lost through the creation of the consensus sequence. Thus, we would expect 139 sequence misincorporations to be present in the data set of 4,679 total sequences representing T1+T2+T3, and with an excess of transitions. These would be expected to occur as 113 single copy single-nucleotide polymorphisms (SNPs) and 13 SNPs that appeared twice. We observed 98 single copy SNPs in the data set with a threefold excess of transitions, and with three-fourths of them being coding changes, which is consistent with random mutations. We expect there to be low frequency SNPs in the viral population from rare but persistent variants that are fortuitously sampled, and from the intrinsic error rate of viral replication (the error rate during one round of viral replication would represent approximately one mutation per 150 pro gene sequences). However, we cannot distinguish real polymorphisms from the inferred background error rate associated with the first and second rounds of in vitro DNA synthesis. Thus, we have limited the analysis of population diversity to SNPs that appeared at least twice in the data set (e.g., linked to at least two separate Primer IDs), either at the same time point or at multiple time points in the overall data set (Table 1). We have not corrected the data set for the presumed 13 SNPs that appeared twice that are expected to be present due to error even though this represents 33% of all of the SNPs that appeared twice (13 of 39). Overall, 80% of the SNPs (e.g., any sequence change from the consensus that appeared at least once) in the total data set of 72,162 sequence reads were removed as error. Also, 60-65% of the sequence reads were revealed as resampling. Finally, allelic skewing of up to nearly 100 fold was corrected (FIG. 7).

Figure 2B:
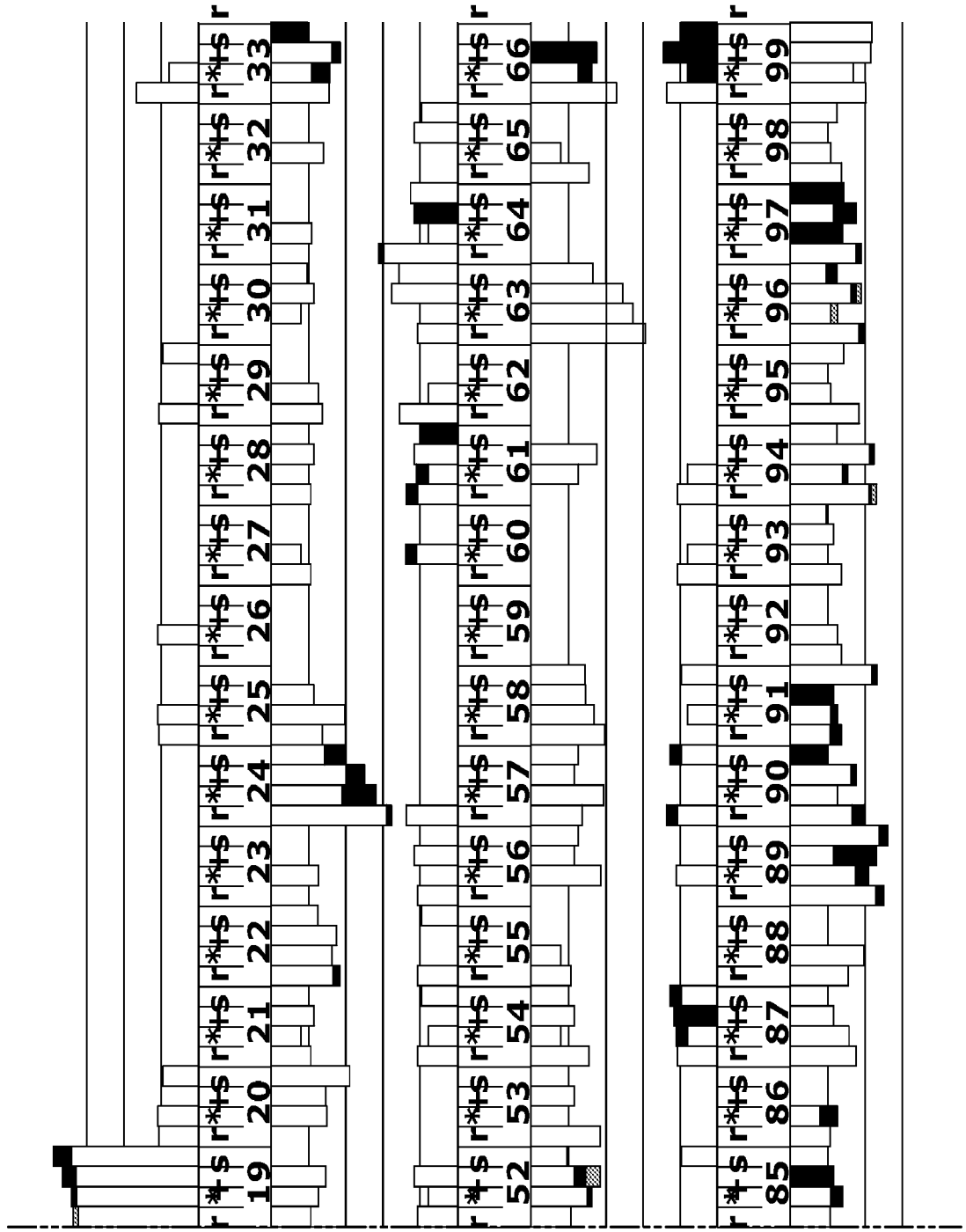
Figure 8B:
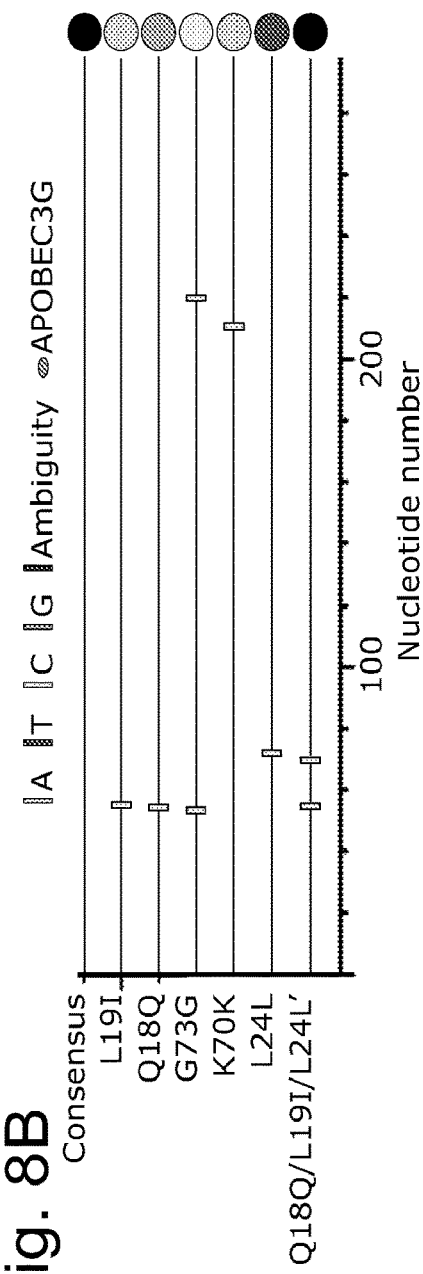
FIG. 8A-8C shows the major and minor allelic variants in the untreated populations.
Figure 8C:
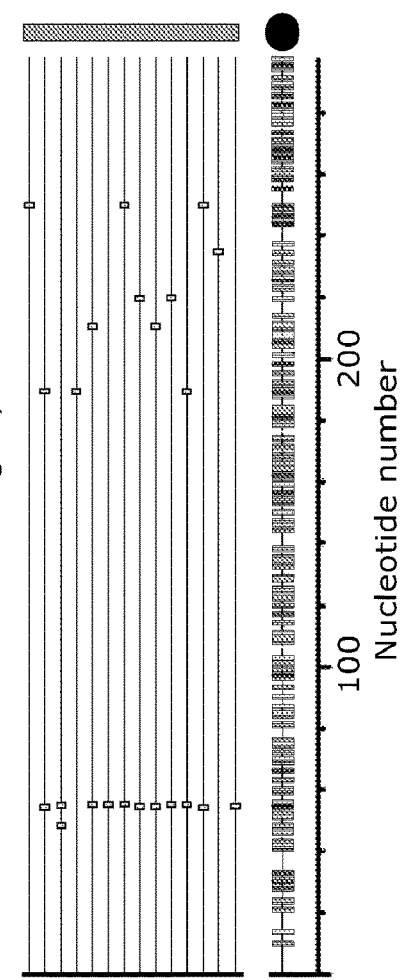
Figure 8A:
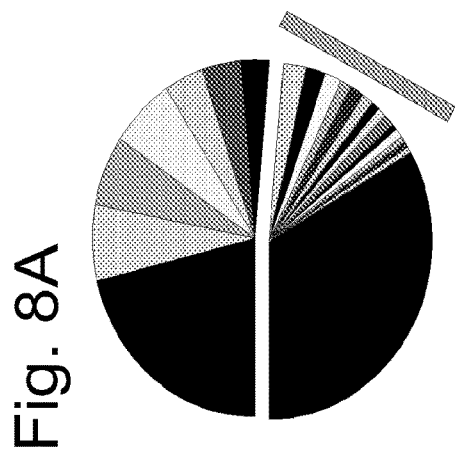

Longitudinal Sequencing of the HIV-1 Protease (pro) Gene in an Untreated Individual Reveals Dynamic Changes in Genetic Variation. We analyzed the sequences of the pro gene populations to assess allelic frequency at the two sampled time points, separated by 6 mo and before ritonavir (37) drug selection (FIG. 4). The combined sequence population from the two time points (T1 and T2) before therapy consisted of 492 unique pro gene sequences with 155 SNPs. About 4% (e.g., 21) of these unique gene sequences were above 0.5% abundance, and these 21 unique gene sequences represented 67% of all sampled genomes, with the genome representing the overall consensus sequence comprising 21% of the total population (FIGS. 8A and 8B). The relatively small number of unique gene sequences above 0.5% frequency in the population contained only 7% of the 155 detected SNPs. Thus, a large proportion of the viral population's diversity was associated with a large number of pro gene sequences that were present at low abundance (FIGS. 8A and 8C); conversely, the majority of the population consisted of a small number of SNPs. Similarly, Tajima's D statistic for T1 and T2 in this individual were −2.35 and −2.31, respectively (Table 2), indicative of a population structure that has an excess of low frequency polymorphisms. This pattern is consistent with but more extreme than that observed in a prior shallow intrahost survey in which a metapopulation model was proposed to explain the pattern of Tajima's D statistic (40). FIG. 2A-2B shows the encoded amino acid variability and synonymous nucleotide variability present in two or more individual genomes across the 99 codons in the pro gene for these samples.

Synonymous variability. There were 57 codons (with 63 variants/SNPs) that contained synonymous diversity that appeared in both pretherapy time points, and 30 codons (with 31 variants) that appeared in only one time point. Taken together, 75 of the 99 codons contained some level of synonymous diversity (FIG. 2A-2B and Table 1). Of the 63 variants that were present in both untreated time points, 92% were transitions. Of the 31 variants that appeared in only one of the time points, 71% were transitions, representing a significantly smaller fraction of transitions than among the synonymous variants that appeared at both time points (P=0.012; Fisher's exact test). This suggests that synonymous transversions are selected against over time.

Nonsynonymous variability. There were 26 codons (28 variants) that contained coding variability that appeared in both pretherapy time points, and an additional 28 codons (33 variants) with nonsynonymous changes found in only one of the time points. Taken together, 49 of the 99 codons contained some level of nonsynonymous diversity (FIG. 2A-2B and Table 1). For the 28 nonsynonymous variants detected at both time points, 22 were transitions, and these mostly represented conservative amino acid changes. In the case of synonymous mutations two-thirds of the variants were present at both time points, whereas in the case of nonsynonymous mutations, less than half were present at both time points (P=0.012; Fisher's exact test). This observation suggests that, at this level of sequence sampling, we are able to see a difference in stability within the population in comparing synonymous and nonsynonymous substitutions.

Genetic fluctuation. We compared the stability of minor SNPs present at both T1 and T2. A total of 14 of the 91 SNPs (synonymous and nonsynonymous that appeared at both time points) had significant changes in abundance between the two time points ($\chi 2$ test with a false discovery rate of 0.05). Of the 14 SNPs with significant changes in abundance, 11 had a decrease in the abundance, with an average decrease around 7.5-fold. There were three SNPs that had a significant increase in abundance, all of which were synonymous, ranging from a 4- to 47-fold increase. Although a majority of SNPs that changed in abundance had a decrease in the frequency between T1 and T2, on a population level, there was not a large change in diversity between the two time points (T1 $\pi$=0.0080, T2 $\pi$=0.0079; Table 2). However, the trend of increased abundance at the three sites may be driven by selection of cryptic epitopes in an alternative reading frame (see Discussion).

Figure 3:
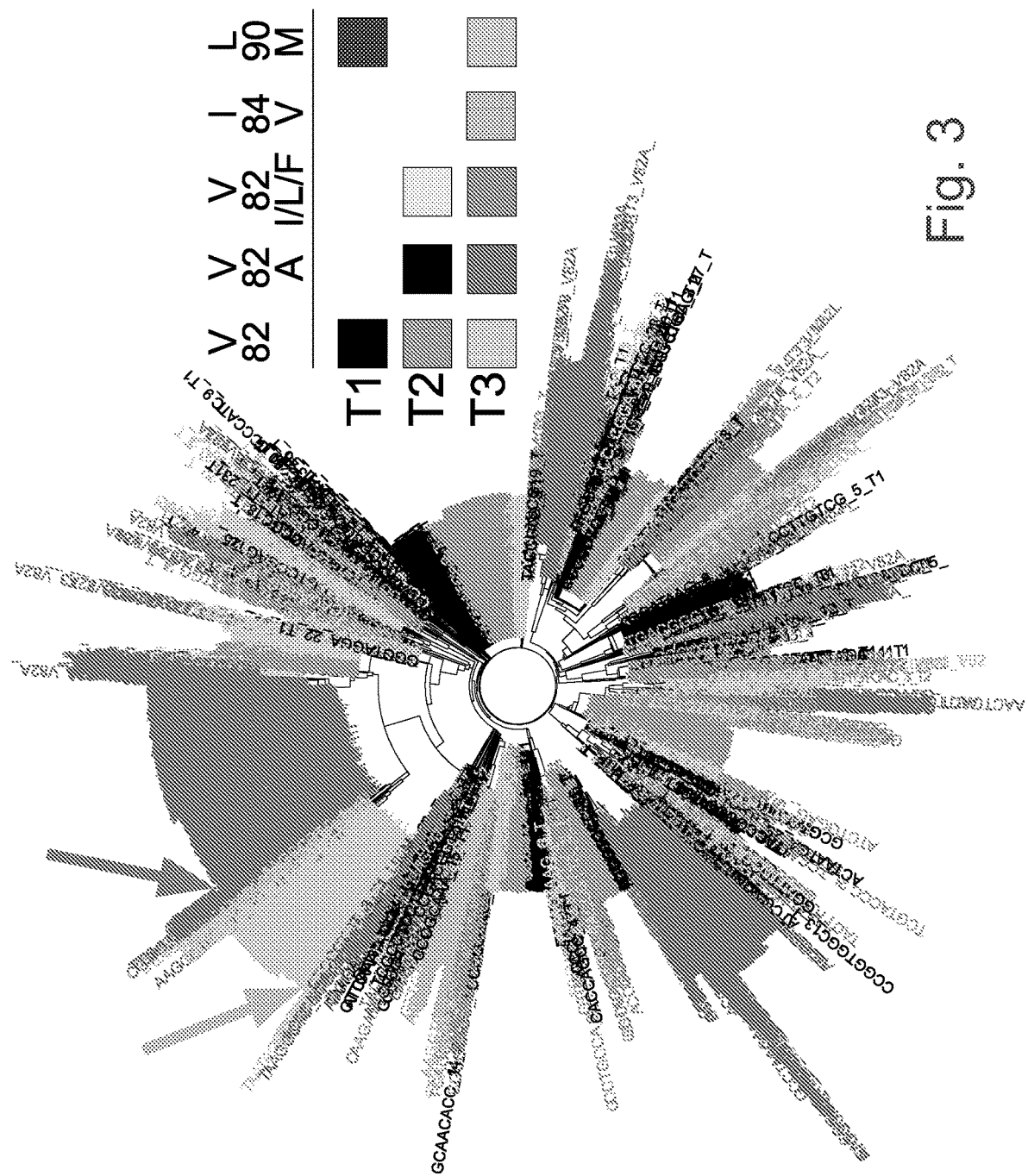
FIG. 3 shows phylogenetic representation of protease population derived from deep sequencing with a Primer ID. A Neighbor-Joining tree was constructed from sequences derived from all three time points and colored based on susceptibility to ritonavir. V82 taxa represent susceptible variants (defined as not V82A/I/L/F, I84V, or L90M). V82A taxa represent variants containing the major ritonavir resistant variant, V82A. Other taxa represent the minor resistant variants V82I/L/F and the minor resistant alleles L90M and I84V, respectively. Within a group brightness is correlated with sample time. Dark arrows point to pre-RTV low-abundance sequences that clonally amplified to their respective clades.

Significance of rare variants. We observed two extremes in terms of biological relevance in the untreated population among variants detected as at least two independent sequences across the three time points. At one extreme was the detection of nonviable genomes in the form of a coding variant at position 25, which mutates the active site of the protease, and the detection of termination codons at positions 42 and 61 (Table 1). At the other extreme was the detection of the L90M and V82A variants (at time points 1 and 2, respectively) that became the major resistance populations after ritonavir therapy was initiated (see below, FIG. 3); in addition, V82I and V82L were detected at T2. We found two more examples of primary resistance mutations at low abundance, K20R at all three time points and M46I at two time points, but these did not grow out in the presence of ritonavir (FIG. 3 and Table 1). Similarly, fitness compensatory mutations were also detected at low abundance (L10F, M36I, L63P, A71T, and V77I), all below 1%, and only L63P increased (modestly) in abundance after exposure to ritonavir. More generally, of the 28 substitutions most closely associated with protease inhibitor drug resistance, we found 10 such variants, half of which were detected at both pretherapy time points (Table 1).

Assessment of Linkage Disequilibrium (LD) Within the HIV-1 pro Gene Population. We measured LD for the sequences in the T1 and T2 populations. We identified very few examples of LD at these two time points using the Fisher's exact test with a Bonferroni correction. Of the 103 polymorphic sites in T1, only three pairs were in significant LD. Similarly, in T2 with 118 polymorphic sites, only and before ritonavir (37) drug selection (FIG. 4). The combined sequence population from the two time points (T1 and T2) before therapy consisted of 492 unique pro gene sequences with 155 SNPs. About 4% (e.g., 21) of these unique gene sequences were above 0.5% abundance, and these 21 unique gene sequences represented 67% of all sampled genomes, with the genome representing the overall consensus sequence comprising 21% of the total population (FIGS. 8A and 8B). The relatively small number of unique gene sequences above 0.5% frequency in the population contained only 7% of the 155 detected SNPs. Thus, a large proportion of the viral population's diversity was associated with a large number of pro gene sequences that were present at low abundance (FIGS. 8A and 8C); conversely, the majority of the population consisted of a small number of SNPs. Similarly, Tajima's D statistic for T1 and T2 in this individual were −2.35 and −2.31, respectively (Table 2), indicative of a population structure that has an excess of low frequency polymorphisms. This pattern is consistent with but more extreme than that observed in a prior shallow intrahost survey in which a metapopulation model was proposed to explain the pattern of Tajima's D statistic. FIG. 2A-2B shows the encoded amino acid variability and synonymous nucleotide variability present in two or more individual genomes across the 99 codons in the pro gene for these samples.

Synonymous variability. There were 57 codons (with 63 variants/SNPs) that contained synonymous diversity that appeared in both pretherapy time points, and 30 codons (with 31 variants) that appeared in only one time point. Taken together, 75 of the 99 codons contained some level of synonymous diversity (FIG. 2A-2B and Table 1). Of the 63 variants that were present in both untreated time points, 92% were transitions. Of the 31 variants that appeared in only one of the time points, 71% were transitions, representing a significantly smaller fraction of transitions than among the synonymous variants that appeared at both time points (P=0.012; Fisher's exact test). This suggests that synonymous transversions are selected against over time.

Nonsynonymous variability. There were 26 codons (28 variants) that contained coding variability that appeared in both pretherapy time points, and an additional 28 codons (33 variants) with nonsynonymous changes found in only one of the time points. Taken together, 49 of the 99 codons contained some level of nonsynonymous diversity (FIG. 2A-2B and Table 1). For the 28 nonsynonymous variants detected at both time points, 22 were transitions, and these mostly represented conservative amino acid changes. In the case of synonymous mutations two-thirds of the variants were present at both time points, whereas in the case of nonsynonymous mutations, less than half were present at both time points (P=0.012; Fisher's exact test). This observation suggests that, at this level of sequence sampling, we are able to see a difference in stability within the population in comparing synonymous and nonsynonymous substitutions.

Genetic fluctuation. We compared the stability of minor SNPs present at both T1 and T2. A total of 14 of the 91 SNPs (synonymous and nonsynonymous that appeared at both time points) had significant changes in abundance between the two time points ($\chi^2$ test with a false discovery rate of 0.05). Of the 14 SNPs with significant changes in abundance, 11 had a decrease in the abundance, with an average decrease around 7.5-fold. There were three SNPs that had a significant increase in abundance, all of which were synonymous, ranging from a 4- to 47-fold increase. Although a majority of SNPs that changed in abundance had a decrease in the frequency between T1 and T2, on a population level, there was not a large change in diversity between the two time points (T1 $\pi$=0.0080, T2 $\pi$=0.0079; Table 2). However, the trend of increased abundance at the three sites may be driven by selection of cryptic epitopes in an alternative reading frame.

Significance of rare variants. We observed two extremes in terms of biological relevance in the untreated population among variants detected as at least two independent sequences across the three time points. At one extreme was the detection of nonviable genomes in the form of a coding variant at position 25, which mutates the active site of the protease, and the detection of termination codons at positions 42 and 61 (Table 1). At the other extreme was the detection of the L90M and V82A variants (at time points 1 and 2, respectively) that became the major resistance populations after ritonavir therapy was initiated (see below, FIG. 3); in addition, V82I and V82L were detected at T2. We found two more examples of primary resistance mutations at low abundance, K20R at all three time points and M46I at two time points, but these did not grow out in the presence of ritonavir (FIG. 3 and Table 1). Similarly, fitness compensatory mutations were also detected at low abundance (L10F, M36I, L63P, A71T, and V77I), all below 1%, and only L63P increased (modestly) in abundance after exposure to ritonavir. More generally, of the 28 substitutions most closely associated with protease inhibitor drug resistance, we found 10 such variants, half of which were detected at both pretherapy time points (Table 1).

Assessment of Linkage Disequilibrium (LD) Within the HIV-1 pro Gene Population. We measured LD for the sequences in the T1 and T2 populations. We identified very few examples of LD at these two time points using the Fisher's exact test with a Bonferroni correction. Of the 103 polymorphic sites in T1, only three pairs were in significant LD. Similarly, in T2 with 118 polymorphic sites, only the number of pathogen genomes in the sample is limited, and the use of PCR can obscure the quality of the sampling by creating a large amount of DNA from a relatively small number of starting templates. This can create artificial homogeneity, inflate estimates of segregating genetic variation, skew the distribution of alleles in the population, and introduce artificial diversity.

Figure 10:
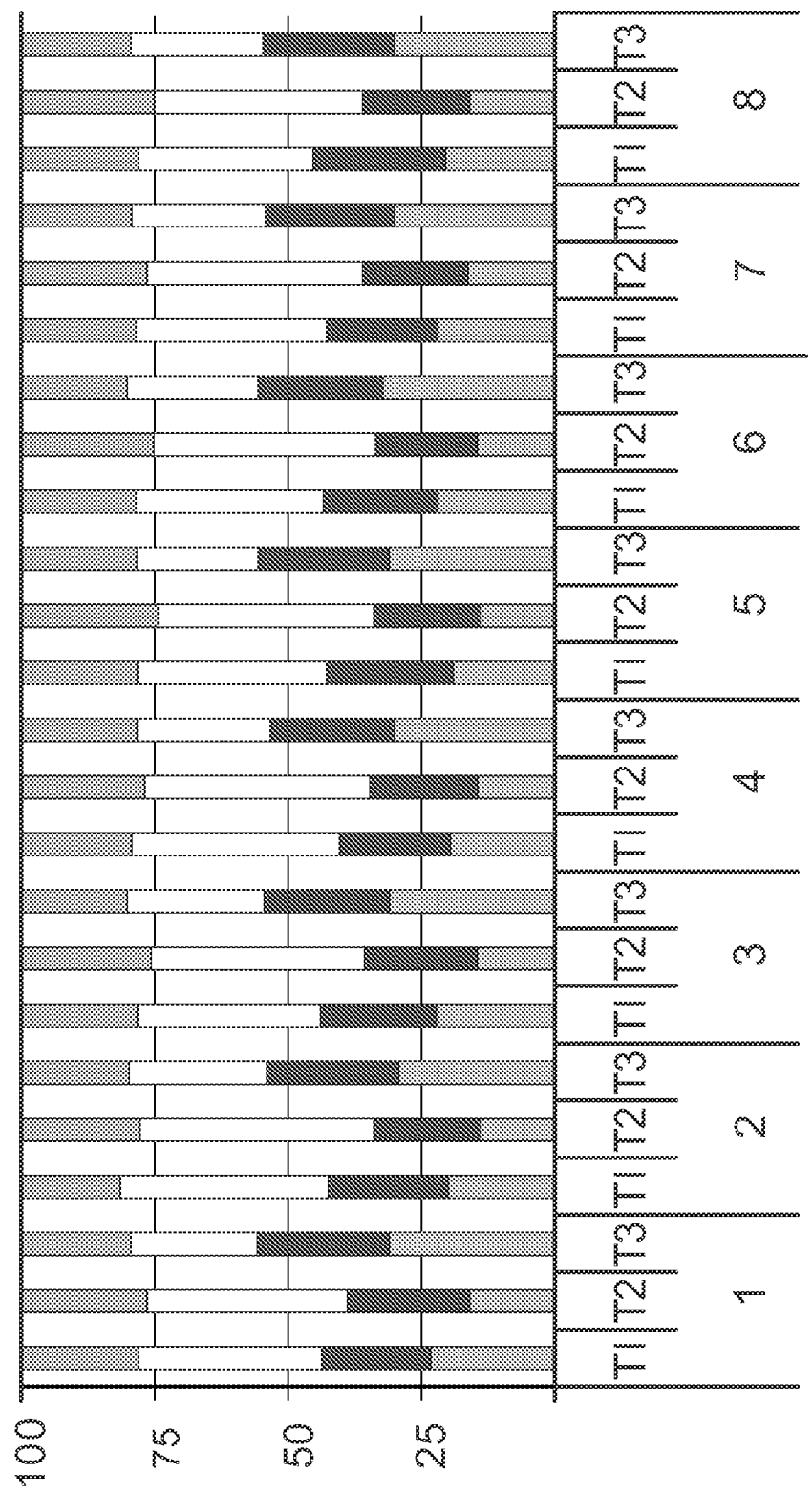
FIG. 10 shows the frequency of appearance of individual nucleotides at each Primer ID position (labeled 1-8) in resolved consensus sequences. Shading represents Da (dark gray), dT (black), dC (white), and dG (light gray), respectively. On the horizontal axis, each Primer ID position is subdivided by time point (T1, T2, and T3).
Figure 11:
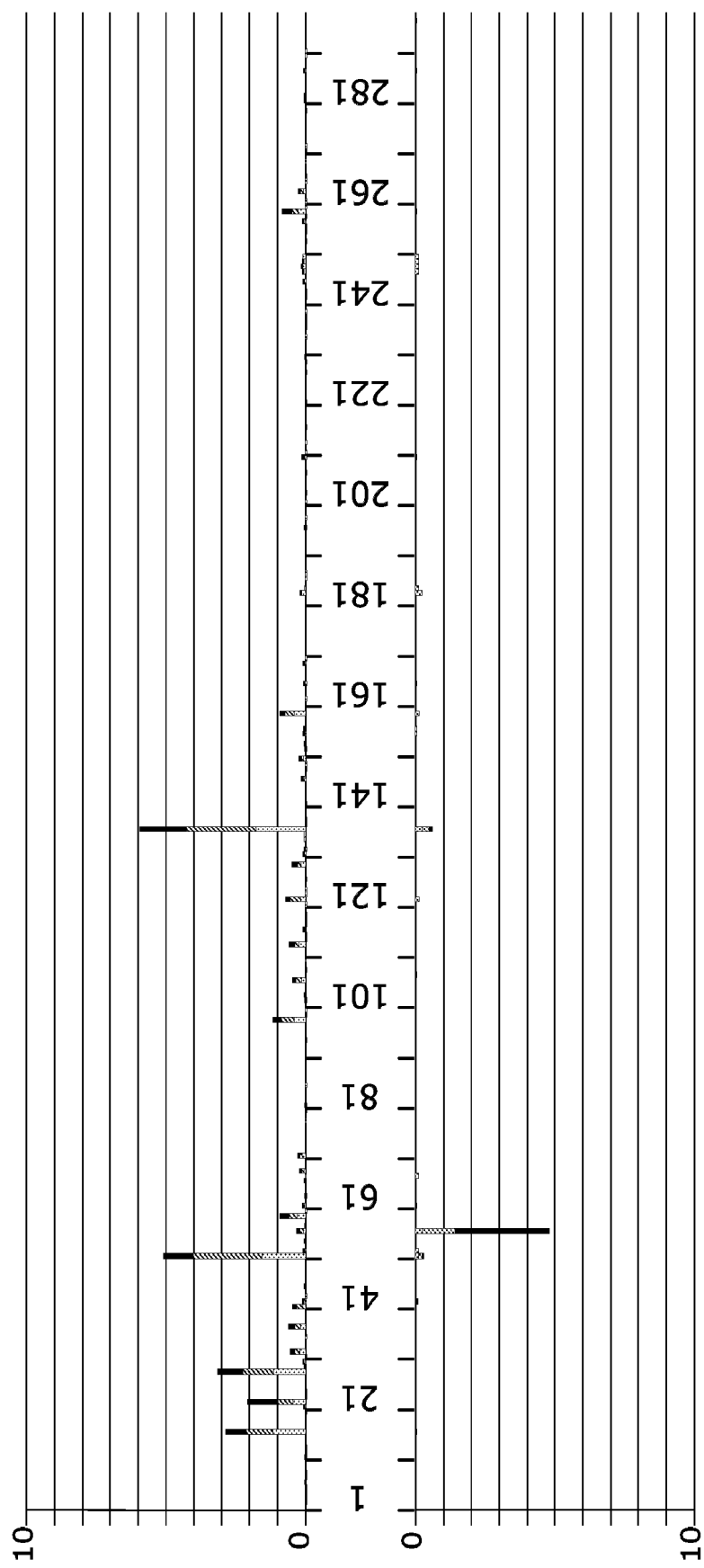
FIG. 11 shows the frequency of deletions in total versus consensus sequences. The percentage and nucleotide position of single nucleotide deletions are depicted in total (upward facing bars) or consensus (downward facing bars) sequences. Shade corresponds to time point for T1, T2, and T3.

We have developed a strategy that allows each sampled template to be tagged with a unique ID by a primer that has a degenerate sequence tag incorporated during the primer oligonucleotide synthesis (FIG. 10). This tag can then be followed through the PCR and the deep sequencing protocol to identify sequencing over-coverage (resampling) of the individual viral templates. Because the Primer ID allows for the identification of over-coverage, this can then be used to create a consensus sequence for each template, avoiding both PCR-related errors and sequencing errors (FIG. 11). In addition, the number of different Primer IDs reflects the number of templates that were actually sampled. This allows a realistic assessment of the depth of population sampling and makes it possible to apply a more rigorous analysis of minor variants by correcting the allelic skewing during the PCR.

We tested the Primer ID approach by sequencing the HIV-1 protease coding domain at three time points in a subject who was intermittently exposed to a protease inhibitor between the second and third time points. A key feature of our approach is the removal of fortuitous errors and accounting for resampling, which results in a dramatic reshaping of the original data set of 72,162 reads. Other approaches that rely on statistical modeling have been developed to deal with the problem of high sequencing error rates associated with deep sequencing technologies. The use of the Primer ID to create consensus sequences resulted in the removal of 80% of the unique sequence polymorphisms (defined as a change in the consensus without regard to frequency of appearance) in the data set. Similarly, allelic skewing was dramatic among the sampled sequences, in most cases ranging from 2- to 15-fold but going up to nearly 100-fold. Although the Primer ID reveals such skewing and helps correct it, this is clearly a poorly controlled feature of PCR amplifications that can dramatically affect the observed abundance of complex populations, especially the minor variants. Allelic skewing may still persist if the cDNA primer or the upstream PCR primer binds differentially among the templates, or if cDNAs enter the PCR amplification in later rounds and are discarded because they do not result in at least three reads to allow a consensus sequence to be formed. Also, residual misincorporation errors by RT and in the first round of PCR synthesis still limit the interpretation of mutations that occur in the range of 0.01-0.1%. This problem is not overcome with larger numbers of sequences. Given the low diversity in these samples, we removed all substitutions that appeared once because their number approximated the expected number of residual sequence errors, and this resulted in a sensitivity of detection in the range of 0.1% for SNPs that appeared above the frequency of the residual sequence error rate.

Using the Primer ID approach, we were able to describe a number of features of the protease sequence population. First, a pooled analysis of two time points six months apart showed that the variants present at greater than 0.5% in abundance made up two-thirds of the total population but represented only 4% of unique genome sequences and contained only 7% of the total unique sequence polymorphisms. About 60% of the diversity was stable over both time points, with synonymous SNPs maintained at a significantly higher proportion in the two time points than nonsynonymous SNPs. Only 18% of the total diversity represented nonsynonymous SNPs that were present at both time points. However, our ability to assess persistence of these sequences is limited by the depth of sampling, although we feel we are approaching the practical limit of sampling with this technology. We observed nonviable substitutions and estimate that most of the SNPs that appeared once were the result of remaining method error. We found no pattern of conserved linkage among these SNPs, consistent with high levels of recombination across the population.

Although the overall measurement of diversity ($\pi$) was similar between the first two time points, we noted that the biggest changes in SNP abundance between the two time points were in three synonymous codon positions (L24L, K70K, and G73G). These dynamic increases made these SNPs part of a larger group of SNPs that accounted for 51% of the total sequences that were otherwise identical to the consensus sequence (Q18Q, L19I, L24L, K70K, G73G, and Q18Q/L19I/L24L'). These SNPs also overlapped the major SNPs that defined subgroups of the resistant variants (L19I; L19V; G16G/L19V). We considered the possibility that there was a unifying feature of these SNPs. We found such a feature in that all of these SNPs, both coding and non-coding, result in changes in two relatively large alternative ORFs that lie at the 5' and 3' ends of the pro gene. Alternative reading frames have been suggested to generate cryptic CTL epitopes. In this scenario, these abundant SNPs would represent various escape mutants. Such selective pressures could explain the dynamic behavior of several of these SNPs between the first two time points.

After intermittent exposure to the protease inhibitor ritonavir, we were able to identify six independent lineages of drug resistance mutations. With the intermittent exposure in this particular subject, it was possible to see the major V82A lineage most often seen with ritonavir resistance, but also significant populations of 184V and L90M. We also saw minor populations of V82I, V82L, and V82F. This mixed population of resistant lineages likely represents the early stages of the evolution of resistance, a conclusion supported by the minor appearance of the L63P compensatory mutation and the complete absence of I54V, which is an often seen compensatory mutation for V82A. We saw few examples of genomes with multiple resistance mutations, although these would be expected after more extensive selection. We and others have previously examined viral sequences that have been collected in large databases. Typically, these sequences represent the single predominant sequence within an individual, and the use of these sequences allows for assessment of interperson diversity. In the future, it will be an interesting exercise to compare the conclusions reached by examining viral diversity within a person to viral diversity between people; however more intraperson diversity needs to be measured at this level of detail to allow comparison of inter-versus intraperson diversity.

The presence of preexisting drug-resistant variants and their role in therapy failure is of great interest, and accurate, deep sampling of a viral population can add significantly to our understanding of this question. We were able to detect several examples of drug-resistance mutations but only at a very low level. Our ability to reliably detect these mutations is limited to those that appear at a frequency of 0.1-0.2%, limited in part by the low overall diversity in the population. We were able to see examples of mutations that are typically seen only in the presence of drug selection. However, the detection was usually as one genome at two time points or two genomes at one time point. This was also the level of detection of active site mutations in the protease and of termination codons, which must represent either transient viral genomes or residual misincorporation errors. In two cases, we were able to observe the resistance mutation (V82A and L90M) at pretherapy time points linked to the same polymorphisms that were present on the variant that grew out during drug exposure. Thus, although it is likely that we are detecting relevant preexisting drug-resistant variants, these are at the limit of detection and, if they are maintained at a steady-state level, it is well under 0.5% abundance.

Most protocols of high throughput sequencing technologies still require an initial quantity of DNA that necessitates an upfront PCR step for many applications. The use of a Primer ID will help clarify the sequencing products in any strategy that uses an initial PCR step with its attendant error rate, recombination, and resampling. In an independent effort Kinde et al. have described an analogous approach in another deep sequencing of individual templates before PCR and subsequent sequence analysis will be essential for understanding the true complexity and diversity of genetically dynamic populations.

Materials and Methods

Viral RNA was isolated from blood plasma using the QIAmp Viral RNA kit (Qiagen). cDNA was generated using SuperScript III Reverse Transcriptase (Invitrogen) using the primer (with Primer ID) as described. Following the reaction, RNA in hybrid was removed by RNaseH treatment (Invitrogen). Unincorporated cDNA primer was removed, and the cDNA product amplified by PCR. Sequencing was done using the 454 platform (Roche).

vRNA Extraction and cDNA Synthesis. Viral RNA was extracted from three plasma samples taken longitudinally from an individual infected with subtype B HIV-1 who was participating in a protease inhibitor efficacy trial (M94-247). Two samples were collected at ~6 mo before and immediately before the addition of the protease inhibitor ritonavir to a failed therapy regimen (plasma viral loads of 285,360 copies of viral RNA/mL and 321,100 copies of viral RNA/mL, respectively), and one sample was collected during ritonavir therapy (at approximately 2 months on therapy, 349,920 copies of viral RNA/mL) but during a time of apparent intermittent compliance. For each plasma sample, vRNA was extracted from pelleted (25,000×g for 2 h) viral particles using the QiaAMP Viral RNA kit (Qiagen). Approximately 10,000 copies of viral RNA from each sample were present in the cDNA synthesis reaction as described. The tagging primer used was, 5'-GCCTTGCCAGCACGCTCAGGCCTTGCA(BARCODE)CGNNNNNNNNTCCTGGCTTTAA TTTTACTGGTACAGT-3'. (SEQ ID NO. 2) The barcode represented TCA, GTA, and TAT for study days 58, 248, and 303, respectively. The 3' end of the tagging primer targeted downstream of the protease coding domain (HXB2 2568-2594). The oligonucleotides were purchased from IDT and were purified by standard desalting.

Amplification of Tagged Sequences. The single-stranded cDNA was column purified using the PureLink PCR Purification Kit (Invitrogen), using Binding Buffer HC (high cutoff) and three washes to remove the cDNA primer. Primer removal was verified by electropherogram analysis using an Experion HighSense RNA microfluidic chip (Bio-Rad Laboratories). Samples were amplified by nested PCR, using upstream primers 5'-GAGAGACAGGCTAATTTTTTAGG-3' (HXB2 2071-2093) (SEQ ID NO. 3) and 5'-ATAGACAAGGAACTGTATCC-3' (HXB2 2224-2243) (SEQ ID NO. 4); the downstream primers targeted the 5' portion of the cDNA tagging primer 5-GCCTTGCCAGCACGCTCAGGC-3' (SEQ ID NO. 5) then 5'-CCAGCACGCTCAGGCCTTGCA-3'(SEQ ID NO. 6). The PCR was done using Platinum Taq DNA Polymerase High Fidelity (Invitrogen). Each reaction contained 1× High Fidelity PCR Buffer, 0.2 mM of each dNTP, 2 mM MgCl2, 0.2 µM of each primer, 1.5 units of Platinum Taq DNA Polymerase. The purified cDNA template was split to 2×50 µl for the first round PCR, and 1 µl of the purified first round product was used for nested PCR. Samples were denatured at 94° C. for 2 min, followed by 30 cycles of 94° C. for 15 s, 55° C. for 30 s, 68° C. for 1 min, and a final extension at 68° C. for 5 min.

Samples were column purified after the first round of PCR using the MinElute PCR Purification Kit (Qiagen), and eluted into 30 µl of buffer EB. Second round PCR product was gel purified using a 2% agarose gel and QIAquick gel extraction kit (Qiagen), with incubation of the solubilization buffer at room temperature. DNA was quantified by Qubit fluorometer using dsDNA High Sense assay (Invitrogen).

Product generation, quality, and primer removal for both PCR rounds was verified using an Experion DNA microfluidic chip (Bio-Rad).

454 Pyrosequencing. Tagged samples from the three time points were combined and sequenced on the 454 GS FLX platform with XLR70 Titanium sequencing chemistry as per the manufacturer's instructions (Roche) but with underloaded beads to minimize signal crosstalk. Sequences were processed from two independent 454 GS FLX Titanium runs (⅛th of a plate each).

Bioinformatic Pipeline for Raw Sequence Processing. A suite of programs was written to filter and parse raw 454 sequencing reads. In short, first, each sequence was placed in the correct orientation compared with a reference pro gene sequence. This alignment was then used to identify insertions or deletions caused by the 454 sequencing of homopolymers. When there was an insertion, the extraneous base was excised from the sequence. Deletions retained were largely resolved in the construction of the consensus sequence. Second, they were evaluated for the presence of the cDNA primer 5' tail, with the encoded information (barcode and Primer ID) exactly spaced. Third, individual sequences were binned by their barcodes, and then by their Primer ID. Fourth, sequences were trimmed to the protease coding domain (pro gene). Within a barcode bin, when three sequences contained an identical Primer ID, a consensus sequence was called by majority rule. Ambiguous nucleotide designations were used when there was a tie (FIG. 6B). Sequences are available under GenBank accession numbers JN820319-JN824997.

Population Analyses. A $\chi 2$ test was used to test for significance changes in allele frequency between the two untreated time points. To control for multiple testing, collective assessment of significance was based on False Discovery Rate analysis (FDR=0.05). Tests for linkage disequilibrium were computed by DnaSP v.5.10.01 (4). These tests were done on filtered populations devoid of sequences containing ambiguities or gaps. Tests for neutrality were computed by DnaSP and R (5) on filtered populations devoid of sequences containing ambiguities. Gaps and alleles represented by a single sequence were reverted to the consensus. Beta P values were calculated against the null hypothesis that D=0, assuming that D follows a beta distribution after rescaling on [0, 1].

Diversity across and within populations was computed through customized bioinformatics suites. Unfiltered sequences were used in the analysis, and ambiguities, gaps, and alleles represented by a single sequence were removed from the final tabulation (FIG. 2A-2B and Table 1).

SNPs were graphically displayed through the Highlighter tool (www.hiv.lanl.gov).

Phylogenetic Resolution of Sequences. The phylogeny for the population of consensus sequences from all three time points was resolved using two alternative methods and on populations devoid of sequences containing gaps or ambiguities. When only one example of a SNP was present across all sequences, it was converted to the consensus on the assumption that it was likely generated by residual method error. First, the Neighbor-Joining tree using the Kimura translation for pairwise distance and a bootstrap of 100 iterations was constructed with QuickTree v.1.1.

Second, Maximum likelihood phylogeny was inferred using the PHYLIP package, version 3.69, and the calculated phylogeny is available upon request. The PHYLIP program seqboot was used to create 100 bootstraps. Resulting bootstraps were submitted to the PHYLIP program dnamlk for maximum likelihood inference subject to a strict molecular clock. The consensus tree of all boostrap results was constructed using the PHYLIP program consense.

Both phylogenetic trees were visualized by a customized modification of Figtree v.1.3.1.

Additional Considerations. Degenerate base synthesis in the cDNA primer. The degenerate bases (Primer ID) in the cDNA synthesis primer were randomized using machine mixing during oligonucleotide synthesis. All four DNA phosphoramidite monomer bases are introduced to the column at the same time, but due to slight differences in binding or delivery, a strict equimolar ratio of dA, dT, dC, and dG may not be realized, resulting in a Primer ID bias (FIG. 10). When there is a Primer ID bias, there is an increased probability that a particular Primer ID will tag multiple templates because sequence tags with over-represented nucleotides will be more abundant than sequence tags with under-represented nucleotides. Because the bias is amplified over the length of the Primer ID the skewing can be significant. We observed a bias of ~40% dC in one of our Primer ID syntheses, and at the extreme $dC_8$ would be present at a 40-fold excess over the sequence frequency expected if all nucleotides were present at equal concentration. Similarly, we observed 15% dA in one synthesis which would result in a 60-fold decrease in the expected frequency of $dA_8$. This appears to be the result in variation in primer synthesis because the bias varied in the different barcode bins and therefore was not a constant feature of the cDNA synthesis step. However, this phenomenon is somewhat mitigated when a consensus sequence is formed, as whatever template was resampled to the greater extent within a mixed Primer ID population would be recorded.

Frameshift mutations. Pyrosequencing commonly miscalls homopolymers, resulting in a frameshift mutation by either calling too few or too many nucleotides in the homopolymer run. The HIV-1 pro gene contains several homopolymeric stretches. We took advantage of a known length (conserved in a coding region) to align individual reads against a reference sequence. Given this bias we removed the insertions to retain the correct length of the homopolymer run. Deletions were retained. Through consensus sequence generation, the deleted base was often recovered when the other resampled reads contained the missing base. Although consensus sequence generation reduced the spread and frequency of deletions in the final resolved, consensus reads, it did not eliminate deletions altogether (FIG. 11).

Example 2

Accurate Sampling and Deep Sequencing HIV-1 Protease Using a Primer ID

Viruses can create complex genetic populations within a host, and Deep sequencing technologies offer the opportunity to extensively sample these populations. However, features of these techniques limit their application, particularly when a polymerase chain reaction (PCR) step precedes the sequencing protocol.

Typically, an unknown number of templates are utilized in initiating the PCR amplification and this can lead to unrecognized sequence resampling. PCR-mediated recombination can create artifactual linkage and disrupt real linkage. Finally, misincorporation during PCR and errors during the sequencing protocol can create artificial diversity.

We have solved this by including a random sequence tag in the initial primer such that each template receives a Primer ID. After sequencing, repetitive identification of the Primer ID reveals sequence resampling, which can then be used to create an accurate consensus sequence for each template. The resulting population of consensus sequences directly identify the initial sampled templates. The use of Primer IDs can directly correct for unrecognized sequence resampling, PCR-mediated recombination, differential template amplification, polymerase nucleotide misincorporation, and sequencing error.

We applied this approach to the HIV-1 protease (pro) gene to view the distribution of sequence variation within a complex population. We identified major and minor polymorphisms within coding and noncoding positions. In addition, we observed dynamic changes across the population during intermittent drug exposure, including the emergence of resistant alleles.

Figure 12A:
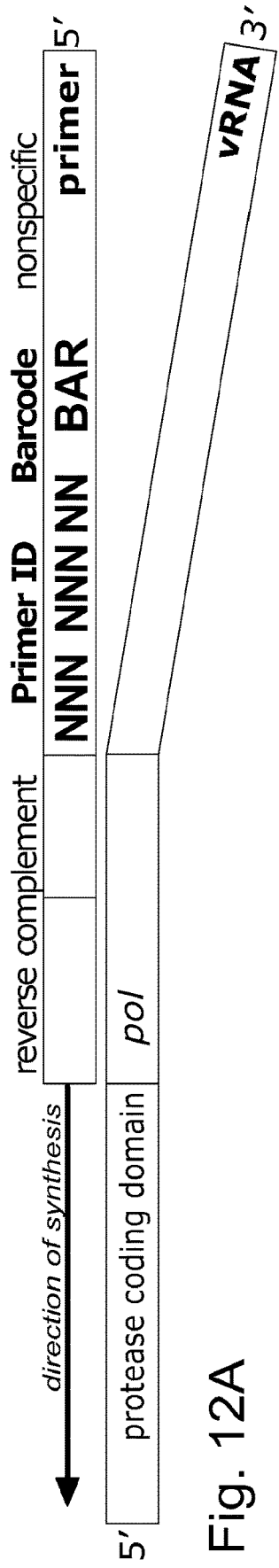
FIG. 12A shows a schematic of a tagging primer. Degenerate sequence tags individual vRNA templates with a unique ID. An a priori selected barcode serves as a sample ID. Together, individual samples and templates can be traced post-PCR amplification and sequencing.

Methods:

A population of cDNA synthesis primers were designed to contain a string of eight degenerate nucleotides (65,536 distinct sequence combinations, or Primer IDs), and an a priori selected three nucleotide barcode (FIG. 12A). After cDNA synthesis, the nonspecific 5' end of the primer was used for enrichment of tagged sequences by nested PCR.

Figure 12B:
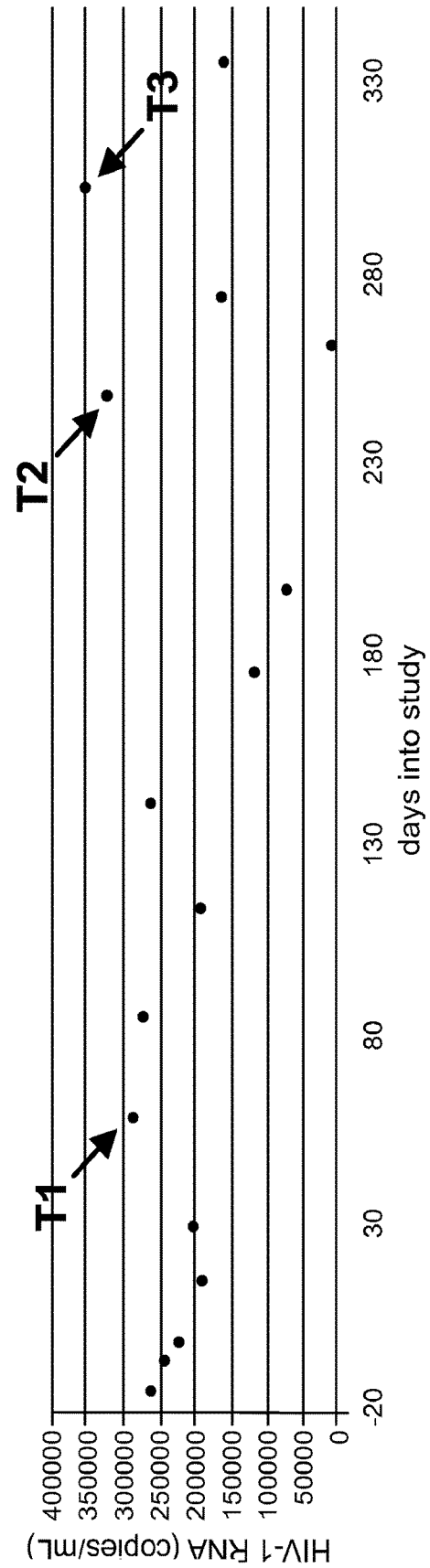
FIG. 12B shows patient sampling and clinical history. HIV-1 RNA was extracted from blood plasma of a single infected individual. Protease from two pre-Ritonavir therapy and one post-intermittent Ritonavir therapy was tagged and sequenced.

HIV-1 RNA was extracted from blood plasma. Protease from two pre-Ritonaivr therapy and 1 post-intermittent Ritonavir therapy was tagged and sequenced (FIG. 12B). Approximately 10,000 copies of HIV-1 viral RNA were tagged downstream of proteases, amplified, and sequenced on the 454 GS FLX Titanium. FIG. 13B displays a summary of the resolved sequences.

Figures 2, 13A:
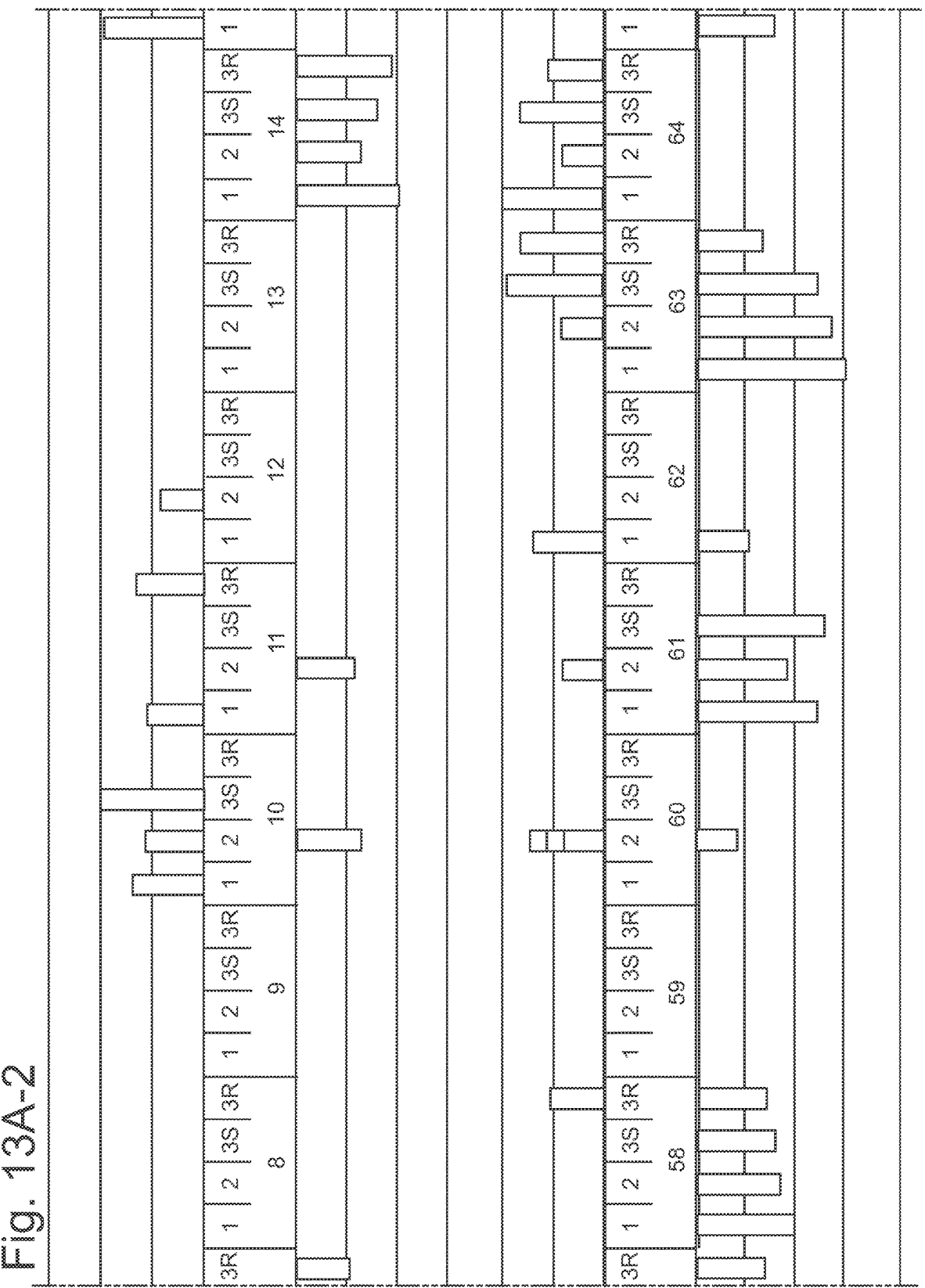
FIG. 13A shows the allele frequencies per amino acid position. Upward facing bars are coding changes, downward facing bars are silent changes. Change in color within an amino acid position correlates to change in codon. 1=T1, 2=T2, 3S=T3V82, T3R=T3V92A.
Figures 3, 13A:
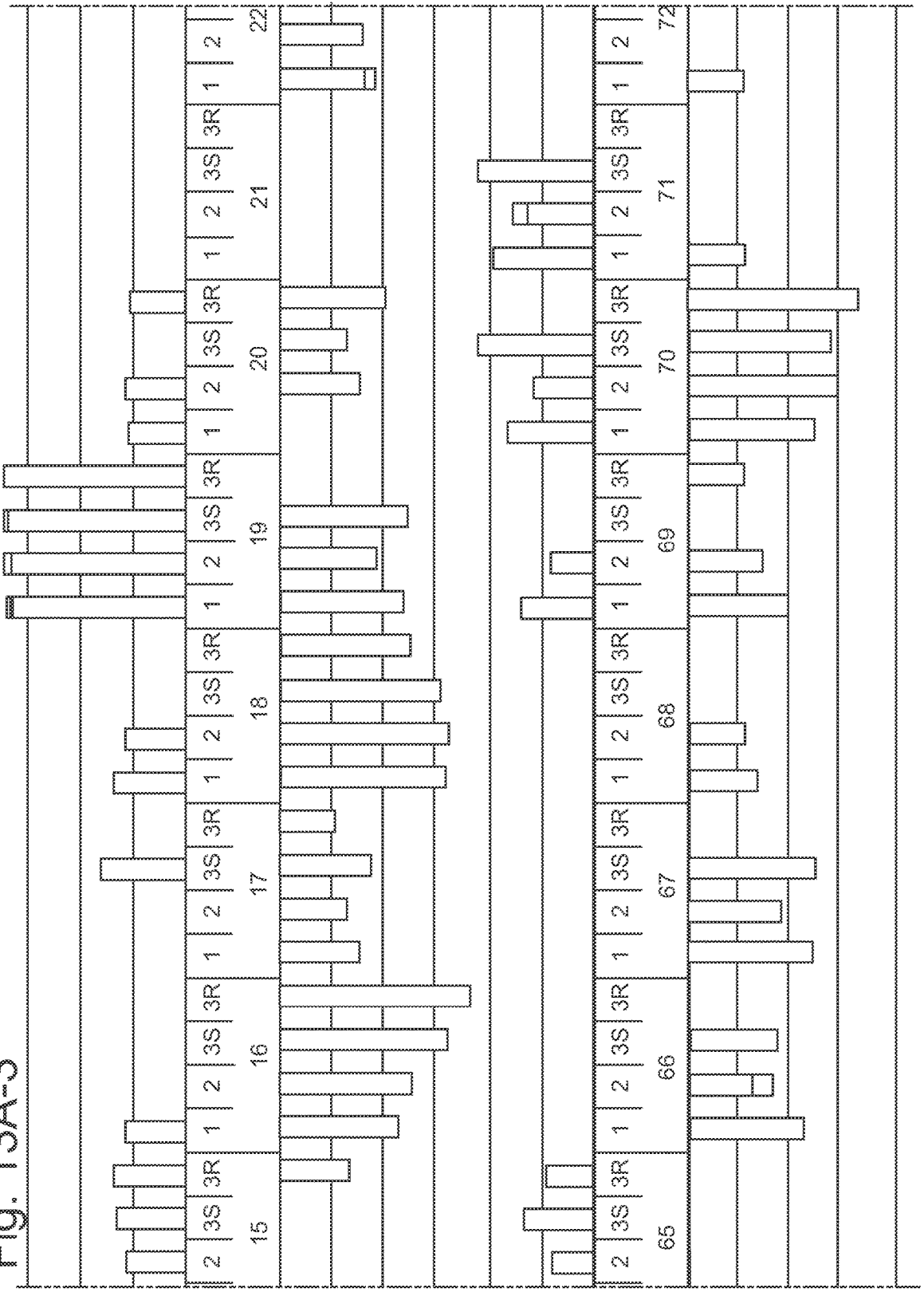
Figures 4, 13A:
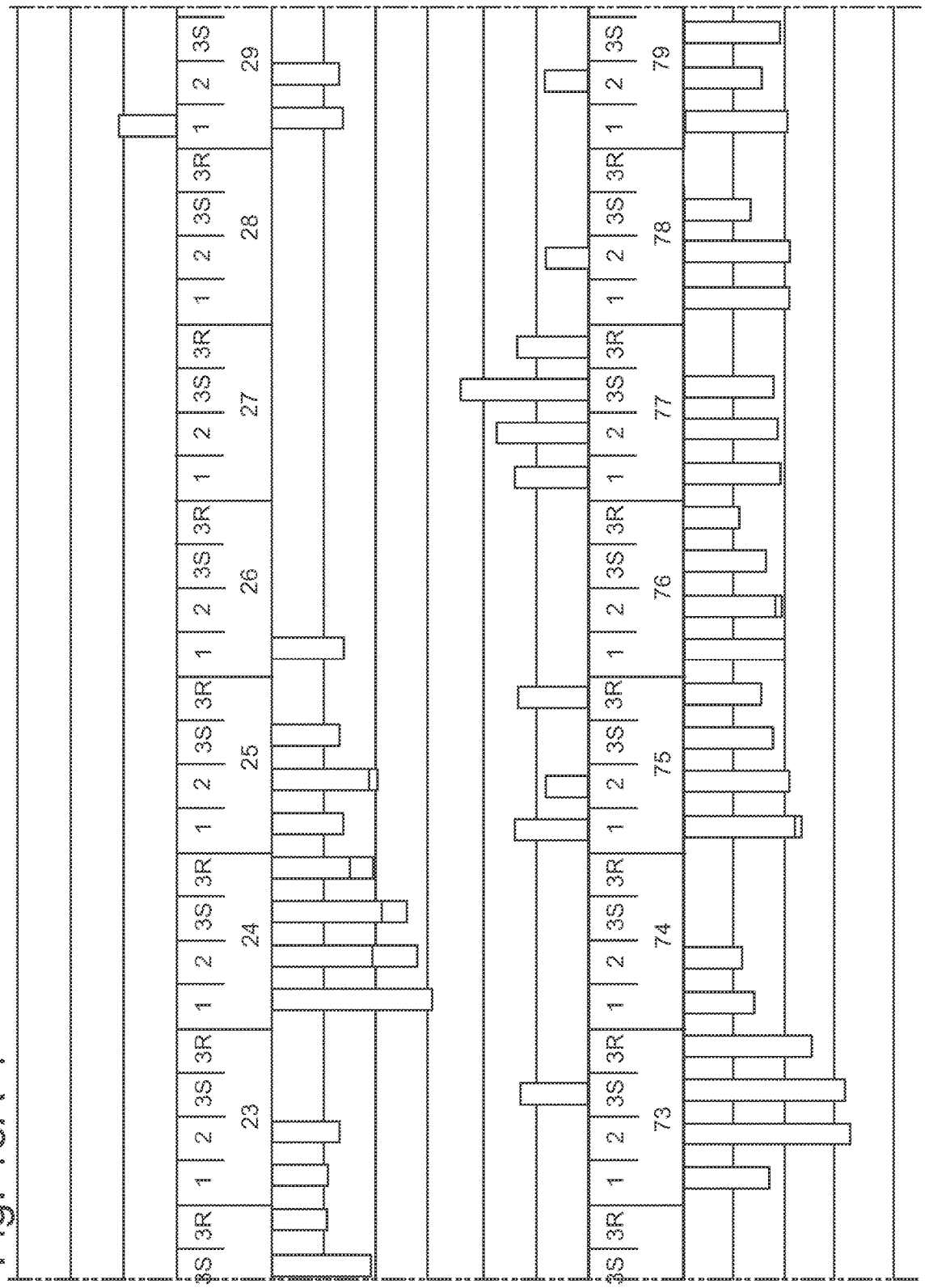
Figures 5, 13A:
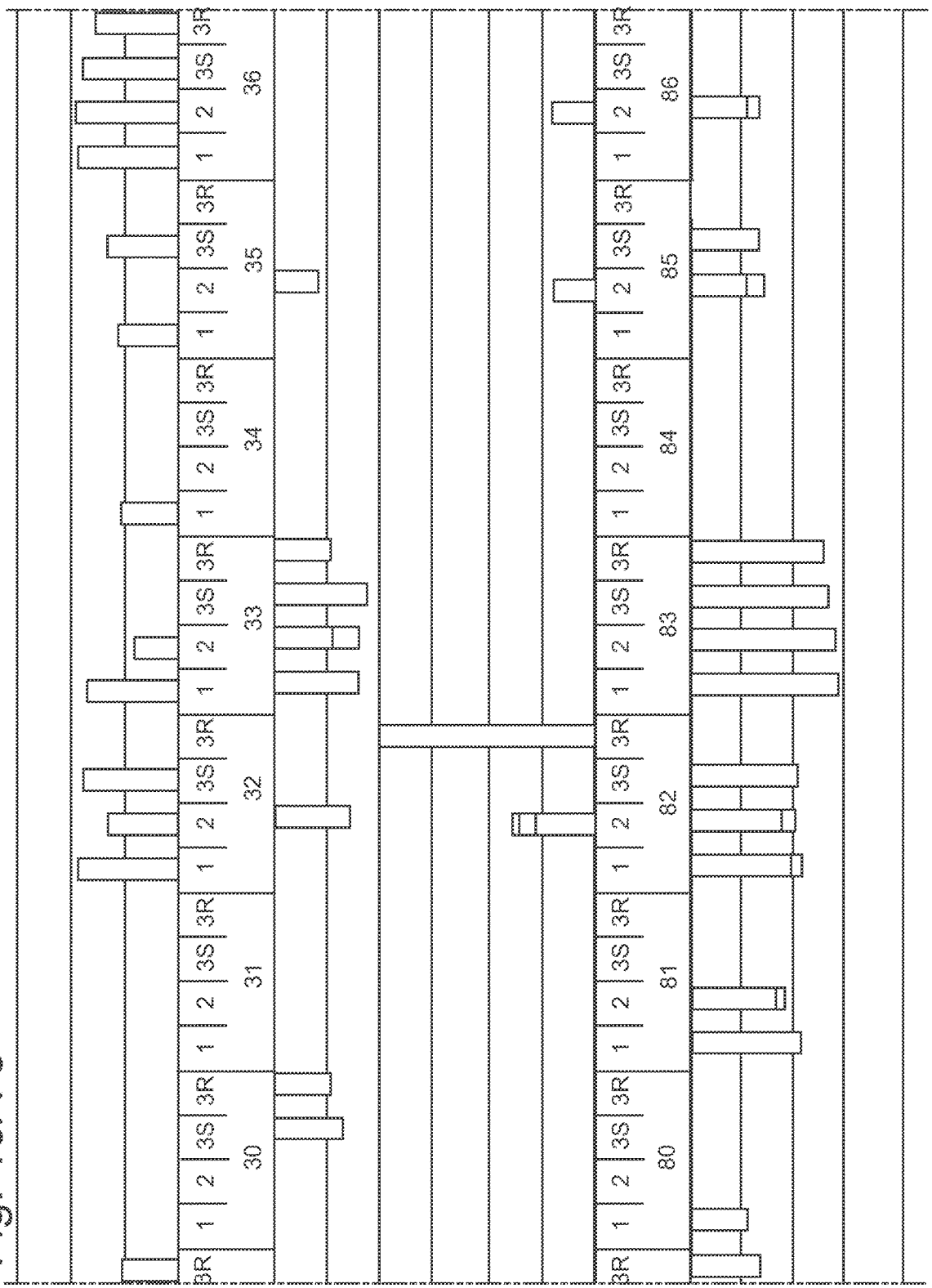
Figures 6, 13A:
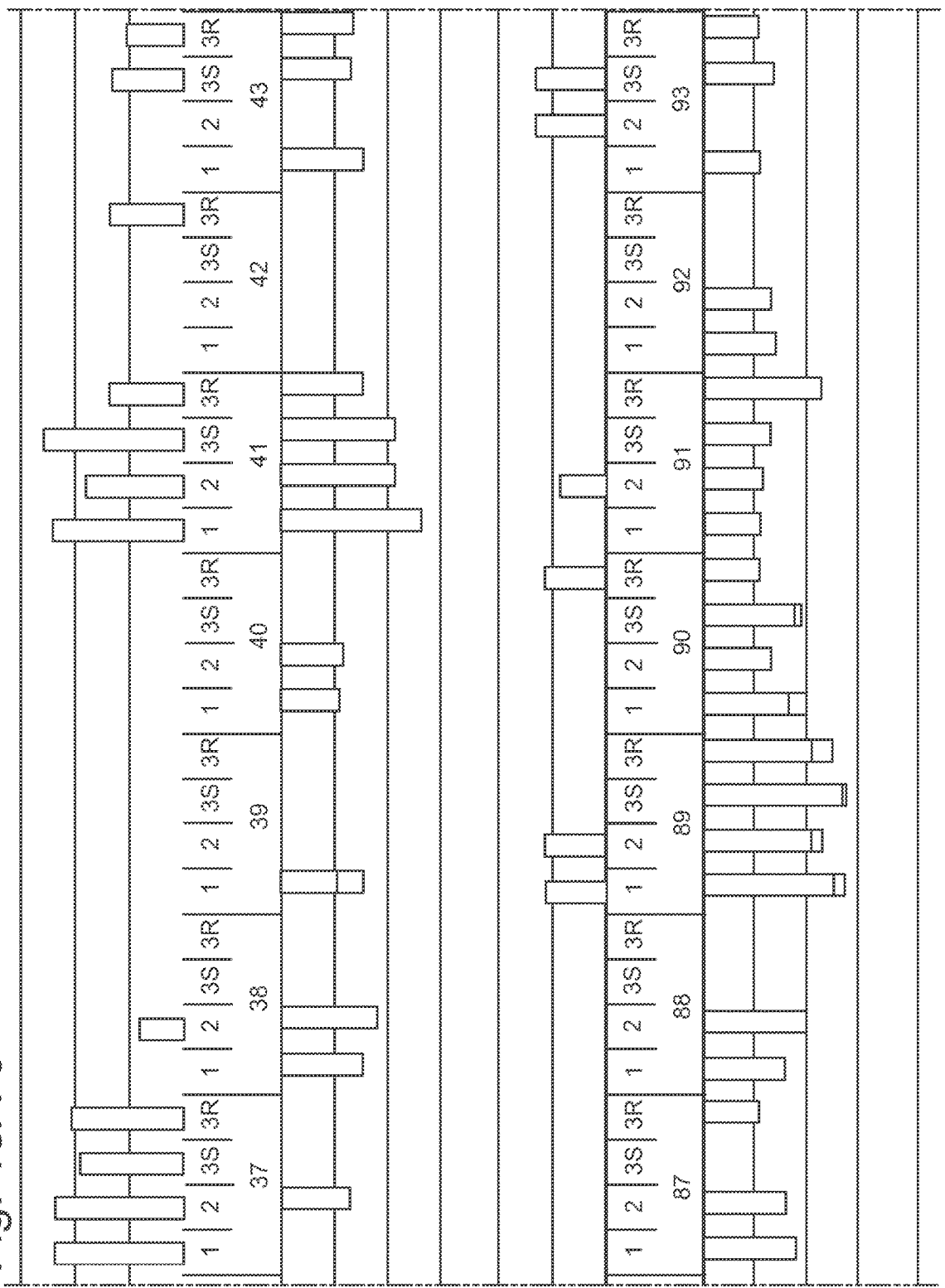
Figures 7, 13A:
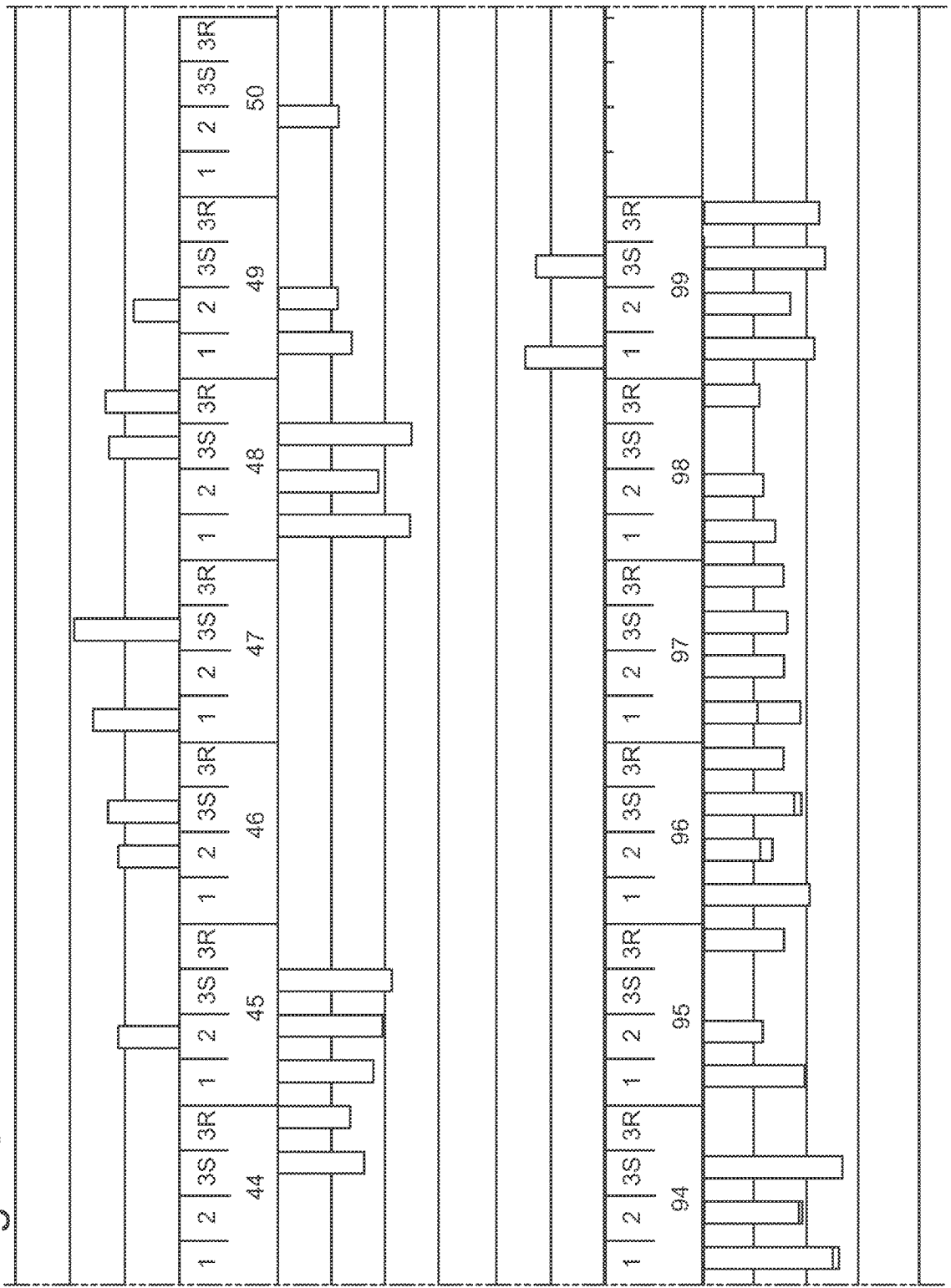
Figure 14:
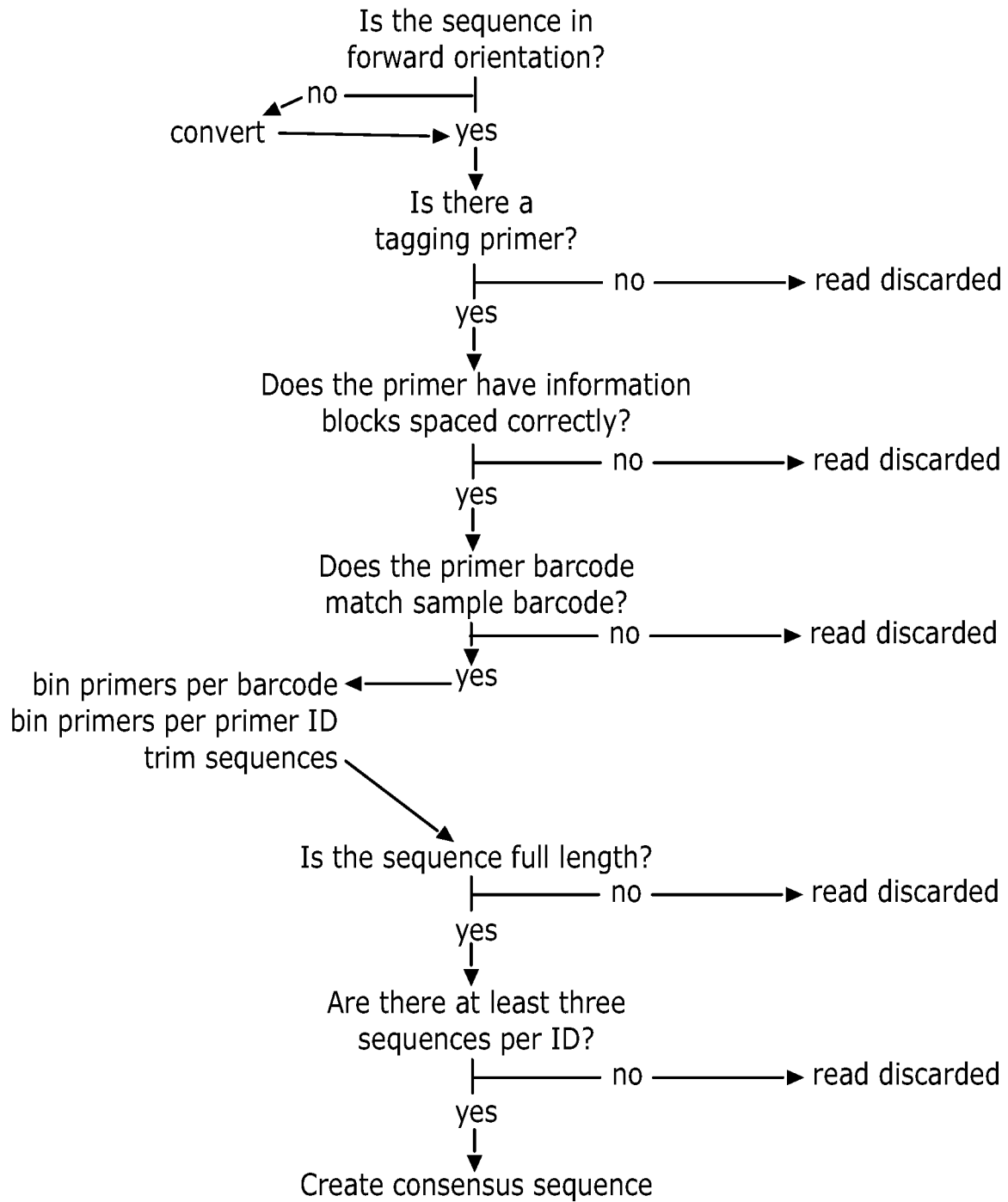
FIG. 14 shows a bioinformatic pipeline. Raw sequence reads were screened for uncorrupted tagging primers and full length protease. A minimum of three identical sample and Primer IDs were used to create individual consensus sequences.
Figure 15:
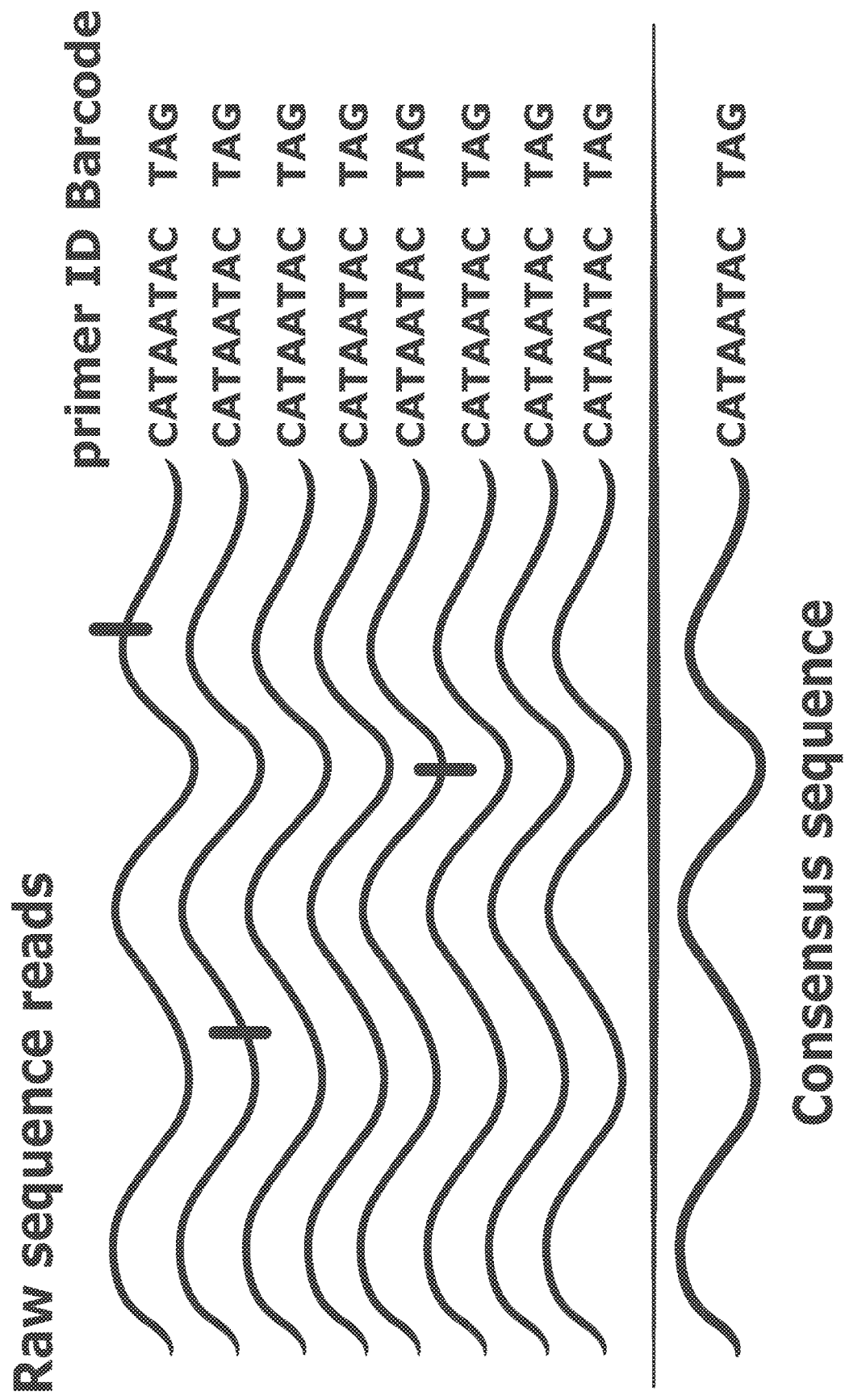
FIG. 15 shows consensus sequence generation. Polymerase misincorporation, artificial recombination, differential amplification, and sequencing errors introduce sequence diversity and skew allelic frequencies. Creating a consensus sequence directly corrects for this (SEQ ID No. 1).

A bioinformatics pipeline was developed to assess raw sequences for tagged, full-length protease (FIG. 14), and when three or more sequences contained an identical Primer ID, a consensus sequence was generated (FIG. 15). After direct error correction through filtering and processing of Primer IDs, the allelic frequency of the pro gene populations were assessed (FIG. 13A).

Discussion:

We have developed a strategy that allows each sampled template to be tagged with a sequence ID by a primer that has a degenerate sequence tag incorporated during synthesis. This tag can then be followed through the deep sequencing protocol to identify sequencing over-coverage of the individual templates. The over-coverage can be used to create a consensus sequence for each template, avoiding both PCR-related errors and sequencing errors. In addition, the number of different Primer IDs reflects the number templates that were actually sampled, allowing a realistic assessment of the quality of sampling which will make it possible to apply a more rigorous analysis of minor variants. In many settings, especially when working with pathogenic agents in clinical samples, the number of templates can be limiting and the use of PCR can obscure the limited quality of the sampling. This problem is solved by tagging each template as the first step then simply counting the number of templates that were actually used as part of the last step.

Figure 16:
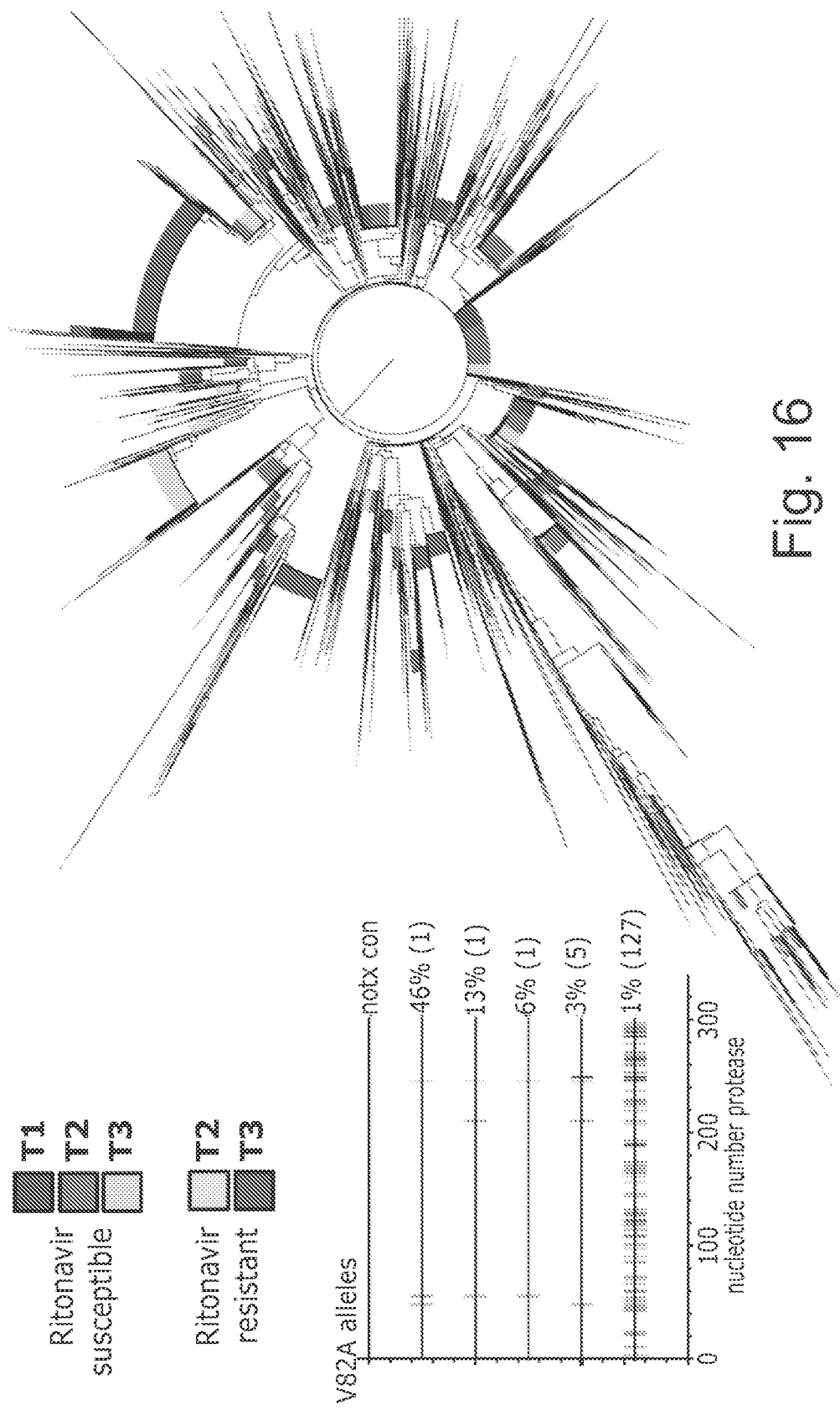
FIG. 16 shows phylogenetic tree and highlighter plot demonstrate emergence of V82A strain. A Neighbor-Joining tree was constructed from consensus sequences for all three time points. Clades were colored based on V82 (lighter gray) or V82A (darker gray) amino acid. The highlighter plot represents SNPs (defined from the T1 and T2 consensus sequence) in the V82A population. Denoted next to each sequence is frequency in the population and the number of sequences in the construct. A; gray, T; black, G; darker gray, C, lighter gray.

Accurately resolving viral templates comes at a cost of sequencing depth, as depth is a direct function of template number, but we have documented the nature and degree of allelic fluctuation throughout protease down to the 0.1% level of resolution. We showed synonymous and nonsynonymous fluctuation over time in an untreated environment, and when in an environment of intermittent selection from the protease inhibitor, Ritonavir. We detected the drug resistant allele, V82A, as a minor allele in the untreated population, and detected this exact variant comprising over a quarter of the rebounding population (FIG. 16). These results demonstrate the utility of applying this approach to the detection of minor variants in the context of HIV-1 treatment, and more generally to the question of minor variants in the context of a large genetically complex population.

TABLE 1

Frequency of nonconsensus codons per position

| AApos[a] | AAc[b] | Cc[c] | Cm[d] | Am[e] | T1[f] | T2[g] | T3[h] | T3s[i] | T3r[j] | Cm[k] | T1[l] | T2[m] | T3[n] | T3s[o] | T3r[p] |
|---|---|---|---|---|---|---|---|---|---|---|---|---|---|---|---|
| 4 | T | ACT | GCT | A |  | 0.06 | 0.05 |  | 0.09 |  |  |  |  |  |  |
| 5 | L | CTT | CCT | P | 0.12 |  | 0.05 | 0.14 |  |  |  |  |  |  |  |
| 7 | Q | CAA |  |  |  |  |  |  |  | CAG | 0.35 | 0.12 | 0.09 | 0.14 | 0.09 |
| 8 | R | CGA |  |  |  |  |  |  |  | CGG | 0.12 |  | 0.05 | 0.14 |  |
| 9 | P | CCC |  |  |  |  |  |  |  |  |  |  |  |  |  |
| 10 | L | CTC | TTC | F |  | 0.19 |  |  |  | CTT |  | 0.19 |  |  |  |
| 11 | V | GTC | ATC | I | 0.23 | 0.25 |  |  |  | GTT |  | 0.12 |  |  |  |
| 14 | K | AAG | AGG | R |  | 0.12 |  |  |  | AAA | 1.17 | 0.19 | 0.59 | 0.29 | 0.72 |
| 15 | I | ATA | GTA | V | 1.17 | 0.12 | 0.14 | 0.14 | 0.18 | ATC |  | 0.09 |  |  | 0.18 |
| 16 | G | GGG | AGG | R |  | 0.06 | 0.05 |  | 0.09 | GGA | 2.22 | 3.54 | 38.86 | 17.70 | 45.97 |
| 17 | G | GGG | AGG | R |  |  | 0.09 | 0.29 |  | GGA | 0.35 | 0.19 | 0.18 | 0.43 | 0.09 |
| 18 | Q | CAA | GAA | E | 0.23 | 0.12 |  |  |  | CAG | 18.55 | 21.75 | 6.46 | 12.81 | 3.53 |
| 19 | L | CTA | ACA | T | 0.47 |  |  |  |  |  |  |  |  |  |  |
|  |  |  | ATA | I | 19.25 | 19.83 | 20.42 | 19.28 | 24.98 | TTA | 0.12 | 0.19 | 0.09 | 0.29 |  |
|  |  |  | GTA | V | 3.38 | 5.66 | 46.00 | 25.61 | 52.76 |  |  |  |  |  |  |
| 20 | K | AAG | AGG | R | 0.12 | 0.12 | 0.05 |  | 0.09 | AAA |  | 0.31 | 0.86 | 0.29 | 1.27 |
| 21 | E | GAA |  |  |  |  |  |  |  | GAG | 0.12 | 0.06 | 0.05 | 0.14 |  |
| 22 | A | GCT |  |  |  |  |  |  |  | GCC | 0.47 | 0.44 | 0.27 | 0.58 | 0.18 |
|  |  |  |  |  |  |  |  |  |  | GCG | 0.23 |  |  |  |  |
| 23 | L | CTA |  |  |  |  |  |  |  | CTG |  | 0.19 |  |  |  |
| 24 | L | TTA |  |  |  |  |  |  |  | CTA | 0.35 | 5.72 | 1.31 | 2.16 | 0.63 |
|  |  |  |  |  |  |  |  |  |  | TTG | 12.49 | 0.81 | 0.59 | 1.01 | 0.27 |
| 25 | D | GAT | GGT | G | 0.12 | 0.12 |  |  |  | GAC | 0.23 | 0.93 | 0.05 | 0.14 |  |
| 26 | T | ACA | GCA | A |  | 0.12 |  |  |  |  |  |  |  |  |  |
| 27 | G | GGA |  |  |  |  |  |  |  | GGG | 0.12 | 0.06 |  |  |  |
| 28 | A | GCA |  |  |  |  |  |  |  | GCG | 0.12 |  | 0.09 | 0.14 |  |
| 29 | D | GAT | AAT | N | 0.12 |  | 0.05 |  | 0.09 | GAC | 0.23 | 0.19 |  |  |  |
| 30 | D | GAT |  |  |  |  |  |  |  | GAC |  | 0.06 | 0.09 | 0.14 | 0.09 |
| 31 | T | ACA |  |  |  |  |  |  |  | ACG |  | 0.12 |  |  |  |
| 32 | V | GTA |  |  |  |  |  |  |  | GTG |  | 0.25 |  |  |  |

TABLE 1-continued

Frequency of nonconsensus codons per position

| AApos[a] | AAc[b] | Cc[c] | Cm[d] | Am[e] | T1[f] | T2[g] | T3[h] | T3s[i] | T3r[j] | Cm[k] | T1[l] | T2[m] | T3[n] | T3s[o] | T3r[p] |
|---|---|---|---|---|---|---|---|---|---|---|---|---|---|---|---|
| 33 | L | TTA | GTA | V | 0.47 | 0.06 | | | | CTA | | 0.25 | 0.14 | 0.29 | 0.09 |
| | | | | | | | | | | TTG | 0.35 | 0.12 | 0.14 | 0.43 | |
| 34 | E | GAA | GGA | G | | 0.12 | 0.05 | | 0.09 | GAG | 0.12 | | 0.05 | 0.14 | |
| | | | CAA | | | | 0.09 | | | | | | | | |
| 35 | E | GAA | AAA | K | 0.12 | 0.06 | 0.09 | 0.14 | | | | | | | |
| 36 | M | ATG | ATA | I | 0.82 | 0.81 | 0.27 | 0.43 | 0.27 | | | | | | |
| 37 | N | AAT | AGT | S | | 0.19 | 0.05 | | | AAC | | 0.06 | 0.05 | 0.14 | |
| | | | GAT | D | 2.33 | 2.30 | 0.95 | 0.86 | 1.27 | | | | | | |
| 38 | L | TTG | | | | | | | | TTA | 0.23 | 0.62 | 0.05 | | 0.09 |
| 39 | P | CCA | | | | | | | | CCT | 0.23 | | | | |
| 40 | G | GGA | | | | | | | | GGG | 0.12 | 0.12 | | | |
| 41 | K | AAA | AGA | R | | 0.06 | 0.18 | 0.14 | 0.27 | AAG | 4.08 | 1.43 | 0.50 | 1.15 | 0.27 |
| 42 | W | TGG | CGG | R | 0.12 | 0.06 | | | | | | | | | |
| | | | TAG | — | 0.12 | | 0.05 | | 0.09 | | | | | | |
| | | | TGA | — | | | 0.14 | | 0.27 | | | | | | |
| 43 | K | AAA | AGA | R | | 0.06 | 0.05 | | 0.09 | AAG | 0.35 | | 0.14 | 0.14 | 0.18 |
| 44 | P | CCA | | | | | | | | CCG | | 0.06 | 0.23 | 0.43 | 0.18 |
| 45 | K | AAA | AGA | R | 0.12 | 0.12 | 0.05 | | 0.09 | AAG | 0.58 | 0.99 | 0.41 | 1.29 | |
| 46 | M | ATG | ATA | I | | 0.12 | 0.09 | 0.14 | 0.09 | | | | | | |
| 48 | G | GGA | GAA | E | | | 0.14 | 0.14 | 0.18 | GGG | 0.35 | 0.19 | | | |
| 49 | G | GGA | GAA | E | 0.12 | 0.06 | 0.05 | | 0.09 | GGG | 0.23 | 0.12 | | | |
| 50 | I | ATT | | | | | | | | ATC | 0.12 | 0.12 | | | |
| 51 | G | GGA | | | | | | | | GGG | 0.12 | 0.06 | | | |
| 52 | G | GGT | AGT | S | 0.12 | 0.06 | 0.05 | 0.14 | | GGA | | 0.06 | 0.05 | 0.14 | |
| | | | | | | | | | | GGC | 0.12 | 0.31 | 0.09 | 0.14 | 0.09 |
| | | | | | | | | | | GGG | | | 0.14 | 0.43 | |
| 53 | F | TTT | | | | | | | | TTC | 0.70 | | 0.05 | 0.14 | |
| 54 | I | ATC | ACC | T | 0.12 | 0.06 | 0.05 | | 0.09 | ATT | 0.35 | 0.06 | 0.14 | 0.14 | |
| 55 | K | AAA | AGA | R | 0.12 | | 0.05 | | 0.09 | AAG | 0.12 | 0.06 | | | |
| 56 | V | GTA | ATA | I | 0.12 | | 0.05 | 0.14 | | GTG | 0.75 | 0.14 | 0.14 | 0.18 | |
| 57 | R | AGA | AAA | K | 0.23 | | | | | AGG | 0.23 | 0.87 | 0.14 | 0.14 | 0.18 |
| 58 | Q | CAG | TAG | — | | | 0.05 | | 0.09 | CAA | 0.93 | 0.50 | 0.23 | 0.29 | 0.27 |
| 60 | D | GAT | AAT | N | | 0.12 | | | | | | | | | |
| | | | GGT | G | | 0.12 | | | | | | | | | |
| 61 | Q | CAA | CGA | R | 0.12 | 0.06 | 0.05 | 0.14 | | CAG | | 0.19 | 0.23 | 0.58 | |
| | | | TAA | — | 0.12 | 0.06 | 0.05 | | 0.09 | | | | | | |
| 62 | I | ATA | GTA | V | 0.35 | 0.06 | | | | | | | | | |
| 63 | L | CTC | CCC | P | 0.12 | | 0.41 | 0.58 | 0.36 | CTT | 11.32 | 5.41 | 1.27 | 2.88 | 0.45 |
| 64 | I | ATA | GTA | V | 1.05 | 0.06 | 0.09 | | 0.18 | | | | | | |
| | | | ATG | M | 0.23 | | 0.05 | 0.14 | | | | | | | |
| 65 | E | GAA | AAA | K | | | 0.09 | 0.14 | 0.09 | GAG | 0.35 | 0.06 | 0.05 | | |
| 66 | I | ATC | | | | | | | | ATA | | 0.25 | 0.18 | 0.58 | |
| | | | | | | | | | | ATT | 1.98 | 0.19 | | | |
| 67 | C | TGT | | | | | | | | TGC | 0.35 | 0.12 | 0.05 | 0.14 | |
| 68 | G | GGA | | | | | | | | GGG | 0.23 | 0.12 | 0.05 | 0.14 | |
| 69 | H | CAT | TAT | Y | 0.23 | 0.06 | 0.09 | 0.14 | | CAC | 0.82 | 0.31 | 0.14 | 0.29 | 0.09 |
| 70 | K | AAA | CAA | Q | 0.47 | 0.12 | 0.41 | 1.29 | | AAG | 3.27 | 10.88 | 15.27 | 6.62 | 25.34 |
| 71 | A | GCT | ACT | T | | 0.12 | 0.09 | | | | | | | | |
| 72 | I | ATA | GTA | V | 0.12 | 0.12 | | | | | | | | | |
| 73 | G | GGT | | | | | | | | GGC | 0.47 | 18.09 | 7.05 | 15.68 | 3.62 |
| 74 | T | ACA | | | | | | | | ACG | 0.23 | 0.12 | | | |
| 75 | V | GTA | ATA | I | 0.23 | 0.06 | 0.05 | | | GTG | 1.87 | 0.99 | 0.27 | 0.43 | 0.27 |
| | | | GCA | A | | | 0.09 | | 0.18 | | | | | | |
| 76 | L | TTA | | | | | | | | CTA | | 0.12 | 0.09 | | 0.18 |
| | | | | | | | | | | TTG | 0.93 | 0.62 | 0.27 | 0.43 | 0.18 |
| 77 | V | GTA | ATA | I | 0.23 | 0.56 | 0.72 | 2.01 | 0.18 | GTG | 0.82 | 0.62 | 0.23 | 0.58 | |
| | | | CTA | L | | | 0.14 | | | | | | | | |
| 78 | G | GGA | | | | | | | | GGG | 1.17 | 1.24 | 0.09 | 0.14 | |
| 79 | P | CCT | | | | | | | | CCC | 1.17 | 0.31 | 0.54 | 1.29 | 0.18 |
| 81 | P | CCT | | | | | | | | CCC | 0.12 | 0.19 | | | |
| | | | | | | | | | | CCG | 1.52 | 0.44 | | | |
| 82 | V | GTC | ATC | I | | 0.06 | 1.27 | 3.60 | | GTA | 0.35 | 0.31 | 0.05 | | |
| | | | CTC | L | | 0.06 | 1.08 | 3.45 | | GTT | 1.05 | 0.75 | 0.41 | 1.01 | |
| | | | GCC | A | | 0.12 | 49.89 | | 99.91 | | | | | | |
| | | | TTC | F | | | 0.14 | 0.43 | | | | | | | |
| 83 | N | AAC | AGC | S | 0.12 | | 0.05 | | 0.09 | AAT | 8.17 | 6.40 | 3.62 | 4.75 | 4.16 |
| 84 | I | ATA | GTA | V | | | 5.15 | | | | | | | | |
| 85 | I | ATT | | | | | | | | ATA | | 0.12 | 0.05 | 0.14 | |
| | | | | | | | | | | ATC | 0.12 | 0.12 | 0.05 | | |
| 86 | G | GGA | | | | | | | | GGG | | 0.12 | | | |
| | | | | | | | | | | GGT | 0.12 | 0.06 | | | |
| 87 | R | AGA | AAA | K | 0.12 | 0.06 | 0.05 | | 0.09 | AGG | 0.58 | 0.37 | 0.05 | 0.14 | |
| | | | GGA | G | | 0.06 | 0.09 | 0.14 | 0.09 | | | | | | |
| 88 | N | AAT | | | | | | | | AAC | 0.35 | 0.93 | | | |
| 89 | L | CTA | ATA | I | | 0.12 | | | | CTG | 1.17 | 0.68 | 1.36 | 1.87 | 1.54 |
| | | | | | | | | | | TTA | 1.98 | 0.56 | 1.27 | 0.14 | 2.44 |

TABLE 1-continued

Frequency of nonconsensus codons per position

| AApos[a] | AAc[b] | Cc[c] | Cm[d] | Am[e] | T1[f] | T2[g] | T3[h] | T3s[i] | T3r[j] | Cm[k] | T1[l] | T2[m] | T3[n] | T3s[o] | T3r[p] |
|---|---|---|---|---|---|---|---|---|---|---|---|---|---|---|---|
| 90 | L | TTG | ATG | M | 0.12 | | 13.56 | | 0.09 | CTG | 0.47 | | 0.09 | 0.14 | 0.09 |
|    |   |     | TCG | S | 0.12 |   | 0.05  |   | 0.09 | TTA | 0.47 | 0.19 | 0.14 | 0.43 |      |
| 91 | T | ACT | GCT | A |      | 0.06 | 0.05 |   | 0.09 | ACC | 0.12 | 0.06 | 0.09 | 0.14 | 0.09 |
|    |   |     |     |   |      |   |       |   |      | ACG | 0.12 | 0.12 | 0.77 |      | 1.54 |
| 92 | Q | CAG |     |   |      |   |       |   |      | CAA | 0.23 | 0.19 | 0.14 |      |      |
| 93 | I | ATT | CTT | L | 0.12 | 0.06 |    |   |      | ATC | 0.23 |      | 0.09 | 0.14 | 0.09 |
| 94 | G | GGT | GAT | D | 0.12 | 0.06 |    |   |      | GGA | 0.23 |      |      |      |      |
|    |   |     |     |   |      |   |       |   |      | GGC | 1.28 | 0.25 | 0.50 | 1.29 | 0.18 |
|    |   |     |     |   |      |   |       |   |      | GGG | 0.23 | 0.06 | 0.09 | 0.14 |      |
| 95 | C | TGC |     |   |      |   |       |   |      | TGT | 0.70 | 0.12 | 0.14 |      | 0.27 |
| 96 | T | ACT |     |   |      |   |       |   |      | ACA | 0.12 |      | 0.09 | 0.14 | 0.09 |
|    |   |     |     |   |      |   |       |   |      | ACC | 0.70 | 0.12 | 0.23 | 0.43 | 0.09 |
|    |   |     |     |   |      |   |       |   |      | ACG |      | 0.06 | 0.05 | 0.14 |      |
| 97 | L | TTA |     |   |      |   |       |   |      | CTA | 0.58 |      | 0.05 | 0.14 |      |
|    |   |     |     |   |      |   |       |   |      | TTG | 0.12 | 0.25 | 0.27 | 0.43 | 0.27 |

Only positions of diversity and SNPs that were represented by more than 1 sequence are shown.
Consensus
AApos[a] Amino acid position, protease.
AAc[b] Consensus amino acid in untreated population.
Cc[c] Consensus codon in untreated population.
Nonsynomous
Cm[d] Coding nonconsensus amino acid.
AAm[e] Coding nonconsensus codon.
T1[f] Frequency of SNP in first untreated time point.
T2[g] Frequency of SNP in second untreated time point.
T3[h] Frequency of SNP in third time point, treated.
T3s[i] Frequency of SNP in third time point, treated, susceptible population (not V82A, I84V, L90M).
T3r[j] Frequency of SNP in third time point, treated, population containing major ritonavir resistant variant V82A.
Synomous
Cm[k] Silent nonconsensus codon.
T1[l] Frequency of SNP in first untreated time point.
T2[m] Frequency of SNP in second untreated time point.
T3[n] Frequency of SNP in third time point, treated.
T3s[o] Frequency of SNP in third time point, treated, susceptible population (not V82A, I84V, L90M).

T3r[p] Frequency of SNP in third time point, treated, population containing major ritonavir resistant variant V82A.

TABLE 2

Summary of nucleotide variation in sampled time points

| Variable | T1 | T2 | T3 | T3s | T3r |
|---|---|---|---|---|---|
| No. of sequences | 810 | 1449 | 1925 | 547 | 970 |
| No. of polymorphic (segregating)sites | 104 | 115 | 110 | 71 | 69 |
| Total number of mutations | 115 | 129 | 121 | 75 | 73 |
| Average number nt differences, k | 2.38809 | 2.33683 | 3.08838 | 2.43819 | 2.05962 |
| Nucleotide diversity, π | 0.00804 | 0.00787 | 0.01040 | 0.00821 | 0.00693 |
| Theta (per sequence) | 14.29822 | 14.63943 | 13.51412 | 10.31864 | 9.25678 |
| Theta (per site) | 0.04814 | 0.04929 | 0.04550 | 0.03474 | 0.03117 |
| Tajima'sD | −2.3541 | −2.3164 | −2.0937 | −2.1606 | −2.1209 |
| Beta P value | 0.0013 | 0.0014 | 0.0070 | 0.0065 | 0.0071 |

T1 and T2 are untreated populations, and T3 is a population intermittently exposed to ritonavir monotherapy.
Within T3, T3s represents the sensitive (not V82A, I84V, or L90M) portion of the population.
T3r represents the major drug resistance clade V82A.

What is claimed is:

1. A method for detecting variants in a plurality of nucleic acid molecules comprising:
   (a) attaching a plurality of primers comprising a target specific sequence and a Primer ID, wherein the Primer ID further comprises a predetermined sequence, to a plurality of nucleic acid molecules in a sample, comprising a complex population, to generate tagged-nucleic acid templates, wherein (i) the plurality of nucleic acid molecules comprises 10 or more different nucleic acid templates wherein the different nucleic acid templates comprise nucleotide variants, and (ii) each tagged nucleic acid template is attached to a unique Primer ID;
   (b) amplifying the tagged nucleic acid templates to produce tagged amplicons; and
   (c) detecting the tagged amplicons, thereby detecting variants, wherein the method is capable of detecting variants present in less than 20% frequency in the complex population, in the plurality of nucleic acid molecules, wherein detecting the plurality of nucleic acid molecules comprises determining, with the aid of a computer processor, (i) PCR resampling in an amplification reaction; or (ii) a PCR error rate and/or sequencing error rate, wherein determining the PCR error rate and/or sequencing error rate comprises determining fidelity of a polymerase.

2. A method for detecting variants in a plurality of nucleic acid molecules comprising:
   (a) attaching a plurality of primers comprising a target specific sequence and a Primer ID, wherein the Primer ID further comprises a predetermined sequence, to a plurality of nucleic acid molecules in a sample, comprising a complex population, to generate tagged-nucleic acid templates, wherein (i) the plurality of nucleic acid molecules comprises 10 or more different nucleic acid templates wherein the different nucleic acid templates comprise nucleotide variants, and (ii) each tagged nucleic acid template is attached to a unique Primer ID;
   (b) amplifying the tagged nucleic acid templates to produce tagged amplicons; and
   (c) detecting the tagged amplicons, thereby detecting variants, wherein the method is capable of detecting variants present in less than 20% frequency in the complex population, in the plurality of nucleic acid molecules, wherein detecting the plurality of nucleic acid molecules comprises determining, with the aid of a computer processor, (i) PCR resampling in an amplification reaction; or (ii) a PCR error rate and/or sequencing error rate, wherein determining the PCR error rate and/or sequencing error rate comprises determining accuracy of oligonucleotides synthesized in vitro.

3. A method for detecting variants in a plurality of nucleic acid molecules comprising:
   (a) attaching a plurality of primers comprising a target specific sequence and a Primer ID, wherein the Primer ID further comprises a predetermined sequence, to a plurality of nucleic acid molecules in a sample, comprising a complex population, to generate tagged-nucleic acid templates, wherein (i) the plurality of nucleic acid molecules comprises 10 or more different nucleic acid templates wherein the different nucleic acid templates comprise nucleotide variants, and (ii) each tagged nucleic acid template is attached to a unique Primer ID;
   (b) amplifying the tagged nucleic acid templates to produce tagged amplicons; and
   (c) detecting the tagged amplicons, thereby detecting variants, wherein the method is capable of detecting variants present in less than 20% frequency in the complex population, in the plurality of nucleic acid molecules, wherein detecting the plurality of nucleic acid molecules comprises determining, with the aid of a computer processor, (i) PCR resampling in an amplification reaction; or (ii) a PCR error rate and/or sequencing error rate, wherein determining the PCR error rate and/or sequencing error rate comprises determining accuracy of a sequencing reaction.

4. The method of claim 3, wherein detecting the tagged amplicons comprises sequencing the tagged amplicons.

5. The method of claim 3, wherein detecting the tagged amplicons further comprises counting a number of different Primer IDs associated with the tagged amplicons, wherein the number of different Primer IDs associated with the tagged amplicons reflects the number of templates sampled.

6. The method of claim 3, further comprising forming a consensus sequence for tagged amplicons comprising the same Primer ID.

7. The method of claim 3, wherein the nucleic acid template comprises a DNA template.

8. The method of claim 3, wherein the nucleic acid template comprises an RNA template.

9. The method of claim 3, wherein the nucleic acid template comprises a non-viral template.

10. The method of claim 3, wherein the nucleic acid template molecules comprise a viral sequence or a bacterial sequence.

11. The method of claim 3, wherein the sample is from an individual suffering from a viral infection, a bacterial infection, a cancer, or an autoimmune disorder.

12. The method of claim 3, wherein the Primer ID comprises a degenerate sequence.

13. The method of claim 3, wherein the Primer ID is attached to the template by ligation, hybridization, or PCR.

14. The method of claim 3, wherein amplifying comprises a PCR-based method.

15. The method of claim 14, wherein the PCR-based method is selected from the group consisting of PCR, quantitative PCR, emulsion PCR, droplet PCR, hot start PCR, multiplex PCR, nested PCR and semi-nested PCR.

16. The method of claim 3, wherein the Primer ID comprises 5-100 nucleotides.

17. The method of claim 3, wherein the Primer ID comprises 5-50 nucleotides.

18. The method of claim 3, wherein the Primer ID comprises at least 8 nucleotides.

19. The method of claim 3, wherein the method is capable of detecting variants present in less than 2.5% of the complex population.

20. The method of claim 3, wherein the method is capable of detecting variants present in less than 1% of the complex population.

21. The method of claim 3, wherein the plurality of nucleic acid templates comprise at least 50 different nucleic acid templates.

22. The method of claim 3, wherein the plurality of nucleic acid templates comprise at least 200 different nucleic acid templates.

23. The method of claim 3, wherein the plurality of nucleic acid templates comprise at least 500 different nucleic acid templates.

24. The method of claim 3, wherein the plurality of primers comprising the target specific sequence and the Primer ID are attached to the plurality of nucleic acid molecules in the sample by primer extension.

* * * * *